US011339168B2

(12) United States Patent
Andres et al.

(10) Patent No.: US 11,339,168 B2
(45) Date of Patent: May 24, 2022

(54) CRYSTALLINE FORMS OF 6-(6-AMINOPYRAZIN-2-YL)-N-(4-(4-(OXETAN-3-YL)PIPERAZIN-1-YL)PHENYL) IMIDAZO[1,2-A]PYRAZIN-8-AMINE AS SYK INHIBITORS

(71) Applicant: Kronos Bio, Inc., San Mateo, CA (US)

(72) Inventors: Patricia Andres, West Lafayette, IN (US); Peter C. Fung, San Mateo, CA (US); Pierre Giguere, Edmonton (CA); Chiajen Lai, Livermore, CA (US); Craig Stewart, Natick, MA (US); Jing Teng, West Lafayette, IN (US); Duong D. Tran, Edmonton (CA); Iva Trantcheva, Sonoma, CA (US); Brian Yarmuch, Sherwood Park (CA)

(73) Assignee: Kronos Bio, Inc., San Mateo, CA (US)

( * ) Notice: Subject to any disclaimer, the term of this patent is extended or adjusted under 35 U.S.C. 154(b) by 11 days.

(21) Appl. No.: 16/796,479

(22) Filed: Feb. 20, 2020

(65) Prior Publication Data
US 2020/0291035 A1 Sep. 17, 2020

Related U.S. Application Data

(60) Provisional application No. 62/809,337, filed on Feb. 22, 2019.

(51) Int. Cl.
*A61K 31/4985* (2006.01)
*C07D 487/04* (2006.01)

(52) U.S. Cl.
CPC ........ *C07D 487/04* (2013.01); *C07B 2200/13* (2013.01)

(58) Field of Classification Search
CPC ................. A61K 31/4985; C07D 487/04
USPC ............................ 514/249; 544/350
See application file for complete search history.

(56) References Cited

U.S. PATENT DOCUMENTS

| | | | |
|---|---|---|---|
| 5,593,997 A | 1/1997 | Dow et al. | |
| 5,658,857 A | 8/1997 | Andree et al. | |
| 5,783,576 A | 7/1998 | Roos et al. | |
| 5,846,514 A | 12/1998 | Foster et al. | |
| 6,334,997 B1 | 1/2002 | Foster et al. | |
| 6,911,443 B2 | 6/2005 | Yura et al. | |
| 6,919,340 B2 | 7/2005 | Currie et al. | |
| 6,919,341 B2 | 7/2005 | Paruch et al. | |
| 7,160,885 B2 | 1/2007 | Currie et al. | |
| 7,189,723 B2 | 3/2007 | Mitchell et al. | |
| 7,259,164 B2 | 8/2007 | Mitchell et al. | |
| 7,312,341 B2 | 12/2007 | DeSimone et al. | |
| 7,405,295 B2 | 7/2008 | Currie et al. | |
| 8,354,526 B2 | 1/2013 | Ding et al. | |
| 8,440,667 B2 | 5/2013 | Mitchell et al. | |
| 8,450,321 B2 | 5/2013 | Mitchell et al. | |
| 8,455,493 B2 | 6/2013 | Mitchell et al. | |
| 8,546,370 B2 | 10/2013 | Okram et al. | |
| 8,697,699 B2 | 4/2014 | Mitchell et al. | |
| 8,748,607 B2 | 6/2014 | Mitchell et al. | |
| 8,765,761 B2 | 7/2014 | Mitchell et al. | |
| 8,796,270 B2 | 8/2014 | Mitchell | |
| 8,962,835 B2 | 2/2015 | Mitchell et al. | |
| 9,120,811 B2 | 9/2015 | Mitchell et al. | |
| 9,212,191 B2 | 12/2015 | Mitchell et al. | |
| 9,290,505 B2 | 3/2016 | Blomgren et al. | |
| 9,376,441 B2 | 6/2016 | Currie et al. | |
| 9,382,256 B2 | 7/2016 | Casteel et al. | |
| 9,504,684 B2 | 11/2016 | Blomgren et al. | |
| 9,562,056 B2 | 2/2017 | Blomgren et al. | |
| 9,567,348 B2 | 2/2017 | Mitchell et al. | |
| 9,657,023 B2 | 5/2017 | Elford et al. | |

(Continued)

FOREIGN PATENT DOCUMENTS

CA 2175837 5/1995
CA 2714414 8/2009

(Continued)

OTHER PUBLICATIONS

Abrisqueta et al., Personalizing treatment for chronic lymphocytic leukemia, Expert Review of Hematology, 2011, 4(1):27-35.

(Continued)

*Primary Examiner* — Douglas M Willis
(74) *Attorney, Agent, or Firm* — Knobbe, Martens, Olson & Bear LLP

(57) ABSTRACT

Solid forms of the compound, 6-(6-aminopyrazin-2-yl)-N-(4-(4-(oxetan-3-yl)piperazin-1-yl)phenyl)imidazo[1,2-a]pyrazin-8-amine, and solid forms of salts or co-crystals of Compound I, were prepared and characterized:

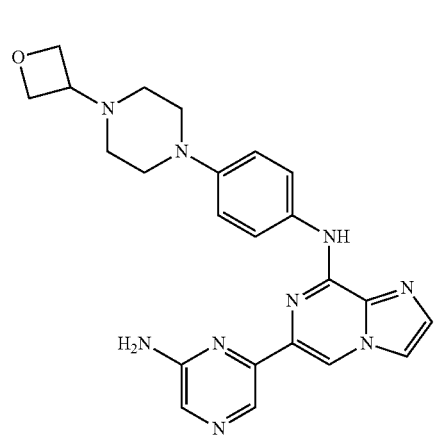

Compound I

Also provided are processes of making the solid forms and methods of use thereof.

4 Claims, 79 Drawing Sheets

(56) References Cited

U.S. PATENT DOCUMENTS

| | | |
|---|---|---|
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 9,918,939 B2 | 3/2018 | Casteel et al. |
| 9,931,338 B2 | 4/2018 | Blomgren et al. |
| 9,949,932 B2 | 4/2018 | Casteel et al. |
| 9,968,601 B2 | 5/2018 | Blomgren et al. |
| 9,974,792 B2 | 5/2018 | Di Paolo et al. |
| 10,005,774 B2 | 6/2018 | Blomgren et al. |
| 10,080,756 B2 | 9/2018 | Di Paolo et al. |
| 10,092,583 B2 | 10/2018 | Blomqren et al. |
| 10,093,684 B2 | 10/2018 | Blomgren et al. |
| 10,111,882 B2 | 10/2018 | Abella et al. |
| 10,266,539 B2 | 4/2019 | Elford et al. |
| 10,342,794 B2 | 7/2019 | Blomgren et al. |
| 10,828,299 B2 | 11/2020 | Blomgren et al. |
| 10,842,803 B2 | 11/2020 | Blomgren et al. |
| 2002/0037852 A1 | 3/2002 | Browninq et al. |
| 2003/0089434 A1 | 5/2003 | Flynn et al. |
| 2003/0212073 A1 | 11/2003 | Currie et al. |
| 2004/0022562 A1 | 2/2004 | Nakamura et al. |
| 2004/0026310 A1 | 2/2004 | Larsen |
| 2004/0026867 A1 | 2/2004 | Adams et al. |
| 2004/0026877 A1 | 2/2004 | Taylor et al. |
| 2004/0063715 A1 | 4/2004 | Paruch et al. |
| 2004/0067951 A1 | 4/2004 | DeSimone et al. |
| 2004/0072080 A1 | 4/2004 | Iwanaga et al. |
| 2004/0072081 A1 | 4/2004 | Coleman et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0005429 A1 | 1/2005 | Yi et al. |
| 2005/0009832 A1 | 1/2005 | Sun et al. |
| 2005/0014599 A1 | 1/2005 | Tay et al. |
| 2005/0019220 A1 | 1/2005 | Napoli |
| 2005/0047290 A1 | 3/2005 | Okada et al. |
| 2005/0054648 A1 | 3/2005 | Mitchell et al. |
| 2005/0054649 A1 | 3/2005 | Currie et al. |
| 2005/0085252 A1 | 4/2005 | Reyes |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0222199 A1 | 10/2005 | Hayman et al. |
| 2005/0288295 A1 | 12/2005 | Currie et al. |
| 2006/0044687 A1 | 3/2006 | Soeno et al. |
| 2006/0053121 A1 | 3/2006 | Zizys et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0027135 A1 | 2/2007 | Bruncko et al. |
| 2007/0072860 A1 | 3/2007 | Bruncko et al. |
| 2007/0117804 A1 | 5/2007 | Zhao et al. |
| 2008/0025821 A1 | 1/2008 | White et al. |
| 2009/0077334 A1 | 3/2009 | Ishida et al. |
| 2009/0102468 A1 | 4/2009 | Takahashi |
| 2009/0197809 A1 | 8/2009 | Anderson et al. |
| 2009/0221612 A1 | 9/2009 | Mitchell et al. |
| 2010/0006947 A1 | 1/2010 | Becker et al. |
| 2010/0027500 A1 | 2/2010 | Schulz et al. |
| 2010/0068257 A1 | 3/2010 | Boni et al. |
| 2010/0068258 A1 | 3/2010 | Cardona Iglesias et al. |
| 2010/0152159 A1 | 6/2010 | Mitchell et al. |
| 2010/0222323 A1 | 9/2010 | Mitchell et al. |
| 2010/0305122 A1 | 12/2010 | Bruncko et al. |
| 2010/0305125 A1 | 12/2010 | Borchardt et al. |
| 2011/0002989 A1 | 1/2011 | Curatolo et al. |
| 2011/0112995 A1 | 5/2011 | Chang et al. |
| 2012/0157470 A1 | 6/2012 | Catron et al. |
| 2012/0220582 A1 | 8/2012 | Mitchell et al. |
| 2013/0023499 A1 | 1/2013 | Mitchell et al. |
| 2013/0210802 A1 | 8/2013 | Blomgren et al. |
| 2013/0231330 A1 | 9/2013 | Mitchell et al. |
| 2013/0237520 A1 | 9/2013 | Mitchell et al. |
| 2013/0237521 A1 | 9/2013 | Mitchell et al. |
| 2013/0267496 A1 | 10/2013 | Mitchell et al. |
| 2013/0310363 A1 | 11/2013 | Mitchell et al. |
| 2013/0338142 A1 | 12/2013 | Blomgren et al. |
| 2014/0051696 A1 | 2/2014 | Lannutti et al. |
| 2014/0148430 A1 | 5/2014 | Blomgren et al. |
| 2014/0336169 A1 | 11/2014 | Mitchell et al. |
| 2014/0357627 A1 | 12/2014 | Mitchell et al. |
| 2015/0038488 A1 | 2/2015 | Currie et al. |
| 2015/0038504 A1 | 2/2015 | Casteel et al. |
| 2015/0038505 A1 | 2/2015 | Elford et al. |
| 2015/0150881 A1 | 6/2015 | Di Paolo et al. |
| 2015/0175616 A1 | 6/2015 | Blomgren et al. |
| 2015/0175626 A1 | 6/2015 | Cagulada et al. |
| 2015/0237860 A1 | 8/2015 | Anderson et al. |
| 2015/0266902 A1 | 9/2015 | Blomgren et al. |
| 2016/0031894 A1 | 2/2016 | Mitchell et al. |
| 2016/0058758 A1 | 3/2016 | Blomgren et al. |
| 2016/0166579 A1 | 6/2016 | Di Paolo et al. |
| 2016/0166580 A1 | 6/2016 | Casteel et al. |
| 2016/0168155 A1 | 6/2016 | Fung et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0095490 A1 | 4/2017 | Blomgren et al. |
| 2017/0121350 A1 | 5/2017 | Blomgren et al. |
| 2017/0217967 A1 | 8/2017 | Elford et al. |
| 2017/0258804 A1 | 9/2017 | Di Paolo et al. |
| 2018/0008608 A1 | 1/2018 | Di Paolo et al. |
| 2018/0071302 A1 | 3/2018 | Abella et al. |
| 2018/0071303 A1 | 3/2018 | Abella et al. |
| 2018/0086769 A1 | 3/2018 | Armistead et al. |
| 2018/0099971 A1 | 4/2018 | Elford et al. |
| 2018/0117052 A1 | 5/2018 | Di Paolo et al. |
| 2018/0280387 A1 | 10/2018 | Blomgren et al. |
| 2018/0325896 A1 | 11/2018 | Blomgren et al. |
| 2019/0117679 A1 | 4/2019 | Blomgren et al. |
| 2019/0388419 A1 | 12/2019 | Blomgren et al. |

FOREIGN PATENT DOCUMENTS

| | | |
|---|---|---|
| CN | 101124227 | 2/2008 |
| DE | 4337609 | 5/1995 |
| EP | 0480713 | 4/1992 |
| JP | 2001-302667 | 10/2001 |
| JP | 2004-528295 | 9/2004 |
| JP | 2005-530739 | 10/2005 |
| JP | 2008-519843 | 6/2008 |
| JP | 2011-511835 | 4/2011 |
| NZ | 593460 | 11/2013 |
| WO | WO-88/04298 | 6/1988 |
| WO | WO-95/12594 | 5/1995 |
| WO | WO-96/04298 | 2/1996 |
| WO | WO 96/004298 | 2/1996 |
| WO | WO 96/034866 | 11/1996 |
| WO | WO-96/34866 | 11/1996 |
| WO | WO-99/28322 | 6/1999 |
| WO | WO 01/027119 | 4/2001 |
| WO | WO-01/27119 | 4/2001 |
| WO | WO-01/34119 | 5/2001 |
| WO | WO-01/47495 | 7/2001 |
| WO | WO 01/083485 | 11/2001 |
| WO | WO-01/83485 | 11/2001 |
| WO | WO-02/10170 | 2/2002 |
| WO | WO 02/010170 | 2/2002 |
| WO | WO-02/30428 | 4/2002 |
| WO | WO 02/030428 | 4/2002 |
| WO | WO-02/060492 | 8/2002 |
| WO | WO-02/066481 | 8/2002 |
| WO | WO-02/076985 | 10/2002 |
| WO | WO-03/070732 | 8/2003 |
| WO | WO-03/089434 | 10/2003 |
| WO | WO-2004/022562 | 3/2004 |
| WO | WO-2004/026310 | 4/2004 |
| WO | WO-2004/026867 | 4/2004 |
| WO | WO-2004/026877 | 4/2004 |
| WO | WO-2004/072080 | 8/2004 |
| WO | WO-2004/072081 | 8/2004 |

(56) References Cited

FOREIGN PATENT DOCUMENTS

| WO | WO-2005/005429 | 1/2005 |
| --- | --- | --- |
| WO | WO-2005/014599 | 2/2005 |
| WO | WO-2005/019220 | 3/2005 |
| WO | WO-2005/047290 | 5/2005 |
| WO | WO-2005/085252 | 9/2005 |
| WO | WO-2006/009769 | 1/2006 |
| WO | WO-2006/044687 | 4/2006 |
| WO | WO-2006/053121 | 5/2006 |
| WO | WO-2008/025821 | 3/2008 |
| WO | WO-2008/033854 | 3/2008 |
| WO | WO-2009/039397 | 3/2009 |
| WO | WO-2009/070639 | 6/2009 |
| WO | WO-2009/077334 | 6/2009 |
| WO | WO-2009/102252 | 8/2009 |
| WO | WO-2009/102468 | 8/2009 |
| WO | WO-2009/137596 | 11/2009 |
| WO | WO-2009/156284 | 12/2009 |
| WO | WO-2010/000633 | 1/2010 |
| WO | WO-2010/006947 | 1/2010 |
| WO | WO-2010/027500 | 3/2010 |
| WO | WO-2010/068257 | 6/2010 |
| WO | WO-2010/068258 | 6/2010 |
| WO | WO-2011/074961 | 6/2011 |
| WO | WO-2011/112995 | 9/2011 |
| WO | WO-2012/147832 | 11/2012 |
| WO | WO 13/188856 | 12/2013 |
| WO | WO-2014/028665 | 2/2014 |
| WO | WO-2015/017460 | 2/2015 |
| WO | WO-2015/017466 | 2/2015 |
| WO | WO-2015/017610 | 2/2015 |
| WO | WO-2015/100217 | 7/2015 |

OTHER PUBLICATIONS

Ackler et al., Navitoclax (ABT-263) and bendamustine ± rituximab induce enhanced killing of non-Hodgkin's lymphoma tumours in vivo, British Journal of Pharmacology, (2012), vol. 167, pp. 881-891.
Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.
Ashizawa, Kazuhide, Shio/kettushoukei no saitekika to kettushouka gijyutsu, (Optimization of Salt and Crystal Form and Crystallization Technique), Pharm Tech Japan, 2002, vol. 18, No. 10, pp. 81-96.
Bastin et al., Salt Selection and Optimisation Procedures for Pharmaceutical New Chemical Entities, Organic Process Research and Development, American Chemical Society, 2000, vol. 4, No. 5, pp. 427-435.
Berge et al. Journal of Pharmaceutical Sciences 66(1) (1977), pp. 1-19.
Blazar et al., Advances in graft-versus-host disease biology and therapy, Nat Rev Immunol. 2013, 12(6), pp. 443-458.
Bouloc et al., Structure-based design of imidazo[1,2-a]pyrazine derivatives as selective inhibitors of Aurora-A kinase in cells. Bioorganic & Medicinal Chemistry Letters 20 (2010) 5988-5993.
Brittain, Harry G., "Polymorphism in Pharmaceutical Solids", Informa Healthcare, New York, 2009.
Buchner et al., Spleen tyrosine kinase inhibition prevents chemokine- and integrin-mediated stromal protective effects in chronic lymphocytic leukemia, Blood 2010, vol. 115, No. 22, pp. 4497-4506.
Bundgaard, H., (1985). Design of prodrugs: Bioreversible derivatives for various functional groups and chemical entities, Elsevier Science Publishers, B.V., The Netherlands, p. 1.
Burke et al., A potential therapeutic strategy for chronic lymphocytic leukemia by combining Idelalisib and GS-9973, a novel spleen tyrosine kinase (Syk) inhibitor, Oncotarget 2014, vol. 5, No. 4, pp. 908-915.
Burrell et al., "The causes and consequences of genetic heterogeneity in cancer evolution" Nature 501, pp. 338-345 (2013).
Cancer Types, A to Z List of Cancer Types—National Cancer Institute, 2017. (8 pages).
CancerConnect.Com, Ibrutinib Highly Active in Patients with Chronic Lymphocytic Leukemia with 17p Deletion, Aug. 17, 2013. (2 pages).
ClinicalTrials.gov, A Phase 2 of GS-9973 in Subjects With Relapsed or Refractory Hematologic Malignancies, NCT01799889, Jun. 2013.
Communication pursuant to Article 94(3) European Application No. 14750289.2 dated Dec. 14, 2017. (4 pages).
Communication pursuant to Rules 161(1) and 162 for European Application No. 14750289.2 dated Mar. 8, 2016. (2 pages).
Currie et al., Discovery of GS-9973, a Selective and Orally Efficacious Inhibitor of Spleen Tyrosine Kinase, J. Med. Chem. 2014, 57, pp. 3856-3873.
Dean, D.C. (2000). "Recent Advances in the Synthesis and Applications of Radiolabeled Compounds for Drug Discovery and Development," Curr. Pharm Des. 6(10): Preface, 1 page.
Ding, S. et al. (2002) "A Combinatorial Scaffold Approach Toward Kinase-Directed Heterocycle Libraries," J. Am Chem Soc., 124(8): 1594-1596.
Elder, et al, (2010), The Utility of Sulfonate Salts in Drug Development, J Pharm Sci, vol. 99, Issue 7, pp. 2948-2961.
European Communication dated Jun. 18, 2013, for EP Patent Application No. 11709600.8 filed on Mar. 11, 2011, 6 pages.
European Communication dated Jun. 6, 2013, for EP Patent Application No. 09832228.2 filed on Jun. 21, 2011, 5 pages.
European Communication dated Oct. 24, 2012, for European Patent Application No. 09710901.1, filed on Feb. 12, 2009. (5 pages).
Evans, E.A. (1981). "Synthesis of Radiolabeled Compounds," Journal of Radioanalytical Chemistry, vol. 64, No. 1-2, pp. 9-32.
Examination Report for AU Appln. No. 2017225136 dated May 7, 2018, 3 pages.
Examination Report for IN Appln. No. 201617001841 dated Jul. 5, 2018, 5 pages.
Examination Report for AU Appln. No. 2014296308 dated Apr. 27, 2017, 3 pages.
Examination Report for AU Appln. No. 2014296308 dated Jul. 14, 2016, 3 pages.
Examination Report for Pakistan Appln. No. 550/2014 dated May 5, 2016, 2 pages.
Examination Report for New Zealand Appln. No. 715776 dated Aug. 2, 2016, 3 pages.
Examiner's Report for Canadian Application No. 2,919,661 dated Oct. 3, 2017. (3 pages).
Extended European search report for European Application No. 16164453.9 dated Oct. 19, 2016. (7 pages).
Extended European Search Report dated Apr. 26, 2012, for EP 09832229.0, filed on Jun. 21, 2011, 6 pages.
Extended European Search Report dated Jul. 27, 2012, for EP 09832228.2, filed on Jun. 21, 2011, 12 pages.
Extended European Search Report dated Mar. 12, 2014, for EP 13005979.3, filed on Dec. 20, 2013, 5 pages.
Final Office Action dated Jan. 27, 2012, for U.S. Appl. No. 12/632,151, filed Dec. 7, 2009, 15 pages.
Final Office Action dated May 2, 2013 for U.S. Appl. No. 13/343,624, filed Jan. 4, 2012, 9 pages.
Final Office Action dated May 25, 2012, for U.S. Appl. No. 12/632,140, filed Dec. 7, 2009, 9 pages.
Final Office Action dated Oct. 30, 2012, for U.S. Appl. No. 12/632,140, filed Dec. 7, 2009, 9 pages.
Final Office Action dated Sep. 15, 2011, for U.S. Appl. No. 12/632,140, filed Dec. 7, 2009, 15 pages.
Final Office Action dated Sep. 5, 2012, for U.S. Appl. No. 12/632,151, filed Dec. 7, 2009, 11 pages.
Final Office Action for U.S. Appl. No. 13/806,094 dated Feb. 11, 2016. (8 pages).
Final Office Action for U.S. Appl. No. 15/010,906 dated Jun. 16, 2017. (36 pages).
Final Office Action for U.S. Appl. No. 14/907,767 dated Jul. 17, 2017. (15 pages).
Final Office Action for U.S. Appl. No. 14/906,248 dated Jul. 26, 2017. (8 pages).

(56) References Cited

OTHER PUBLICATIONS

Final Office Action for U.S. Appl. No. 15/404,120 dated Jul. 28, 2017. (19 pages).
Final Office Action for U.S. Appl. No. 15/298,950 dated Aug. 24, 2017. (31 pages).
Final Office Action for U.S. Appl. No. 14/559,707 dated Dec. 10, 2015. (11 pages).
Flynn, R.P., B cells, T follicular helpers, and germinal centers as facilitators of chronic Graftversus-Host disease. Doctoral Dissertation, University of Minnesota, Aug. 2014.Bruce R. Blazar.
Gavezzotti, A, Are Crystal Structures Predictable? Acc. Chem. Res. 1994, 27(10), pp. 309-314.
GenBank Accession No. AY050647.1, created on Oct. 7, 2001, located at <http://www.ncbi.nlm.nih.gov/nuccore/AY050647.1>, last visited on Dec. 28, 2011, 1 page.
Golub et al., Molecular Classification of Cancer: Class Discovery and Class Prediction by Gene Expression Monitoring, Science 1999, vol. 286, pp. 531-537.
Hackam, D.G. et al. (2006). "Translation of Research Evidence From Animals to Humans," *JAMA* 296(14):1731-1732.
Hill et al., B-Cell Antigen Receptor Signaling in Chronic Lymphocytic Leukemia: Therapeutic Targets and Translational Opportunities, International Reviews of Immunology 2013, 32, pp. 377-396.
Hirayama, Handbook for creating organic compound crystals—principle and technical know-how, Maruzen KK, Jul. 25, 2008, pp. 17-23, pp. 37-40, pp. 45-51, and pp. 57-65.
International Preliminary Examination Report dated Aug. 5, 2004, for PCT Application No. PCT/US2003/12222, filed Apr. 21, 2003, 11 pages.
International Preliminary Examination Report dated Oct. 27, 2004, for PCT Application No. PCT/US2003/28329, filed on Sep. 9, 2003, 5 pages.
International Preliminary Report on Patentability dated Jan. 24, 2011, for PCT Application No. PCT/US2009/006445, filed on Dec. 7, 2009, 6 pages.
International Preliminary Report on Patentability dated Oct. 29, 2010, for PCT Application No. PCT/US/2009/006446, filed on Dec. 7, 2009, 6 pages.
International Preliminary Report on Patentability for International Application No. PCT/US2014/048733 dated Feb. 2, 2016. (6 pages).
International Preliminary Report on Patentability dated Aug. 17, 2010, for PCT Application No. PCT/US2009/000919, filed on Feb. 12, 2009, 8 pages.
International Search Report and Written Opinion for International Application No. PCT/US2016/028303 dated Jun. 23, 2016. (9 pages).
International Search Report and Written Opinion dated Oct. 13, 2014, for PCT Application No. PCT/US2014/048741, Filed Jul. 29, 2014, 10 pages.
International Search Report and Written Opinion dated Dec. 30, 2004, for PCT Application No. PCT/US2004/018227, filed on Jun. 4, 2004, 10 pages.
International Search Report and Written Opinion dated Dec. 8, 2004, for PCT Application No. PCT/US2004/021150, filed on Jun. 30, 2004, 10 pages.
International Search Report and Written Opinion dated Feb. 1, 2005 for PCT Application No. PCT/US2004/025884, filed on Aug. 11, 2004, 8 pages.
International Search Report and Written Opinion dated Jul. 7, 2004, for PCT Application No. PCT/US2004/003922, filed on Feb. 10, 2004, 12 pages.
International Search Report and Written Opinion dated Jul. 7, 2004, for PCT Application No. PCT/US2004/003923, filed on Feb. 10, 2004, 12 pages.
International Search Report and Written Opinion dated Jun. 23, 2005, for PCT Application No. PCT/US2004/037433, filed on Nov. 10, 2004, 15 pages.
International Search Report and Written Opinion dated Oct. 8, 2014, for PCT Application No. PCT/US2014/048733, filed on Jul. 29, 2014, 8 pages.

International Search Report dated Apr. 26, 2011, for Application No. PCT/US2011/028194, filed on Mar. 11, 2011, 5 pages.
International Search Report dated Feb. 12, 2010, for PCT Application No. PCT/US09/06446, filed on Dec. 7, 2009, 3 pages.
International Search Report dated Feb. 12, 2010, for PCT Application No. PCT/US09/06445, filed on Dec. 7, 2009, 3 pages.
International Search Report dated Feb. 9, 2004, for PCT Application No. PCT/US03/28329, filed on Sep. 9, 2003. (4 pages).
International Search Report dated May 12, 2009, for PCT Application No. PCT/US2009/000919, filed on Feb. 12, 2009, 5 pages.
International Search Report dated Mar. 5, 2015, for PCT Application No. PCT/US2014/071842, filed Dec. 22, 2014, 3 pgs.
International Search Report dated Oct. 22, 2003, for PCT Application No. PCT/US03/12222, filed on Apr. 21, 2003. (6 pages).
Invitation to Pay Additional Fees with Partial International Search Report dated May 3, 2005, for PCT Application No. PCT/US2004/037433, filed on Nov. 10, 2004, 9 pages.
Japanese Decision of Patent dated Feb. 4, 2014, for Japanese Patent Application No. 2010-546786, filed on Aug. 1, 2010, 4 pages. (with English translation).
Japanese Notice of Reasons for Rejection dated Feb. 4, 2014 for Japanese Patent Application No. 2011-539524, filed on Jun. 6, 2011, 6 pages. (with English translation).
Japanese Notice of Reasons for Rejection dated on Feb. 6, 2014, for Japanese Patent Application No. 2011-539525, filed on Jun. 6, 2011, 11 pages. (with English translation).
Jeffery et al. (1998). "Phosphodiesterase III and V Inhibitors on Pulmonary Artery from Pulmonary Hypertensive Rats: Differences Between Early and Established Pulmonary Hypertension", J. Cardiovascular Pharmacology, 32(2): 213-219.
Jordan, V.C. (Mar. 2003). "Tamoxifen: A Most Unlikely Pioneering Medicine" *Nature Reviews: Drug Discovery* 2:205-213.
Kabalka, G.W. et al. (1989). "The Synthesis of Radiolabeled Compounds via Organometallic Intermediates," *Tetrahedron* 45(21):6601-6621.
Kojima, Takashi, Iyakuhin Kaihatsu ni okeru kettushousei sentaku no kouritsuka wo mezashite (Aiming for better efficiency of crystalline selection in the development of pharmaceuticals), Journal of Pharmaceutical Science and Technology, Japan 2008, vol. 68, No. 5, pp. 344-349.
Krisenko et al., Calling in SYK: SYK's Dual Role as a Tumor Promoter and Tumor Suppressor in Cancer, Biochim Biophys Acta. 2015, 1853(1):254-263.
Kuhnz, W. et al. (Jun. 11, 1998). "Predicting the Oral Bioavailability of 19-Nortestosterone Progestins In Vivo From Their Metabolic Stability in Human Liver Microsomal Preparations In Vitro," *The American Society for Pharmacology and Experimental Therapeutics* 26(11), pp. 1120-1127.
Le Huu et al., Blockade of Syk ameliorates the development of murine sclerodermatous chronic graft-versus-host disease, Journal of Dermatological Science, 74(2014), pp. 214-221.
Lumma, Jr., W.C. et al. (1983) "Piperazinylimidazo [1,2-a]pyrazines with Selective affinity for in Vitro a-Adrenergic Receptor Subtypes," *J. Med. Chem.* 26(3):357-363.
Ma et al., Signal transduction inhibitors in chronic lymphocytic leukemia, Current Opinion in Oncology 2011, 23:601-608.
Merino et al., Bcl-2, Bcl-xL, and Bcl-w are not equivalent targets of ABT-737 and navitoclax (ABT-263) in lymphoid and leukemic cells, Blood. 2012;119(24):5807-5816.
Non-Final Office Action dated Feb. 12, 2016 for U.S. Appl. No. 14/795,123, 13 pages.
Non-Final Office Action dated Jul. 7, 2015 for U.S. Appl. No. 14/578,973, 11 pages.
Non-Final Office Action dated Apr. 13, 2011 for U.S. Appl. No. 12/370,103, filed Feb. 12, 2009, 11 pages.
Non-Final Office Action dated Apr. 3, 2006, for U.S. Appl. No. 10/776,002, filed Feb. 10, 2004, 13 pages.
Non-Final Office Action dated Dec. 31, 2013, for U.S. Appl. No. 13/901,523, filed May 23, 2013, 22 pages.
Non-Final Office Action dated Feb. 17, 2012 for U.S. Appl. No. 12/632,140, filed Dec. 7, 2009, 11 pages.
Non-Final Office Action dated Jan. 25, 2013, for U.S. Appl. No. 13/343,624, filed Jan. 4, 2012, 18 pages.

(56) References Cited

OTHER PUBLICATIONS

Non-Final Office Action dated Jan. 8, 2007, for U.S. Appl. No. 10/915,696, filed Aug. 11, 2004, 8 pages.
Non-Final Office Action dated Jun. 29, 2011, for U.S. Appl. No. 12/632,151, filed Dec. 7, 2009, 17 pages.
Non-Final Office Action dated May 10, 2011 for U.S. Appl. No. 12/632,140, filed Dec. 7, 2009, 18 pages.
Non-Final Office Action dated May 17, 2012, for U.S. Appl. No. 12/632,151, filed Dec. 7, 2009, 15 pages.
Non-Final Office Action dated May 24, 2006, for U.S. Appl. No. 10/776,631, filed Feb. 10, 2004, 10 pages.
Non-Final Office Action dated Nov. 4, 2013, for U.S. Appl. No. 13/862,147, filed Apr. 12, 2013, 18 pages.
Non-Final Office Action dated Oct. 11, 2012, for U.S. Appl. No. 13/441,441, filed Apr. 6, 2012, 8 pages.
Non-Final Office Action dated Oct. 11, 2013, for U.S. Appl. No. 13/868,967, filed Apr. 23, 2013, 17 pages.
Non-Final Office Action dated Oct. 16, 2013, for U.S. Appl. No. 13/868,971, filed Apr. 23, 2013, 16 pages.
Non-Final Office Action dated Sep. 26, 2006, for U.S. Appl. No. 10/658,121, filed Sep. 9, 2003, 7 pages.
Non-Final Office Action for U.S. Appl. No. 15/010,906 dated Jan. 20, 2017. (30 pages).
Non-Final Office Action for U.S. Appl. No. 14/300,189 dated Feb. 3, 2015. (17 pages).
Non-Final Office Action for U.S. Appl. No. 14/882,278 dated Mar. 1, 2017. (18 pages).
Non-Final Office Action for U.S. Appl. No. 14/907,767 dated Mar. 10, 2017. (81 pages).
Non-Final Office Action for U.S. Appl. No. 15/298,950 dated Mar. 27, 2017. (10 pages).
Non-Final Office Action for U.S. Appl. No. 14/906,248 dated Apr. 14, 2017. (10 pages).
Non-Final Office Action for U.S. Appl. No. 15/404,120 dated Apr. 21, 2017. (16 pages).
Non-Final Office Action for U.S. Appl. No. 14/446,011 dated Apr. 22, 2016. (22 pages).
Non-Final Office Action for U.S. Appl. No. 13/806,094 dated Jun. 14, 2016. (12 pages).
Non-Final Office Action for U.S. Appl. No. 15/017,394 dated Jun. 16, 2017. (24 pages).
Non-Final Office Action for U.S. Appl. No. 14/796,795 dated Jun. 17, 2016. (11 pages).
Non-Final Office Action for U.S. Appl. No. 13/806,094 dated Jul. 2, 2015. (13 pages).
Non-Final Office Action for U.S. Appl. No. 10/985,023 dated Jul. 10, 2009. (32 pages).
Non-Final Office Action for U.S. Appl. No. 10/985,023 dated Oct. 8, 2008. (16 pages).
Non-Final Office Action for U.S. Appl. No. 10/985,023 dated Dec. 12, 2007. (17 pages).
Non-Final Office Action for U.S. Appl. No. 10/985,023 dated Apr. 29, 2010. (2 pages).
Non-Final Office Action for U.S. Appl. No. 14/445,970 dated Jul. 15, 2015. (13 pages).
Non-Final Office Action for U.S. Appl. No. 14/559,707 dated Aug. 7, 2015. (13 pages).
Non-Final Office Action for U.S. Appl. No. 14/559,707 dated Sep. 16, 2016. (12 pages).
Non-Final Office Action for U.S. Appl. No. 15/133,041 dated Aug. 9, 2017. (18 pages).
Non-Final Office Action for U.S. Appl. No. 15/603,663 dated Aug. 9, 2017. (13 pages).
Non-Final Office Action for U.S. Appl. No. 15/387,557 dated Aug. 24, 2017. (10 pages).
Non-Final Office Action for U.S. Appl. No. 14/274,618 dated Dec. 8, 2014. (9 pages).
Non-Final Office Action for U.S. Appl. No. 15/178,164 dated Dec. 15, 2016. (34 pages).
Non-Final Office Action for U.S. Appl. No. 15/484,844 dated May 5, 2017. (22 pages).
Notice of Allowance and Fees Due for U.S. Appl. No. 14/446,011 dated Jan. 12, 2017. (8 pages).
Notice of Allowance and Fees Due for U.S. Appl. No. 14/448,160 dated Feb. 16, 2016. (25 pages).
Notice of Allowance and Fees Due for U.S. Appl. No. 14/559,707 dated Feb. 24, 2017. (7 pages).
Notice of Allowance and Fees Due for U.S. Appl. No. 14/445,970 dated Mar. 9, 2016. (8 pages).
Notice of Allowance and Fees Due for U.S. Appl. No. 14/274,618 dated Mar. 17, 2015. (9 pages).
Notice of Allowance and Fees Due for U.S. Appl. No. 14/796,795 dated Apr. 27, 2017. (8 pages).
Notice of Allowance and Fees Due for U.S. Appl. No. 14/629,390 dated Apr. 28, 2016. (10 pages).
Notice of Allowance and Fees Due for U.S. Appl. No. 14/882,278 dated Jun. 16, 2017. (8 pages).
Notice of Allowance and Fees Due for U.S. Appl. No. 14/300,189 dated Jul. 13, 2015. (9 pages).
Notice of Allowance and Fees Due for U.S. Appl. No. 15/178,164 dated Aug. 3, 2017. (7 pages).
Notice of Allowance and Fees Due for U.S. Appl. No. 14/446,011 dated Sep. 22, 2016. (8 pages).
Notice of Allowance and Fees Due for U.S. Appl. No. 13/806,094 dated Oct. 4, 2016. (8 pages).
Notice of Allowance and Fees Due for U.S. Appl. No. 14/629,390 dated Oct. 13, 2015. (10 pages).
Notice of Allowance and Fees Due for U.S. Appl. No. 14/629,390 dated Oct. 14, 2016. (11 pages).
Notice of Allowance and Fees Due for U.S. Appl. No. 14/796,795 dated Dec. 5, 2016. (8 pages).
Notice of Allowance dated Apr. 20, 2007, for U.S. Appl. No. 10/915,696, filed Aug. 11, 2004, 7 pages.
Notice of Allowance dated Aug. 11, 2006, for U.S. Appl. No. 10/776,002, filed Feb. 10, 2004, 10 pages.
Notice of Allowance dated Aug. 8, 2007, for U.S. Appl. No. 10/658,121, filed Sep. 9, 2003, 4 pages.
Notice of Allowance dated Mar. 6, 2007, for U.S. Appl. No. 10/658,121, filed Sep. 9, 2003, 6 pages.
Notice of Allowance dated Aug. 12, 2013, for U.S. Appl. No. 13/343,624, filed Jan. 4, 2012, 9 pages.
Notice of Allowance dated Dec. 26, 2013, for U.S. Appl. No. 13/343,624, filed Jan. 4, 2012, 10 pages.
Notice of Allowance dated Feb. 12, 2014, for U.S. Appl. No. 13/862,147, filed Apr. 12, 2013, 9 pages.
Notice of Allowance dated Feb. 5, 2014, for U.S. Appl. No. 13/868,967, filed Apr. 23, 2013, 8 pages.
Notice of Allowance dated Jan. 14, 2013, for U.S. Appl. No. 12/632,151, filed Dec. 7, 2009, 8 pages.
Notice of Allowance dated Jan. 25, 2013, for U.S. Appl. No. 12/632,140, filed Dec. 7, 2009, 8 pages.
Notice of Allowance dated Jan. 28, 2013, for U.S. Appl. No. 13/441,441, filed Apr. 6, 2012, 8 pages.
Notice of Allowance dated Jan. 30, 2014, for U.S. Appl. No. 13/868,971, filed Apr. 23, 2013, 8 pages.
Notice of Allowance and Fees Due for U.S. Appl. No. 13/862,194 dated Oct. 16, 2014. (8 pages).
Notice of Allowance dated Sep. 7, 2006, for U.S. Appl. No. 10/776,631, filed Feb. 10, 2004, 7 pages.
Office Action and Search Report for Chinese Application No. 201480043503.5 dated Oct. 28, 2016. (10 pages).
Office Action for Chinese Application No. 201480043503.5 dated Jun. 13, 2017. (7 pages).
Office Action for Canadian Application No. 2,919,661 dated Jan. 20, 2017. (4 pages).
Office Action for European Application No. 14750289.2 dated Apr. 13, 2017. (6 pages).
Office Action for Japanese Application No. 2016-531837 dated Apr. 17, 2017. (4 pages).
Office Action for Eurasian Application No. 201690127/28 dated Apr. 19, 2017 (4 pages).

(56) References Cited

OTHER PUBLICATIONS

Office Action for Japan Patent Application No. 2016-531837 dated Dec. 5, 2016. (10 pages).
Office Action dated Dec. 15, 2014 for Japan Patent Application No. 2014-095907. (2 pages).
Office Action dated Jan. 15, 2015 for Chilean Patent Application No. 1360-11. (8 pages).
Office Action dated Nov. 14, 2017 for Chilean Patent Application No. 2016-00238. (29 pages).
Office Action dated Jan. 30, 2015 for Vietnamese Patent Application No. 1-2011-01623. (1 page).
Office Action dated Feb. 18, 2015 for Eurasian Patent Application No. 201400197. (3 pages).
Office Action dated Mar. 30, 2015 for European Patent Application No. 13005979.3. (3 pages).
Office Action for Cuban Appl. No. 2016-0019 dated Sep. 29, 2017. (3 pages).
Office Action dated Apr. 15, 2016 for Canadian Appl. No. 2,746,023. (4 pages).
Office Action dated Apr. 20, 2016 for Korean Appl. No. 2011-7015724. (8 pages).
Office Action dated Apr. 21, 2017 for Korean Appl. No. 10-2017-7002329. (6 pages).
Office Action dated Apr. 25, 2017 for Singapore Appl. No. 201309094-9. (3 pages).
Office Action dated Dec. 29, 2016 for Korean Appl. No. 10-2011-7015724. (9 pages).
Office Action dated Jan. 31, 2017 for Korean Appl. No. 10-2014-7035525. (12 pages).
Office Action dated Jun. 17, 2016 for Japanese Appl. No. 2015-159313. (1 page).
Office Action dated Jun. 20, 2016 for Korean Appl. No. 10-2014-7035525. (20 pages).
Office Action dated Mar. 11, 2016 for Singapore Appl. No. 201309094-9. (12 pages).
Office Action dated May 19, 2016 for Israel Appl. No. 234326. (3 pages).
Office Action dated May 30, 2016 for Chinese Appl. No. 201510093652.9. (9 pages).
Office Action dated Nov. 16, 2016 for Canadian Appl. No. 2,746,023. (3 pages).
Office Action dated Oct. 13, 2016 for Japanese Appl. No. 2015-159313. (6 pages).
Office Action and Search Report for Taiwan Application No. 103125871 dated Jan. 17, 2018. (11 pages).
Office Action dated Jul. 27, 2017 for Chilean Application No. 2016-00241 (10 pages).
Office Action dated Oct. 5, 2017 for Columbian Patent Application No. 16-050.937 (31 pages).
Office Action dated Apr. 19, 2017 for Eurasian Patent Application No. 201690127/28 (8 pages).
Office Action dated May 25, 2016 for Eurasian Patent Application No. 201690172/28. (5 pages).
Office Action dated Dec. 22, 2016 for Japanese Patent Application No. JP 2016-531839 (13 pages).
Office Action dated Nov. 21, 2016 for Korean Patent Application No. 10-2016-7004789 (10 pages).
Office Action dated Aug. 19, 2016 for Pakistan Patent Application No. 551/2014 (2 pages).
Office Action for TW Appln. No. 103125870 dated Jun. 27, 2018, 4 pages.
Office Action for Colombian Appln. No. 16-51186 dated Mar. 22, 2016. (6 pages).
Office Action for Colombian Appln. No. 16-51186 dated Oct. 7, 2017. (9 pages).
Office Action for Korean Appln. No. 10-2016-700526 dated Jun. 16, 2017. (12 pages).
Office Action for Ukraine Appln. No. a201601036 dated Jan. 8, 2018. (4 pages).
Office Action for Ukraine Appln. No. a201601036 dated Jul. 10, 2017. (4 pages).
Office Action for U.S. Appl. No. 13/862,194 dated Jul. 28, 2014. (7 pages).
Opposition for Chilean Patent Application No. 2016-000238 dated Feb. 9, 2017. (6 pages).
Oravcova, J. et al. (1996). "Drug-Protein Binding Studies New Trends in Analytical and Experimental Methodology," Journal of Chromatography B, 677, pp. 1-28.
Owen et al., "Obinutuzumab for the treatment of lymphoproliferative disorders", Expert Opinion Biol. Ther. (2012), vol. 12, No. 3, pp. 343-351.
Paulekuhn et al., Trends in Active Pharmaceutical Ingredient Salt Selection based on Analysis of the Orange Book Database, J. Med. Chem. 2007, 50, 6665-6672.
Report of the state of the art for Panamanian App No. 91014-01 dated Jun. 16, 2017. (5 pages).
Resolution No. 56355 dated Dec. 18, 2014 for Colombian Patent Application No. 14-049-611. (4 pages).
Restriction Requirement dated Dec. 8, 2010, for U.S. Appl. No. 12/632,140, filed Dec. 7, 2009, 10 pages.
Restriction Requirement dated Jan. 27, 2006, for U.S. Appl. No. 10/776,631, filed Feb. 10, 2004, 6 pages.
Restriction Requirement dated Jan. 30, 2006, for U.S. Appl. No. 10/658,121, filed Sep. 9, 2003, 5 pages.
Restriction Requirement dated Jan. 4, 2006, for U.S. Appl. No. 10/776,002, filed Feb. 10, 2004, 7 pages.
Restriction Requirement dated May 18, 2006, for U.S. Appl. No. 10/658,121, filed Sep. 9, 2003, 5 pages.
Restriction Requirement dated Oct. 13, 2006, for U.S. Appl. No. 10/915,696, filed Aug. 11, 2004, 5 pages.
Restriction Requirement dated Oct. 20, 2004, for U.S. Appl. No. 10/419,682, filed Apr. 21, 2003, 9 pages.
Restriction Requirement dated Apr. 14, 2014, for U.S. Appl. No. 13/862,194, filed Apr. 12, 2013, 5 pages.
Restriction Requirement dated Dec. 8, 2010, for U.S. Appl. No. 12/632,151, filed Dec. 7, 2009, 10 pages.
Restriction Requirement dated Feb. 17, 2011, for U.S. Appl. No. 12/370,103, filed Feb. 12, 2009, 10 pages.
Restriction Requirement dated Jan. 27, 2014, for U.S. Appl. No. 13/609,068, filed Nov. 26, 2012, 8 pages.
Restriction Requirement dated Jul. 26, 2012, for U.S. Appl. No. 13/441,441, filed Apr. 6, 2012, 9 pages.
Restriction Requirement dated Jul. 3, 2013, for U.S. Appl. No. 13/868,971, filed Apr. 23, 2013, 5 pages.
Restriction Requirement dated Jun. 14, 2013, for U.S. Appl. No. 13/862,147, filed Apr. 12, 2013, 10 pages.
Restriction Requirement dated Jun. 24, 2013, for U.S. Appl. No. 13/868,967, filed Apr. 23, 2013, 10 pages.
Restriction Requirement dated Nov. 27, 2012, for U.S. Appl. No. 13/343,624, filed Jan. 4, 2012, 10 pages.
Restriction Requirement dated Oct. 15, 2013, for U.S. Appl. No. 13/901,523, filed May 23, 2013, 5 pages.
Restriction Requirement dated Sep. 8, 2014, for U.S. Appl. No. 14/274,618, filed May 9, 2014, 6 pages.
Restriction Requirement for U.S. Appl. No. 15/133,041 dated Jan. 25, 2017. (10 pages).
Restriction Requirement for U.S. Appl. No. 15/404,120 dated Feb. 15, 2017. (10 pages).
Restriction Requirement for U.S. Appl. No. 13/806,094 dated Mar. 27, 2015. (10 pages).
Restriction Requirement for U.S. Appl. No. 14/629,390 dated Jun. 30, 2015 (8 pages).
Restriction Requirement for U.S. Appl. No. 10/985,023 dated Aug. 16, 2007. (8 pages).
Restriction Requirement for U.S. Appl. No. 15/150,038 dated Nov. 7, 2016. (9 pages).
Restriction Requirement for U.S. Appl. No. 13/609,068 dated Jan. 27, 2014. (8 pages).
Roberts et al., Substantial Susceptibility of Chronic Lymphocytic Leukemia to BCL2 Inhibition: Results of a Phase I Study of Navitoclax in Patients With Relapsed or Refractory Disease, J Clin Oncol 2012, 30:488-496.

(56) References Cited

OTHER PUBLICATIONS

Second Written Opinion dated Apr. 13, 2004, for PCT Application No. PCT/US03/12222, filed Apr. 21, 2003, 7 pages.
Serajuddin, A. T. M., "Salt formation to improve drug solubility" Advanced Drug Delivery Reviews, vol. 59, pp. 603-616 (2007).
Silverman, R.B. (1992), The Organic Chemistry of Drug Design and Drug Action, Academic Press, Inc. San Diego, CA, pp. 352-400.
Stenberg, K.A.E. et al., (2000). "KinMutBase, a Database of Human Disease-Causing Protein Kinase Mutations", *Nucleic Acids Research* 28(1):369-371.
Substantive Examination dated Feb. 23, 2016 for Indonesian Application No. P00201601242 (2 pages).
Supplementary Examination Written Opinion for SG Appln. No. 11201600385T dated Mar. 5, 2018, 5 pages.
Takada, Noriyuki, "API form screening and selection in drug discovery stage," Pharm Stage, vol. 6, No. 10, pp. 20-25 (2007).
Taylor, R. et al., (1984). "Hydrogen-Bond Geometry in Organic Crystals", *Acc. Chem Res*. 17:320-326.
Vassilev et al., Therapeutic Potential of Inhibiting Bruton's Tyrosine Kinase, (BTK), Current Pharmaceutical Design, 2004, 10, 1757-1766.
Vippagunta et al., Crystalline solids, Advanced Drug Delivery Reviews 48 (2001), pp. 3-26.
Vitse, O. et al. (1999). "New Imidazo [1,2-α]pyrazine Derivatives with Bronchodilatory and Cyclic Nucleotide Phosphodiesterase Inhibitory Activities," *Bioorganic and Medicinal Chemistry* 7:1059-1065.
Willander et al., NOTCH1 Mutations Influence Survival in Chronic Lymphocytic Leukemia Patients, BMC Cancer 2013, 13:274. (6 pages).
Written Opinion dated May 4, 2011, for Application No. PCT/US2011/028194, filed on Mar. 11, 2011, 6 pages.
Written Opinion dated Dec. 5, 2003, for PCT Application No. PCT/US03/12222, filed Apr. 21, 2003, 6 pages.
Written Opinion dated Jul. 6, 2004, for PCT Application No. PCT/US03/28329, filed on Sep. 9, 2003, 5 pages.
Written Opinion dated Feb. 12, 2010, for PCT Application No. PCT/US/2009/006446, filed on Dec. 7, 2009, 4 pages.
Written Opinion dated Feb. 12, 2010, for PCT Application No. PCT/US2009/006445, filed on Dec. 7, 2009, 4 pages.
Written Opinion dated May 12, 2009, for PCT Application No. PCT/US2009/000919, filed on Feb. 12, 2009, 7 pages.
Zaragoza Dorwald, F. (2005). Side Reactions in Organic Synthesis: A Guide to Successful Synthesis Design, Weinheim; WILEY-VCH Verlag GmbH & Co. KGaA, Preface, 2 pages.
Caira, Jan. 1998, Crystalline polymorphism of organic compounds, Topics in Current Chemistry, 198:163-208.

CRYSTALLINE FORMS OF 6-(6-AMINOPYRAZIN-2-YL)-N-(4-(4-(OXETAN-3-YL)PIPERAZIN-1-YL)PHENYL) IMIDAZO[1,2-A]PYRAZIN-8-AMINE AS SYK INHIBITORS

CROSS-REFERENCE TO RELATED APPLICATIONS

This application claims the benefit of priority to U.S. Provisional Patent Application No. 62/809,337, filed 22 Feb. 2019, the contents of which are incorporated herein by reference in their entirety.

BACKGROUND

The present disclosure relates to polymorphs and polymorph pharmaceutical compositions of compounds that inhibit Spleen Tyrosine Kinase (Syk) activity. The disclosure also relates to methods of preparing such polymorphs and polymorph pharmaceutical compositions, and the use of such polymorphs and pharmaceutical compositions in treating subjects with various diseases, including cancer and inflammatory conditions.

The inhibition of Spleen Tyrosine Kinase (Syk) activity may be useful for treating certain types of cancer and autoimmune diseases. One such compound that has been found to inhibit Syk activity is represented by Compound I:

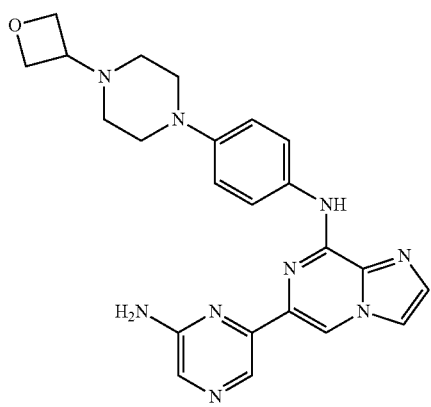

Compound I or a pharmaceutically acceptable salt thereof. Compound I is useful in the treatment of diseases and conditions mediated by Syk as demonstrated in U.S. Pat. No. 9,290,505, which is incorporated herein by reference in its entirety. U.S. Pat. No. 9,290,505 discloses crystalline forms of mono mesylate salts and succinate salts of Compound I, namely, Compound I Mono-MSA Forms I and II and Compound I Succinate Forms I and II. There is a need for polymorph forms of compounds that are efficacious and have improved bioavailability and/or physical properties.

SUMMARY

The present disclosure provides a crystalline form of Compound I:

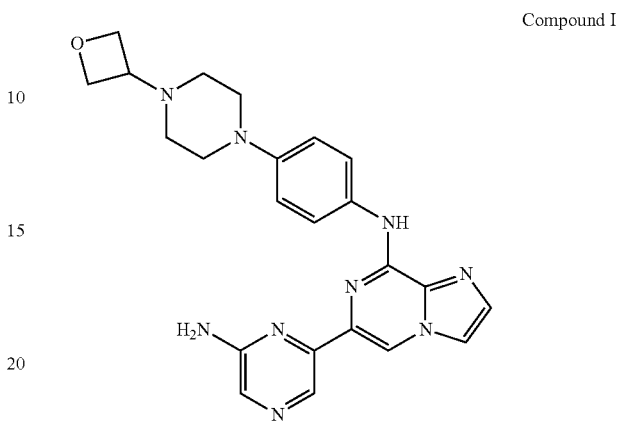

Compound I wherein the crystalline form is Compound I Form I, Compound I Form II, Compound I Form III, Compound I Form V, Compound I Form VII, Compound I Form VIII, Compound I Form IX, Compound I Form XIII or Compound I Form XIV.

The present disclosure also provides pharmaceutical compositions comprising the crystalline forms of Compound I or crystalline forms of salts or co-crystals of Compound I. The disclosure also provides processes for making crystalline forms of Compound I or crystalline forms of salts or co-crystals of Compound I. The disclosure also provides methods for using crystalline forms of Compound I or crystalline forms of salts or co-crystals of Compound I in Syk mediated diseases or conditions.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form I). Compound I Form I can be characterized by an X-ray powder diffractogram comprising the following peaks (±0.2° 2θ) at 15.2, 18.0 and 20.0° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form II). Compound I Form II can be characterized by an X-ray powder diffractogram comprising the following peaks (±0.2° 2θ) at 19.5, 20.8 and 22.2° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form III). Compound I Form III can be characterized by an X-ray powder diffractogram comprising the following peaks (±0.2° 2θ) at 7.6, 14.2 and 20.8° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form V). Compound I Form V can be characterized by an X-ray powder diffractogram comprising the following peaks (±0.2° 2θ) at 17.7, 19.7 and 22.7° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form VII). Compound I Form VII can be characterized by an X-ray powder diffractogram comprising the following peaks (±0.2° 2θ) at 8.4, 18.6 and 20.6° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form VIII). Compound I Form VIII can be characterized by an X-ray powder diffractogram comprising the following peaks (±0.2° 2θ) at 18.3, 20.8 and 21.9° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form IX). Compound I Form IX can be characterized by an X-ray powder diffractogram comprising the following peaks (±0.2° 2θ) at 14.0, 16.7 and 18.2° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form XIII). Compound I Form XIII can be characterized by an X-ray powder diffractogram comprising the following peaks (±0.2° 2θ) at 9.6, 19.3 and 20.8° 2θ, as determined on a diffractometer using Cu-Kα radiation.

One embodiment is directed to crystalline 6-(6-aminopyrazin-2-yl)-N-(4-(4-(oxetan-3-yl)piperazin-1-yl)phenyl)imidazo[1,2-a]pyrazin-8-amine (Compound I Form XIV). Compound I Form XIV can be characterized by an X-ray powder diffractogram comprising the following peaks (±0.2° 2θ) at 19.4, 22.5 and 23.3° 2θ, as determined on a diffractometer using Cu-Kα radiation.

In one embodiment, the present disclosure provides a crystalline form of a sesqui-succinate salt, a hemi-succinate salt, a mono-HCl salt, a sesqui-adipate salt, a mono-adipate salt, a bis-citrate salt, a sesqui-fumarate salt, a bis-gentisate salt, a mono-besylate (mono-BSA) salt, a sesqui-oxalate salt or a co-crystal of Compound I:

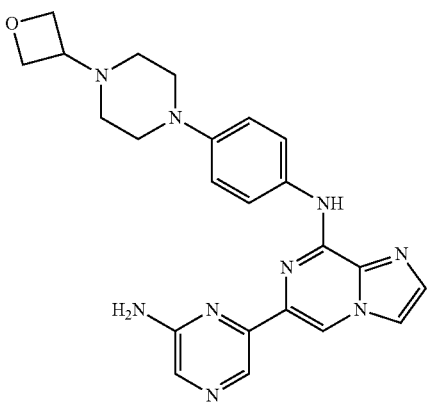

Compound I wherein the crystalline form or the co-crystal is Compound I Sesqui-Succinate Form III, Compound I Sesqui-Succinate Form IV, Compound I Sesqui-Succinate Form V, Compound I Hemi-Succinate Form I, Compound I Mono-HCl salt Form I, Compound I Mono-HCl salt Form II, Compound I Mono-HCl salt Form III, Compound I Sesqui-Adipate Form I, Compound I Mono-Adipate Form I, Compound I Bis-Citrate Form I, Compound I Sesqui-Fumarate Form I, Compound I Bis-Gentisate Form I, Compound I Mono-BSA salt Form I and Compound I Sesqui-Oxalate Form I.

One embodiment is directed to a crystalline sesqui-succinate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Sesqui-Succinate Form III). Compound I Sesqui-Succinate Form III can be characterized by an X-ray powder diffractogram comprising the following peaks (±0.2° 2θ) at 7.8, 16.5 and 21.4° 2θ, as determined on a diffractometer using Cu-Kα radiation.

One embodiment is directed to a crystalline sesqui-succinate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Sesqui-Succinate Form IV). Compound I Sesqui-Succinate Form IV can be characterized by an X-ray powder diffractogram comprising the following peaks (±0.2° 2θ) at 16.6, 22.4 and 25.2° 2θ, as determined on a diffractometer using Cu-Kα radiation.

One embodiment is directed to a crystalline sesqui-succinate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Sesqui-Succinate Form V). Compound I Sesqui-Succinate Form V can be characterized by an X-ray powder diffractogram comprising the following peaks (±0.2° 2θ) at 5.9, 23.3 and 24.7° 2θ, as determined on a diffractometer using Cu-Kα radiation.

One embodiment is directed to a crystalline hemi-succinate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Hemi-Succinate Form I). Compound I Hemi-Succinate Form I can be characterized by an X-ray powder diffractogram comprising the following peaks (±0.2° 2θ) at 20.8, 23.1 and 25.5° 2θ, as determined on a diffractometer using Cu-Kα radiation.

One embodiment is directed to a crystalline mono-HCl salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Mono-HCl salt Form I). Compound I Mono-HCl salt Form I can be characterized by an X-ray powder diffractogram comprising the following peaks (±0.2° 2θ) at 8.7, 19.3 and 21.4° 2θ, as determined on a diffractometer using Cu-Kα radiation.

One embodiment is directed to a crystalline mono-HCl salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Mono-HCl salt Form II). Compound I Mono-HCl salt Form II can be characterized by an X-ray powder diffractogram comprising the following peaks (±0.2° 2θ) at 6.3, 11.3 and 17.7° 2θ, as determined on a diffractometer using Cu-Kα radiation.

One embodiment is directed to a crystalline mono-HCl salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Mono-HCl salt Form III). Compound I Mono-HCl salt Form III can be characterized by an X-ray powder diffractogram comprising the following peaks (±0.2° 2θ) at 8.6, 17.8 and 24.0° 2θ, as determined on a diffractometer using Cu-Kα radiation.

One embodiment is directed to a crystalline sesqui-adipate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Sesqui-Adipate Form I). Compound I Sesqui-Adipate Form I can be characterized by an X-ray powder diffractogram comprising the following peaks (±0.2° 2θ) at 11.3, 16.6 and 24.8° 2θ, as determined on a diffractometer using Cu-Kα radiation.

One embodiment is directed to a crystalline mono-adipate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Mono-Adipate Form I). Compound I Mono-Adipate Form I can be characterized by an X-ray powder diffractogram comprising the following peaks (±0.2° 2θ) at 4.9, 19.9 and 21.1° 2θ, as determined on a diffractometer using Cu-Kα radiation.

One embodiment is directed to a crystalline bis-citrate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Bis-Citrate Form I). Compound I Bis-Citrate Form I can be characterized by an X-ray powder diffractogram comprising the following peaks (±0.2° 2θ) at 6.4, 18.1 and 18.9° 2θ, as determined on a diffractometer using Cu-Kα radiation.

One embodiment is directed to a crystalline sesqui-fumarate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Sesqui-Fumarate Form I). Compound I Sesqui-Fumarate Form I can be characterized by an X-ray powder diffractogram comprising the following peaks (±0.2° 2θ) at 15.3, 22.8 and 25.8° 2θ, as determined on a diffractometer using Cu-Kα radiation.

One embodiment is directed to a crystalline bis-gentisate salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Bis-Gentisate Form I). Compound I Bis-Gentisate Form I can be characterized by an X-ray powder diffractogram comprising the following peaks (±0.2° 2θ) at 6.7, 16.7 and 25.0° 2θ, as determined on a diffractometer using Cu-Kα radiation.

One embodiment is directed to a crystalline mono-BSA salt or a co-crystal of 6-(6-aminopyrazin-2-yl)-N-(4-(4-(oxetan-3-yl)piperazin-1-yl)phenyl)imidazo[1,2-a]pyrazin-8-amine (Compound I Mono-BSA Form I). Compound I Mono-BSA Form I can be characterized by an X-ray powder diffractogram comprising the following peaks (±0.2° 2θ) at 8.8, 11.8 and 20.2° 2θ, as determined on a diffractometer using Cu-Kα radiation.

One embodiment is directed to a crystalline sesqui-oxalate salt or a co-crystal of of 6-(6-aminopyrazin-2-yl)-N-(4-(4-(oxetan-3-yl)piperazin-1-yl)phenyl)imidazo[1,2-a]pyrazin-8-amine (Compound I Sesqui-Oxalate Form I). Compound I Sesqui-Oxalate Form I can be characterized by an X-ray powder diffractogram comprising the following peaks (±0.2° 2θ) at 16.1, 23.0 and 26.1° 2θ, as determined on a diffractometer using Cu-Kα radiation.

One embodiment is directed to a pharmaceutical composition comprising a compound selected from Compound I Form I, Compound I Form II, Compound I Form III, Compound I Form IV, Compound I Form V, Compound I Form VI, Compound I Form VII, Compound I Form VIII, Compound I Form IX, Compound I Form X, Compound I Form XI, Compound I Form XII, Compound I Form XIII, Compound I Form XIV, Compound I Sesqui-Succinate Form III, Compound I Sesqui-Succinate Form IV, Compound I Sesqui-Succinate Form V, Compound I Hemi-Succinate Form I, Compound I Mono-HCl salt Form I, Compound I Mono-HCl salt Form II, Compound I Mono-HCl salt Form III, Compound I HCl material A, Compound I HCl material B, Compound I Sesqui-Adipate Form I, Compound I Mono-Adipate Form I, Compound I Bis-Citrate Form I, Compound I Sesqui-Fumarate Form I, Compound I Bis-Gentisate Form I, Compound I Mono-BSA Form I, and Compound I Sesqui-Oxalate and a pharmaceutically acceptable excipient.

Another embodiment is directed to a method for treating a disease or condition selected from the group consisting of an inflammatory disorder, an allergic disorder, an autoimmune disease, and a cancer in a subject in need thereof, comprising administering to the subject a therapeutic effective amount of a crystalline form of Compound I or a crystalline form of a salt or a co-crystal of Compound I, or a combination thereof, as described herein.

In one embodiment, the disease or condition is selected from the group consisting of asthma, rheumatoid arthritis, multiple sclerosis, chronic obstructive pulmonary disease, and systemic lupus erythematosus. In another embodiment, the disease or condition is rheumatoid arthritis.

In another embodiment, the disease or condition is a cancer selected from the group consisting of a hematologic malignancy and a solid tumor. In another embodiment, the hematologic malignancy is lymphoma, multiple myeloma or leukemia.

Still an additional embodiment includes, optionally in combination with any other embodiment described herein, is the use of one or more of crystalline forms of Compound I or one or more crystalline forms of a salt or co-crystal of Compound I in the manufacture of a medicament for treating subjects suffering from or at risk of a disease or condition selected from the group consisting of an inflammatory disorder, an allergic disorder, an autoimmune disease, and a cancer.

DETAILED DESCRIPTION

Figure 1:
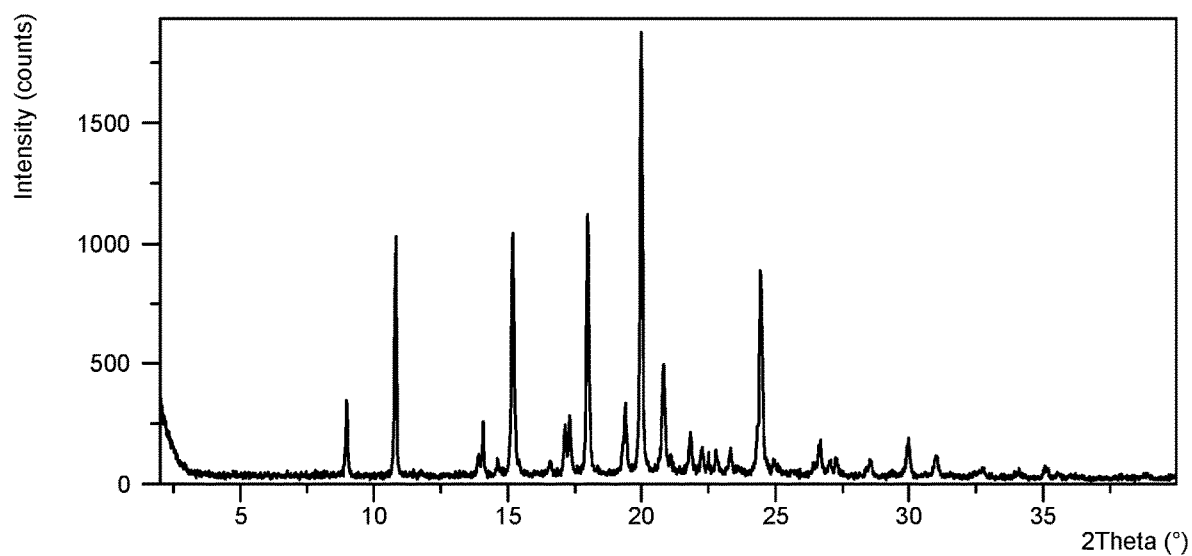
FIG. 1 is an X-ray powder diffractogram of Compound I Form I.

The compound named 6-(6-aminopyrazin-2-yl)-N-(4-(4-(oxetan-3-yl)piperazin-1-yl)phenyl)imidazo[1,2-a]pyrazin-8-amine is useful in treatments for subjects suffering from or at risk of spleen tyrosine kinase (Syk) mediated disease or condition and has the following structure:

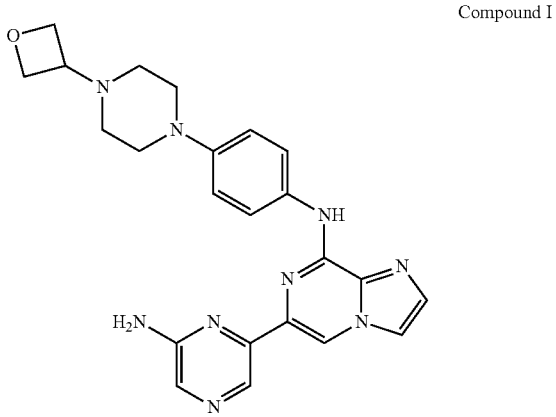 [SMILES: Nc1cncc(-c2cn3ccnc3c(Nc3ccc(N4CCN(C5COC5)CC4)cc3)n2)n1]

Compound I

The present disclosure relates to crystalline forms of Compound I and crystalline forms of salts or co-crystals of Compound I and processes for making the crystalline forms and use thereof.

Definitions

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. For example, when used in the context of quantitative measurements, the term "about" would refer to the indicated amount ±10%, ±5% or ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "therapeutically effective amount" refers to an amount of the compound as described herein that is sufficient to effect treatment as defined above, when administered to a patient (particularly a human) in need of such treatment in one or more doses. The therapeutically effective amount will vary, depending upon the patient, the disease being treated, the weight and/or age of the patient, the severity of the disease, or the manner of administration as determined by a qualified prescriber or care giver.

The term "salt" refers to a salt of Compound I. In some cases, the "salt" of Compound I is a pharmaceutically acceptable salt. Compound I is capable of forming, for example, acid addition salts by virtue of the presence of amino groups. Pharmaceutically acceptable acid addition salts may be prepared from inorganic and organic acids. Salts derived from inorganic acids include, but are not limited to, hydrochloric acid, hydrobromic acid, sulfuric acid, nitric acid, phosphoric acid, and the like. Salts derived from organic acids include, but are not limited to, acetic acid, adipic acid, citric acid, gentisic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "co-crystal" refers to a molecular complex of an ionized or non-ionized Compound I and one or more non-ionized co-crystal formers (such as a pharmaceutically acceptable salt) connected through non-covalent interactions.

The term "solvate" refers to a crystal form with either a stoichiometric or non-stoichiometric amount of solvent incorporated into the crystal structure. Similarly, the term "hydrate" refers specifically to a crystal form with either a stoichiometric or non-stoichiometric amount of water incorporated into the crystal structure.

In addition, abbreviations as used herein have respective meanings as follows:

| | |
|---|---|
| Aq. | Aqueous |
| d | Doublet |
| DCM | Dichloromethane |
| DMAP | 4-Dimethylaminopyridine |
| DMF | Dimethylformamide |
| DMSO | Dimethylsulfoxide |
| DSC | Differential scanning calorimetry |
| DVS | Dynamic vapor sorption |
| EtOAc | Ethyl acetate |
| EtOH | Ethanol |
| IPAc | Isopropyl acetate |
| LCMS | Liquid chromatography-mass spectrometry |
| m | Multiplet |
| MEK | Methyl ethyl ketone |
| MeOH | Methanol |
| 2-MeTHF | 2-Methyl tetrahydrofuran |
| $Pd_2(dba)_3$ | Tris(dibenzylideneacetone)dipalladium(0) |
| $Pd(PPh_3)_4$ | Tetrakis(triphenylphosphine)palladium(0) |
| RH | Relative humidity |
| RT | Room temperature |
| s | Singlet |
| TGA | Thermogravimetric analysis |
| XRPD | X-ray powder diffraction |
| THF | Tetrahydrofuran |

Crystalline Forms of Compound I

As described generally above, the present disclosure provides crystalline forms of Compound I and crystalline forms of salts or co-crystals of Compound I.

Compound I Form I

Compound I Form I is an unsolvated form. Compound I Form I can be characterized by an X-ray powder diffractogram comprising peaks (±0.2° 2θ) at 15.2, 18.0 and 20.0° 2θ, as determined on a diffractometer using Cu-Kα radiation. The diffractogram can comprise additional peaks (±0.2° 2θ) at 10.8, 20.8 and 24.4° 2θ. Compound I Form I can be characterized by an X-ray powder (XRPD) diffractogram as substantially shown in FIG. 1. In one embodiment, Compound I Form I can be characterized by an X-ray powder diffractogram comprising at least three, at least four or at least five peaks (±0.2° 2θ) selected from 20.0, 18.0, 15.2, 10.8, 24.4, 20.8, 9.0, 19.4, 17.3° 2θ, as determined on a diffractometer using Cu-Kα radiation.

Figure 2:
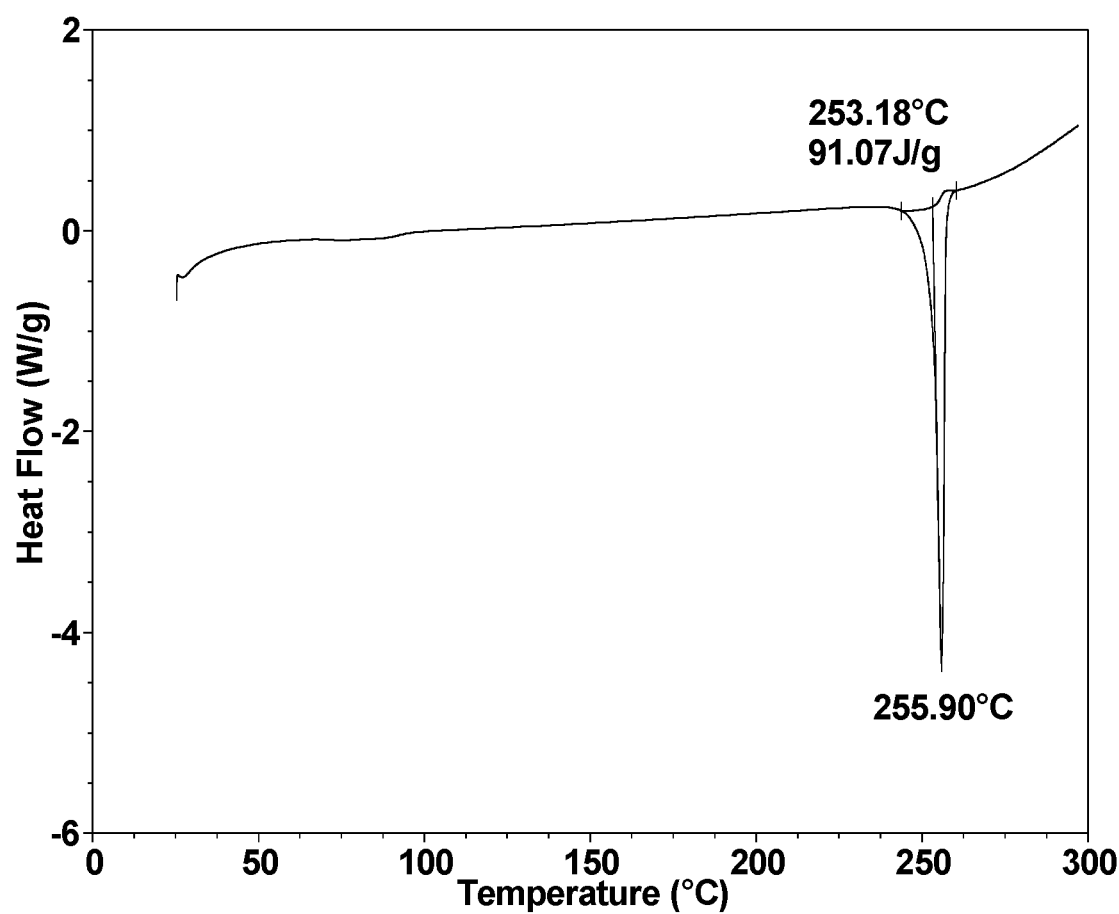
FIG. 2 is a differential scanning calorimetry (DSC) curve of Compound I Form I.
Figure 3:
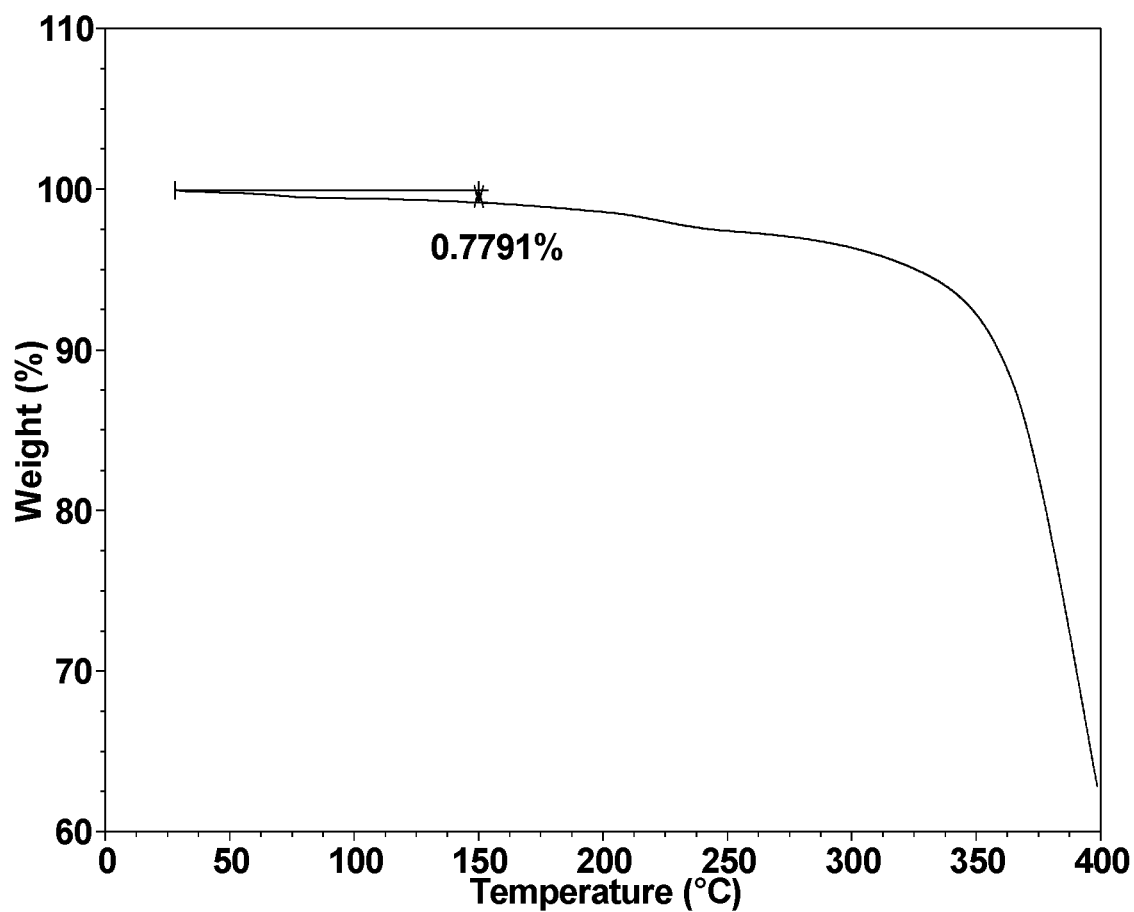
FIG. 3 is a thermogravimetric analysis (TGA) curve of Compound I Form I.
Figure 4:
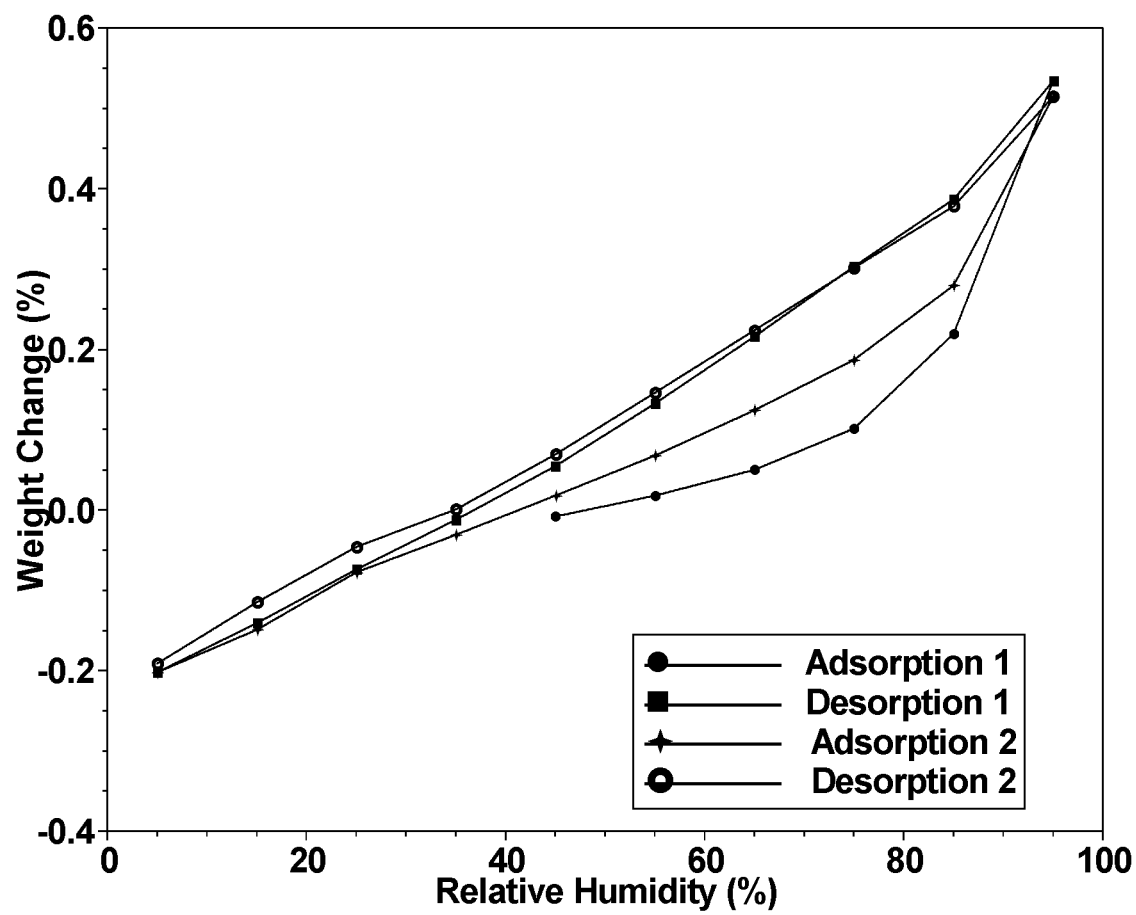
FIG. 4 is a dynamic vapor sorption (DVS) curve of Compound I Form I.

In some embodiments, Compound I Form I can be characterized by a differential scanning calorimetry (DSC) curve comprising an endotherm having an onset temperature of about 253° C. The endotherm can comprise a peak at about 256° C. In another embodiment, Compound I Form I can be characterized by a DSC curve substantially as shown in FIG. 2. In some embodiments, Compound I Form I can be characterized by thermogravimetric analysis (TGA) curve substantially as shown in FIG. 3. In some embodiments, Compound I Form I can be characterized by a dynamic vapor sorption (DVS) curve substantially as shown in FIG. 4. As can be determined from FIG. 4, Compound I Form I can be slightly hygroscopic, absorbing up to about 0.8 wt. % water at 25° C. and 95% RH. Compound I Form I is a monoclinic crystalline form having unit cell parameters: a equal to 8.62 Å, b equal to 19.71 Å, c equal to 13.46 Å, α equal to 90°, β equal to 108.34° and γ equal to 90°.

Compound I Form II

Figure 5:
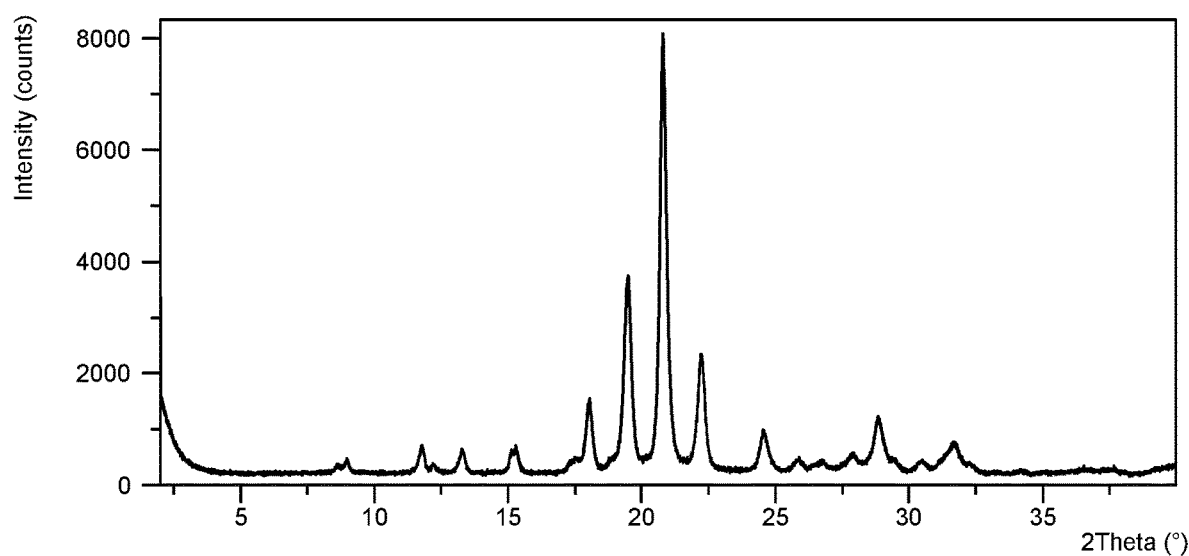
FIG. 5 is an X-ray powder diffractogram of Compound I Form II.

Compound I Form II can be characterized by an X-ray powder diffractogram comprising peaks (±0.2° 2θ) at 19.5, 20.8 and 22.2° 2θ, as determined on a diffractometer using Cu-Kα radiation. The diffractogram can comprise additional peaks (±0.2° 2θ) at 18.1, 24.5 and 28.9° 2θ. Compound I Form II can be characterized by an X-ray powder diffractogram as substantially shown in FIG. 5. In one embodiment, Compound I Form II can be characterized by an X-ray powder diffractogram comprising at least three, at least four or at least five peaks (±0.2° 2θ) selected from 20.8, 19.5, 22.2, 18.1, 28.9, 24.5, 31.7, 11.8 and 15.3° 2θ, as determined on a diffractometer using Cu-Kα radiation.

Figure 6:
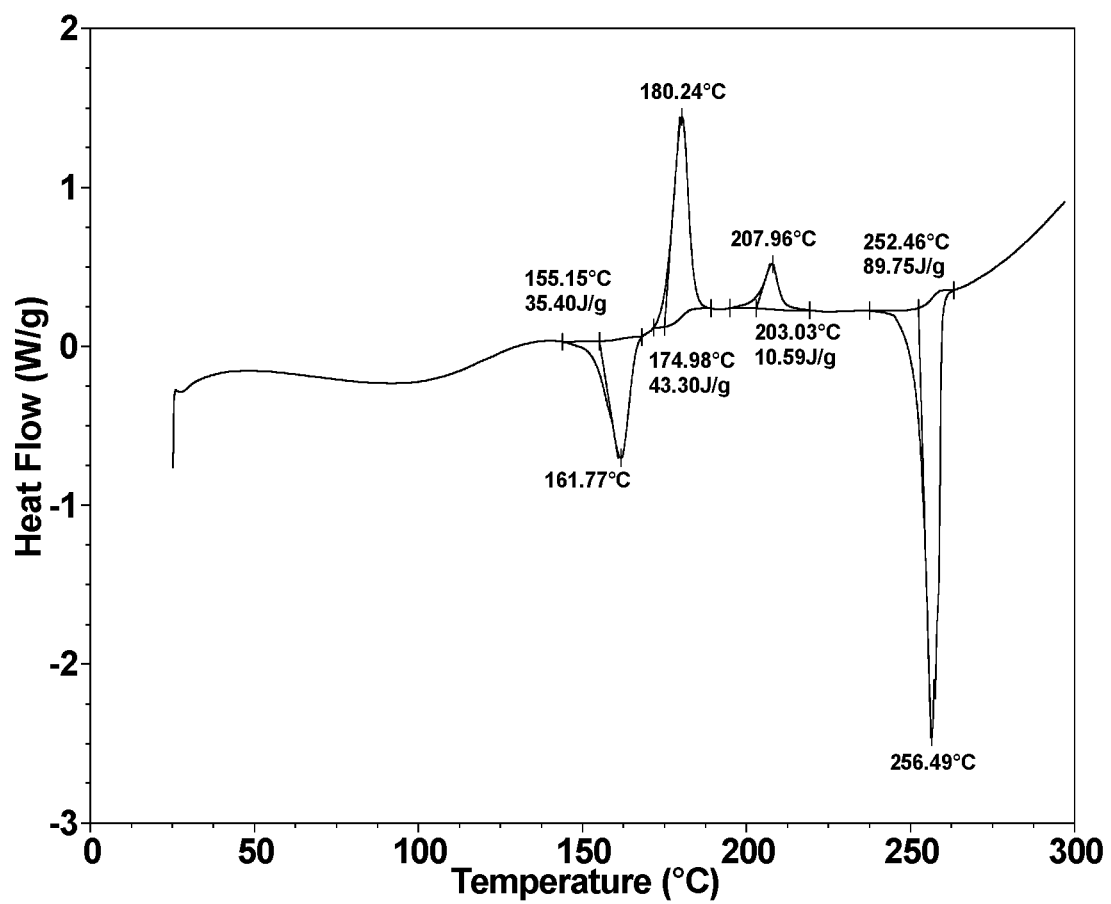
FIG. 6 is a DSC curve of Compound I Form II.
Figure 7:
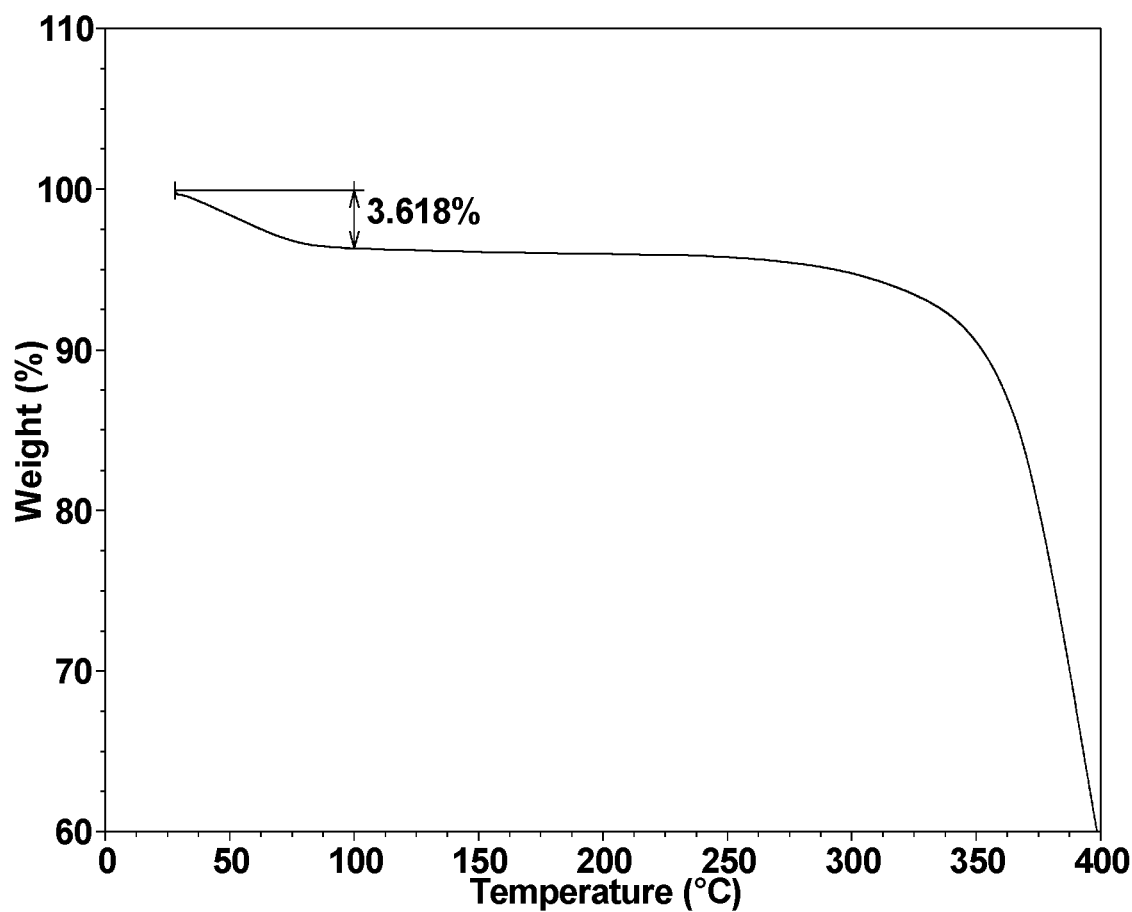
FIG. 7 is a TGA curve of Compound I Form II.
Figure 8:
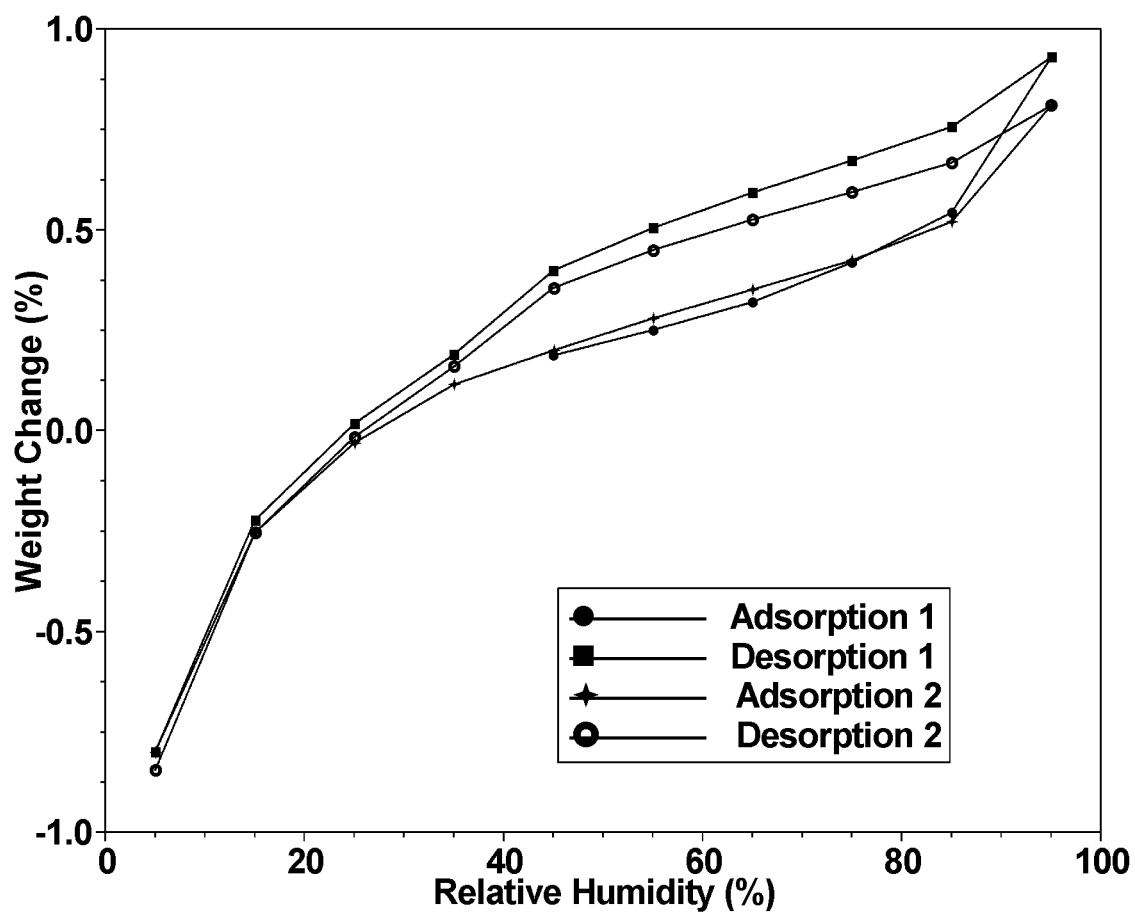
FIG. 8 is a DVS curve of Compound I Form II.

In some embodiments, Compound I Form II can be characterized by a DSC curve comprising endotherms having onset temperatures of about 155° C. and 253° C. The endotherms can comprise peaks at about 162° C. and 257° C. In another embodiment, Compound I Form II can be characterized by a DSC curve substantially as shown in FIG. 6. In some embodiments, Compound I Form II can be characterized by a TGA curve substantially as shown in FIG. 7. In some embodiments, Compound I Form II can be characterized by a DVS curve substantially as shown in FIG. 8. DVS analysis shows that it is slightly hygroscopic, absorbing up to about 2 wt. % water at 25° C. and 95% RH.

Compound I Form III

Figure 9:
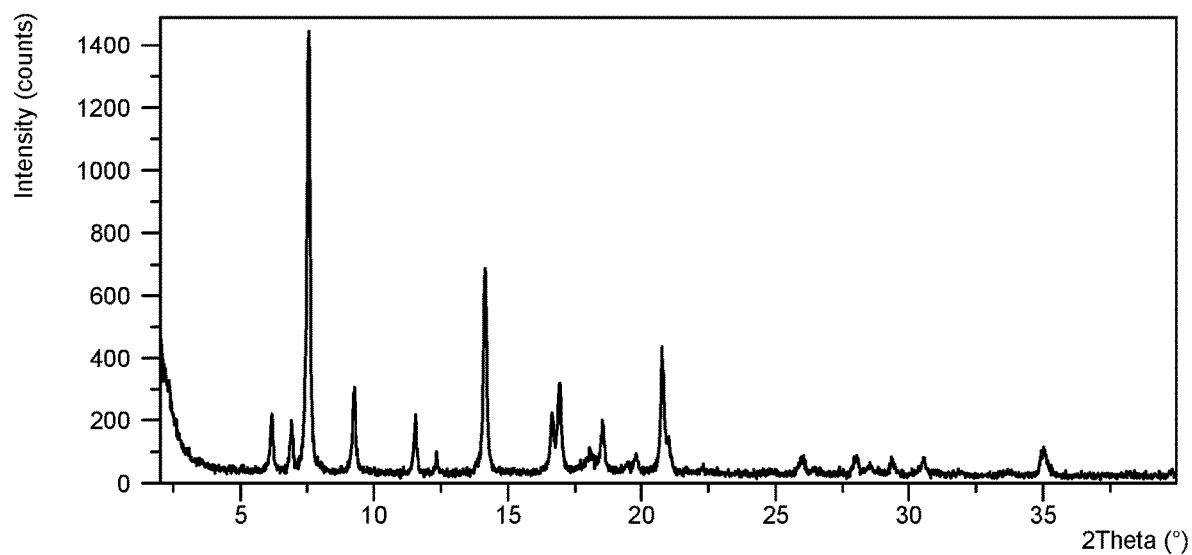
FIG. 9 is an X-ray powder diffractogram of Compound I Form III.

Compound I Form III is a hydrated form. Compound I Form III can be characterized by an X-ray powder diffractogram comprising peaks (±0.2° 2θ) at 7.6, 14.2 and 20.8° 2θ, as determined on a diffractometer using Cu-Kα radiation. The diffractogram can comprise additional peaks (±0.2° 2θ) at 6.2, 9.3 and 16.9° 2θ. Compound I Form III can be characterized by an X-ray powder diffractogram as substantially shown in FIG. 9. In one embodiment, Compound I Form III can be characterized by an X-ray powder diffractogram comprising at least three, at least four or at least five peaks (±0.2° 2θ) selected from 7.6, 14.2, 20.8, 16.9, 9.3, 6.2, 16.7, 11.5 and 6.9° 2θ, as determined on a diffractometer using Cu-Kα radiation.

Figure 10:
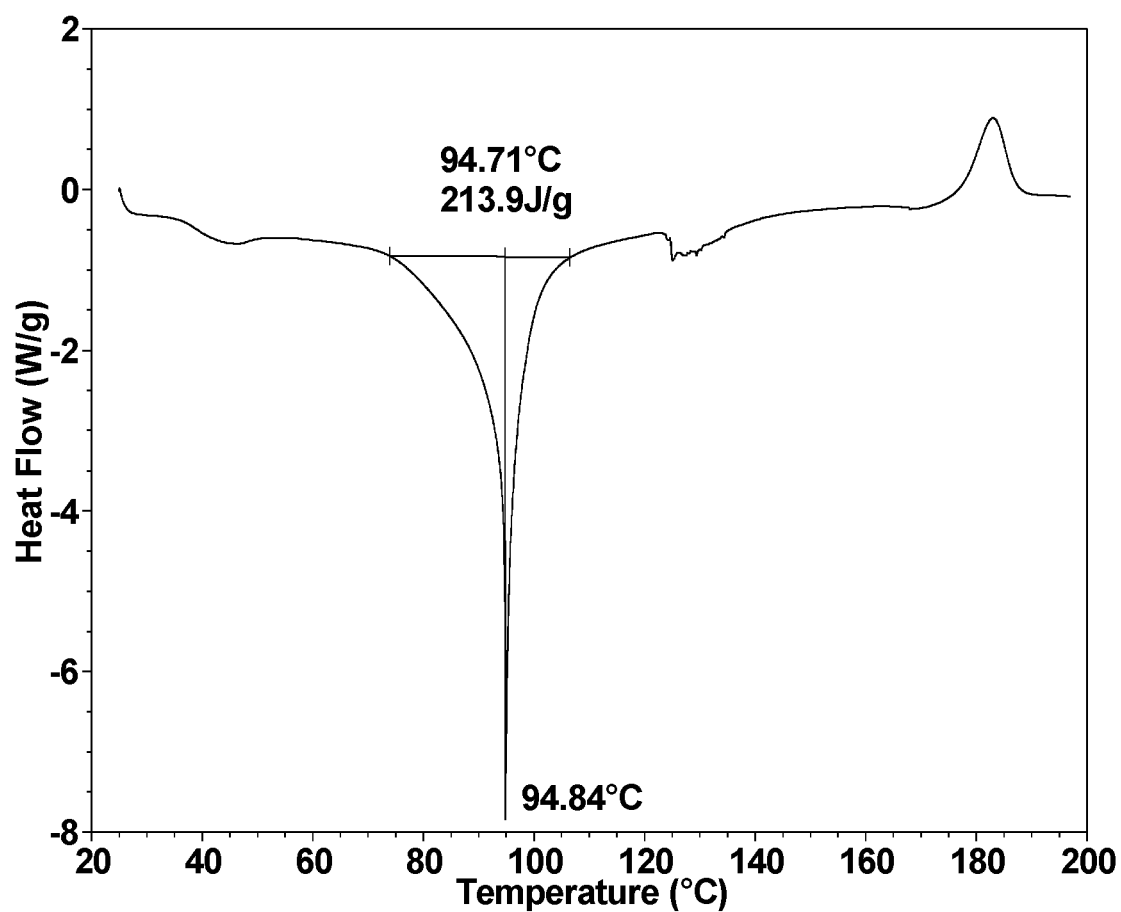
FIG. 10 is a DSC curve of Compound I Form III.
Figure 11:
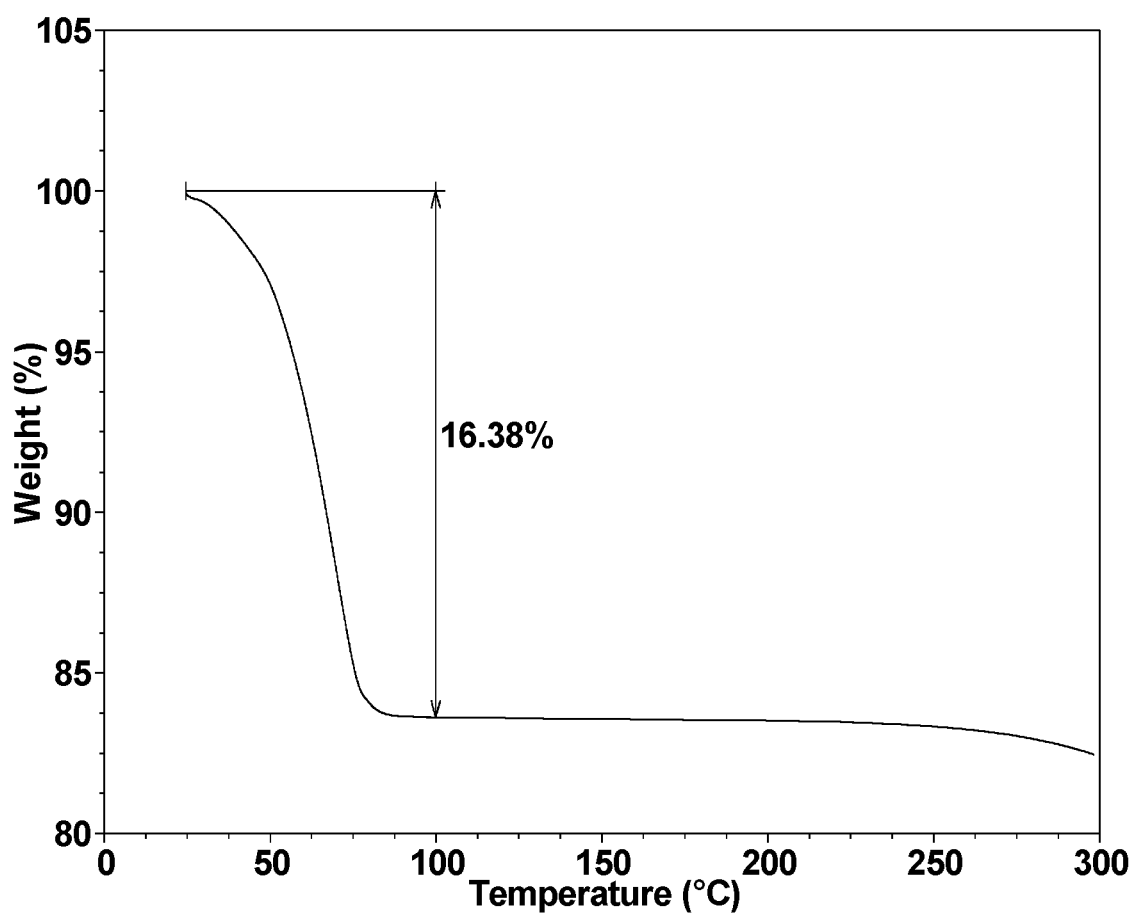
FIG. 11 is a TGA curve of Compound I Form III.

In some embodiments, Compound I Form III can be characterized by a DSC curve comprising an endotherm having an onset temperature and a peak at about 95° C. In another embodiment, Compound I Form III can be characterized by a DSC curve substantially as shown in FIG. 10. In some embodiments, Compound I Form III can be characterized by a TGA curve substantially as shown in FIG. 11.

Compound I Form IV

Compound I Form IV is a mono-methanol solvate. Compound I Form IV can be characterized by a calculated X-ray powder diffractogram comprising peaks (±0.2° 2θ) at 19.2, 20.9 and 21.4° 2θ. The diffractogram can comprise additional peaks (±0.2° 2θ) at 8.7, 17.4 and 19.6° 2θ. Compound I Form IV can be characterized by an X-ray powder diffractogram as substantially shown in FIG. 73. In one embodiment, Compound I Form IV can be characterized by an X-ray powder diffractogram comprising at least three, at least four or at least five peaks (±0.2° 2θ) selected from 21.4, 20.9, 19.2, 19.6, 8.7, 17.4, 11.4, 15.3 and 12.1° 2θ, as determined on a diffractometer using Cu-Kα radiation.

Compound I Form IV is a monoclinic crystalline form having unit cell parameters: a equal to 14.29 Å, b equal to 14.57 Å, c equal to 11.57 Å, α equal to 90°, β equal to 92.41° and γ equal to 90°.

Compound I Form V

Figure 12:
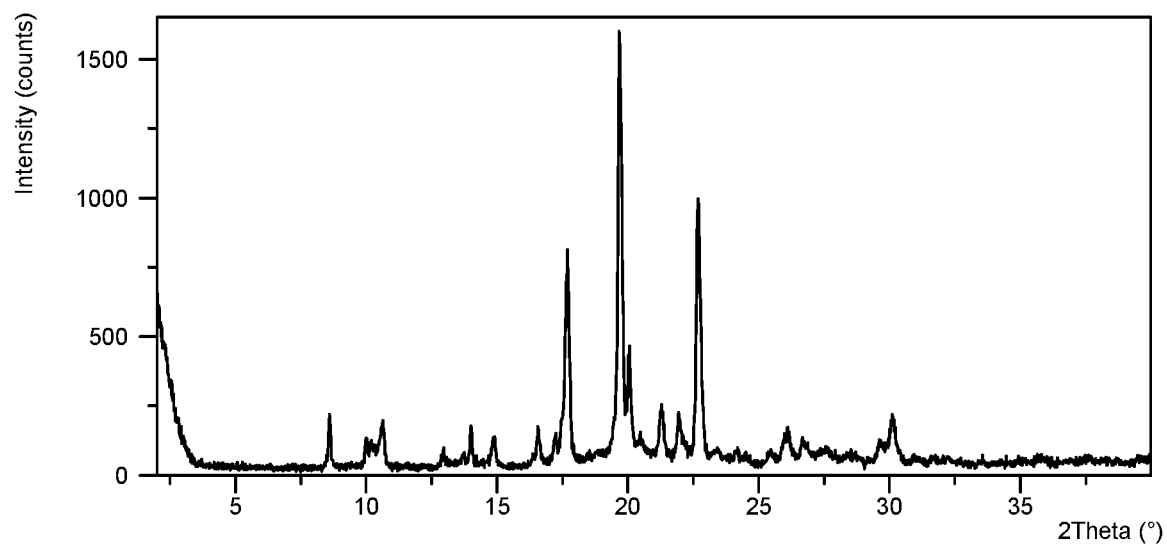
FIG. 12 is an X-ray powder diffractogram of Compound I Form V.

Compound I Form V is a monohydrate. Compound I Form V can be characterized by an X-ray powder diffractogram comprising peaks (±0.2° 2θ) at 17.7, 19.7 and 22.7° 2θ, as determined on a diffractometer using Cu-Kα radiation. The diffractogram can comprise additional peaks (±0.2° 2θ) at 8.6, 14.0 and 20.0° 2θ. Compound I Form V can be characterized by an X-ray powder diffractogram as substantially shown in FIG. 12. In one embodiment, Compound I Form V can be characterized by an X-ray powder diffractogram comprising at least three, at least four or at least five peaks (±0.2° 2θ) selected from 19.7, 22.7, 17.7, 14.0, 20.0, 8.6, 14.9, 21.3 and 17.2° 2θ, as determined on a diffractometer using Cu-Kα radiation.

Figure 13:
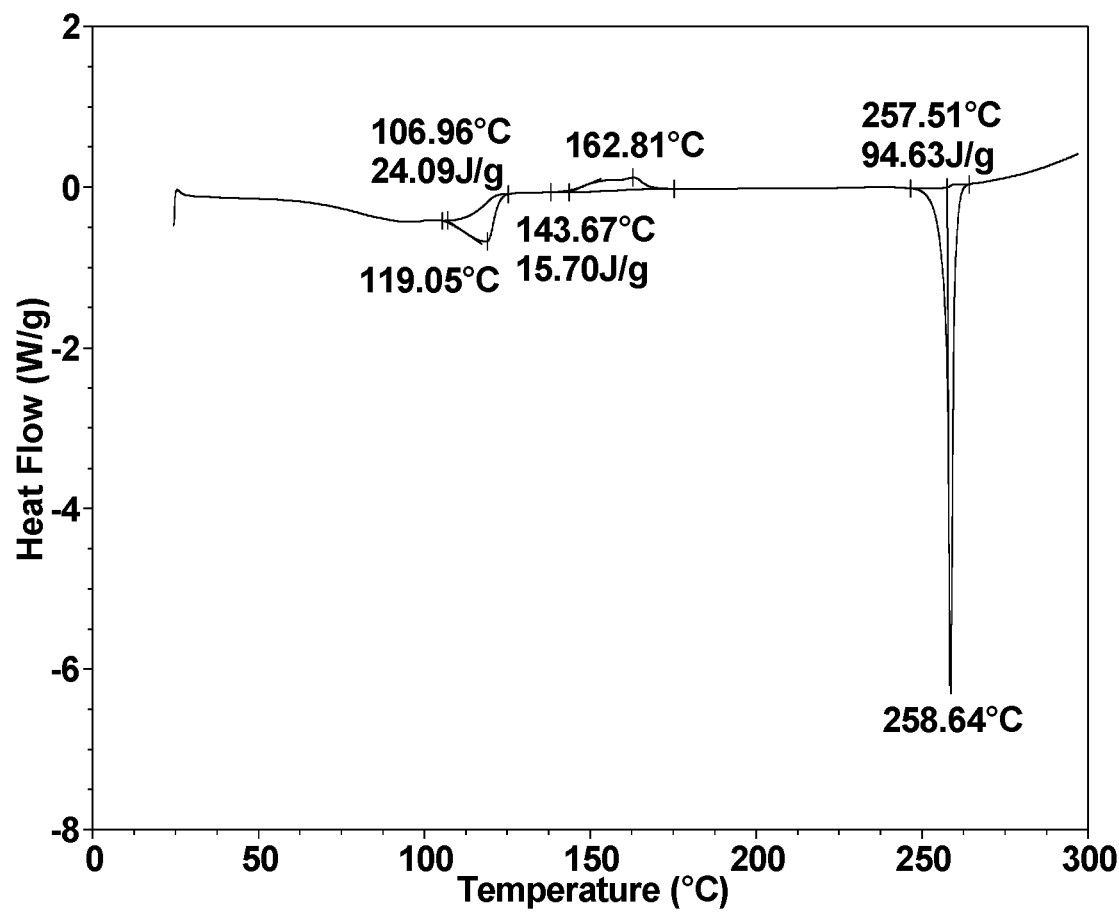
FIG. 13 is a DSC curve of Compound I Form V.
Figure 14:
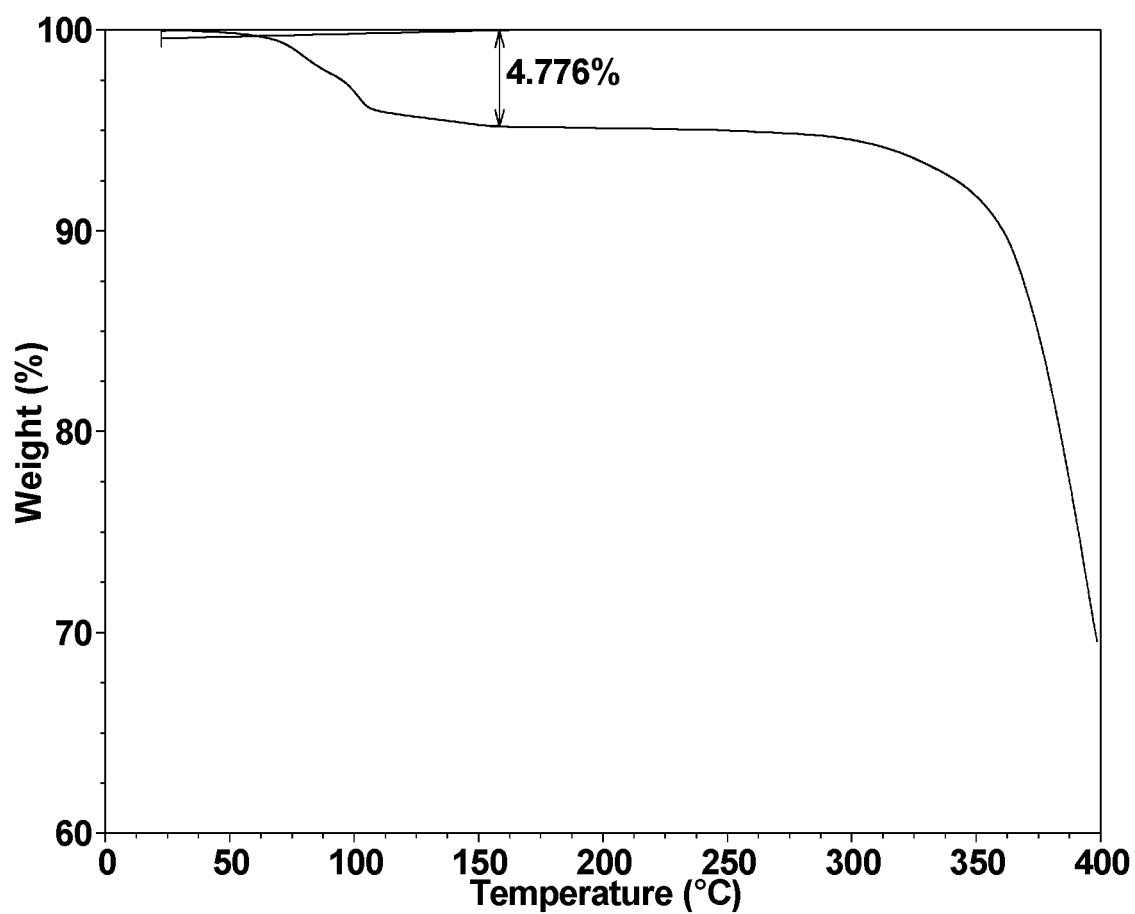
FIG. 14 is a TGA curve of Compound I Form V.
Figure 15:
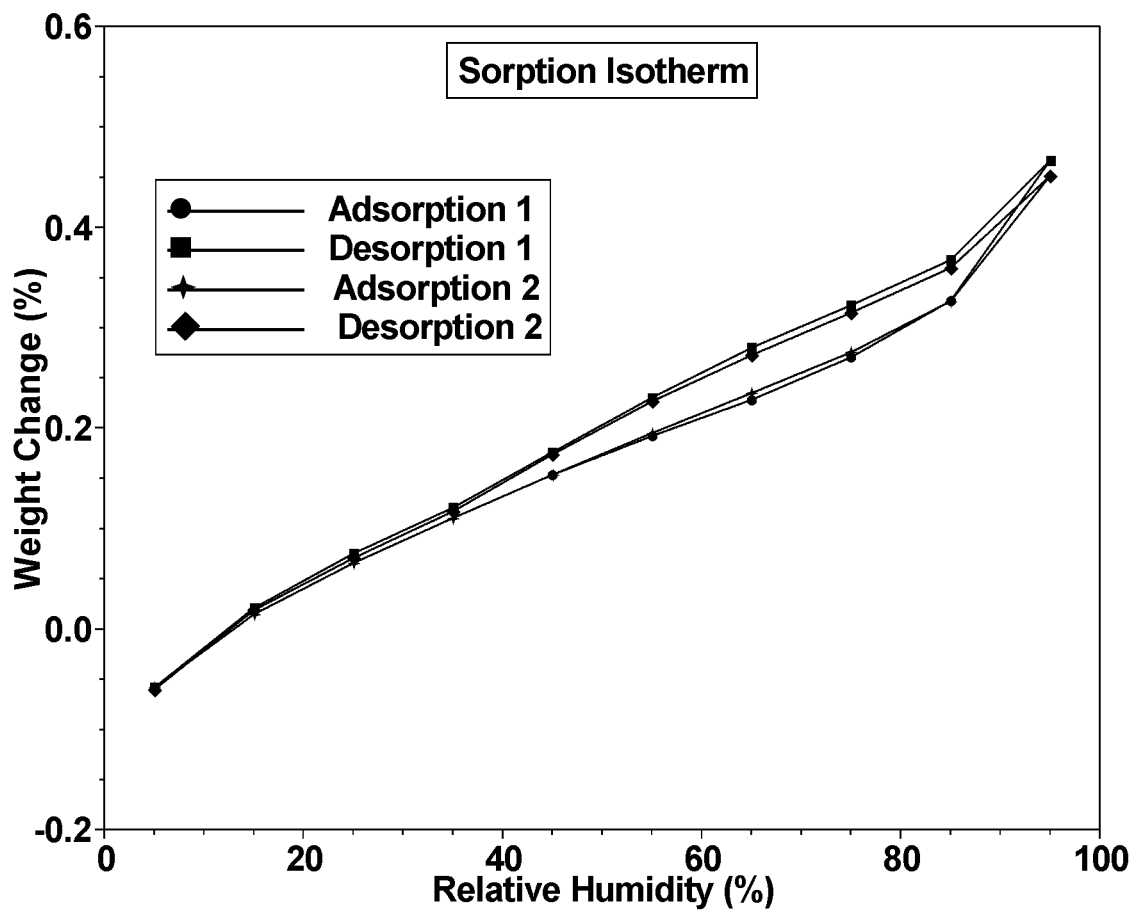
FIG. 15 is a DVS curve of Compound I Form V.

In some embodiments, Compound I Form V can be characterized by a DSC curve comprising an endotherm having an onset temperature of about 117° C. and 258° C. The endotherms comprise peaks at about 119° C. and 256° C. In another embodiment, Compound I Form V can be characterized by a DSC curve substantially as shown in FIG. 13. In some embodiments, Compound I Form V can be characterized by a TGA curve substantially as shown in FIG. 14. In another embodiment, Compound I Form V can be characterized by a DVS curve substantially as shown in FIG. 15. As can be determined from FIG. 15, Compound I Form V can be slightly hygroscopic, absorbing up to about 0.5 wt. % water at 25° C. and 95% RH Compound I Form V is a monoclinic crystalline form having unit cell parameters: a equal to 10.55 Å, b equal to 17.75 Å, c equal to 13.33 Å, a equal to 90°, β equal to 108.3° and γ equal to 90°. When heated to about 150° C., Compound I Form V dehydrates to Compound I Form I.

Compound I Form VI

Compound I Form VI is a mono-ethanol solvate. Compound I Form VI can be characterized by a calculated X-ray powder diffractogram comprising peaks (±0.2° 2θ) at 18.9, 20.4 and 21.0° 2θ. The diffractogram can comprise additional peaks (±0.2° 2θ) at 8.5, 19.3 and 25.1° 2θ. Compound I Form VI can be characterized by an X-ray powder diffractogram as substantially shown in FIG. 74. In one embodiment, Compound I Form VI can be characterized by an X-ray powder diffractogram comprising at least three, at least four or at least five peaks (±0.2° 2θ) selected from 21.0, 20.4, 18.9, 19.3, 8.5, 25.1, 11.3, 15.3 and 17.0° 2θ, as determined on a diffractometer using Cu-Kα radiation.

Figure 16:
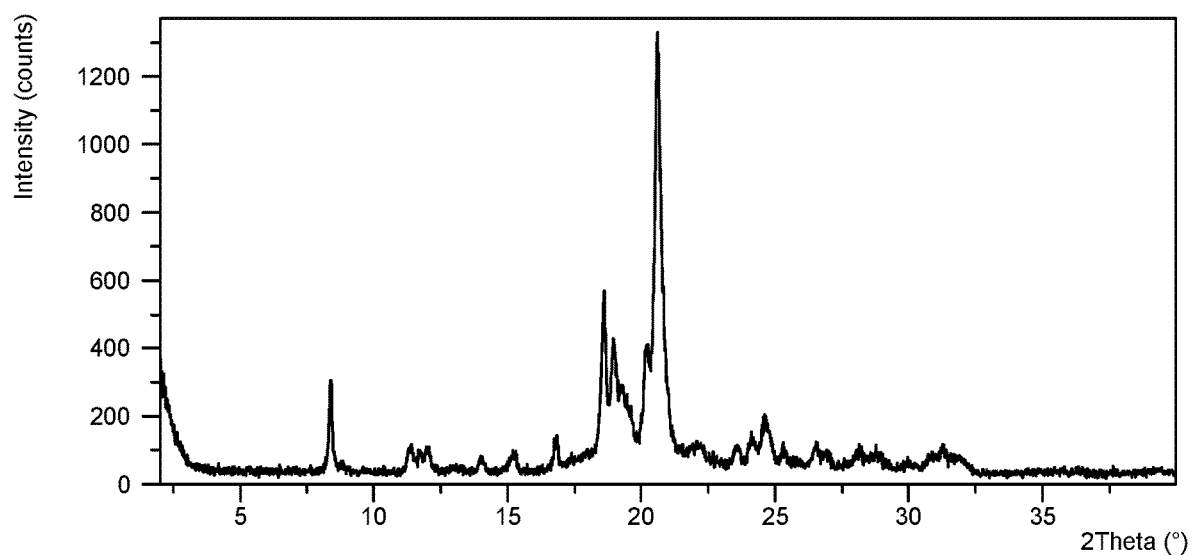
FIG. 16 is an X-ray powder diffractogram of Compound I Form VII.

Compound I Form VI is a monoclinic crystalline form having unit cell parameters: a equal to 14.52 Å, b equal to 14.91 Å, c equal to 11.58 Å, α equal to 90°, β equal to 91.82° and γ equal to 90°. When heated to elevated temperatures, Compound I Form VI desolvates to Compound I Form I Compound I Form VII Compound I Form VII is an isopropanol solvate. Compound I Form VII can be characterized by an X-ray powder diffractogram comprising peaks (±0.2° 2θ) at 8.4, 18.6 and 20.6° 2θ, as determined on a diffractometer using Cu-Kα radiation. The diffractogram can comprise additional peaks (±0.2° 2θ) at 19.0, 20.2 and 24.6° 2θ. Compound I Form VII can be characterized by an X-ray powder diffractogram as substantially shown in FIG. 16. In one embodiment, Compound I Form VII can be characterized by an X-ray powder diffractogram comprising at least three, at least four or at least five peaks (±0.2° 2θ) selected from 20.6, 18.6, 20.2, 19.0, 8.4, 24.6, 16.8, 22.1 and 24.1° 2θ, as determined on a diffractometer using Cu-Kα radiation.

Figure 17:
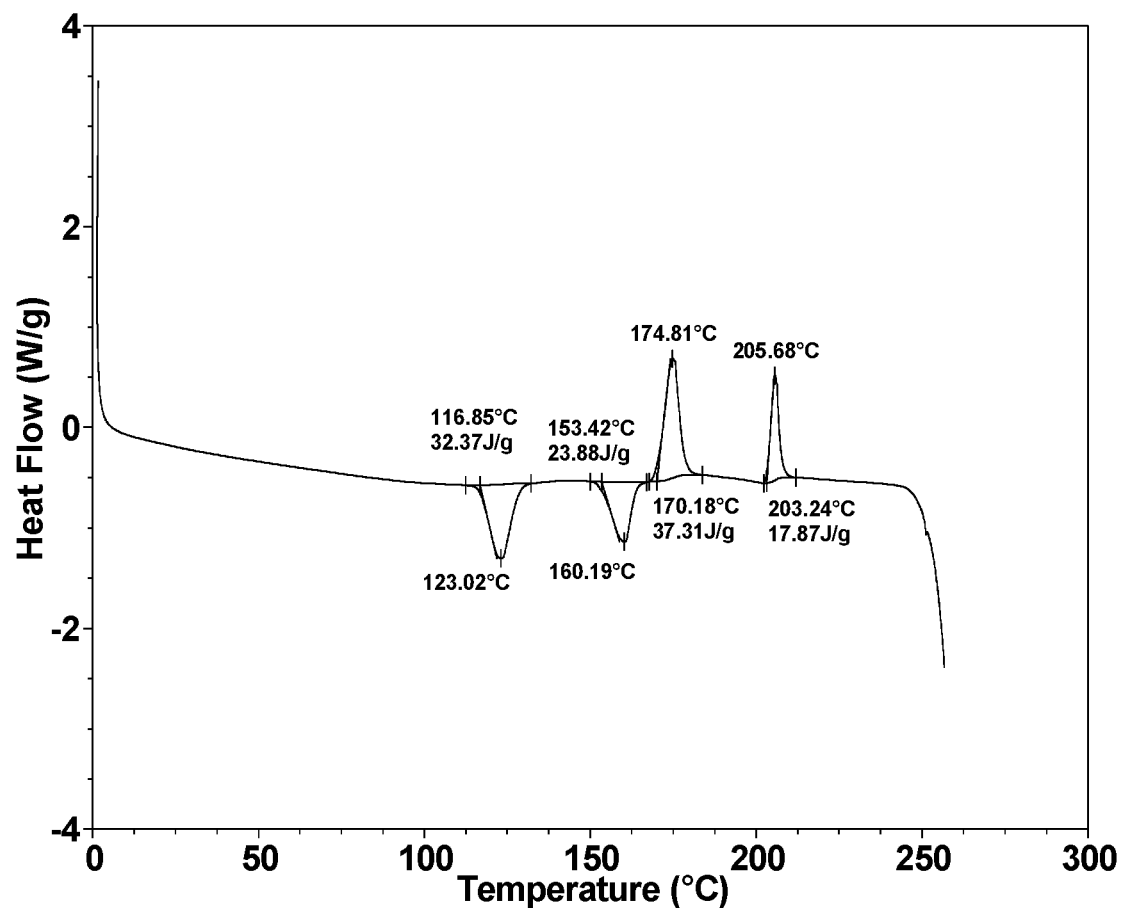
FIG. 17 is a DSC curve of Compound I Form VII.
Figure 18:
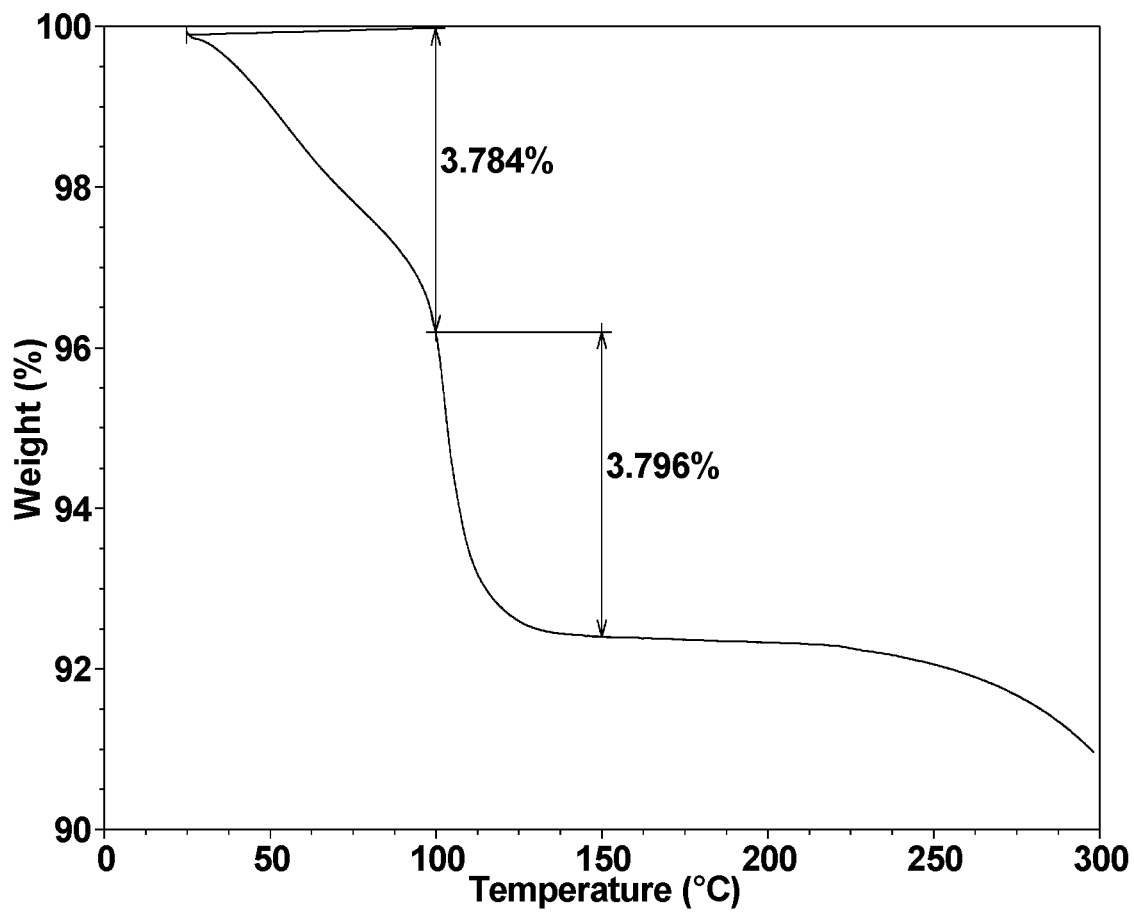
FIG. 18 is a TGA curve of Compound I Form VII.

In some embodiments, Compound I Form VII can be characterized by a differential scanning calorimetry (DSC) curve comprising endotherms having onset temperatures of about 117° C. and 153° C. The endotherms comprise a peak at about 123° C. and 160° C. In another embodiment, Compound I Form VII can be characterized by a DSC curve substantially as shown in FIG. 17. In some embodiments, Compound I Form VII can be characterized by a TGA curve substantially as shown in FIG. 18. When heated to about 100° C., Compound I Form VII desolvates to Compound I Form II.

Compound I Form VIII

Figure 19:
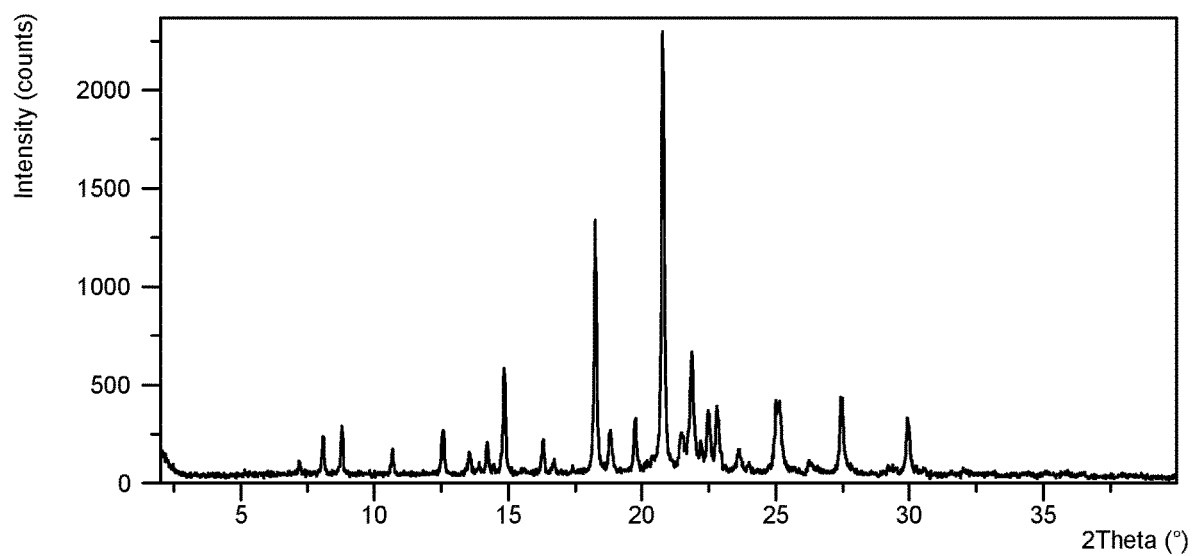
FIG. 19 is an X-ray powder diffractogram of Compound I Form VIII.

Compound I Form VIII is a DMF solvate. Compound I Form VIII can be characterized by an X-ray powder diffractogram comprising peaks (±0.2° 2θ) at 18.3, 20.8 and 21.9° 2θ, as determined on a diffractometer using Cu-Kα radiation. The diffractogram can comprise additional peaks (±0.2° 2θ) at 14.8, 25.0 and 27.4° 2θ. Compound I Form VIII can be characterized by an X-ray powder diffractogram as substantially shown in FIG. 19. In one embodiment, Compound I Form VIII can be characterized by an X-ray powder diffractogram comprising at least three, at least four or at least five peaks (±0.2° 2θ) selected from 20.8, 18.3, 21.9, 14.8, 27.4, 25.0, 22.8, 25.2 and 22.5° 2θ, as determined on a diffractometer using Cu-Kα radiation.

Figure 20:
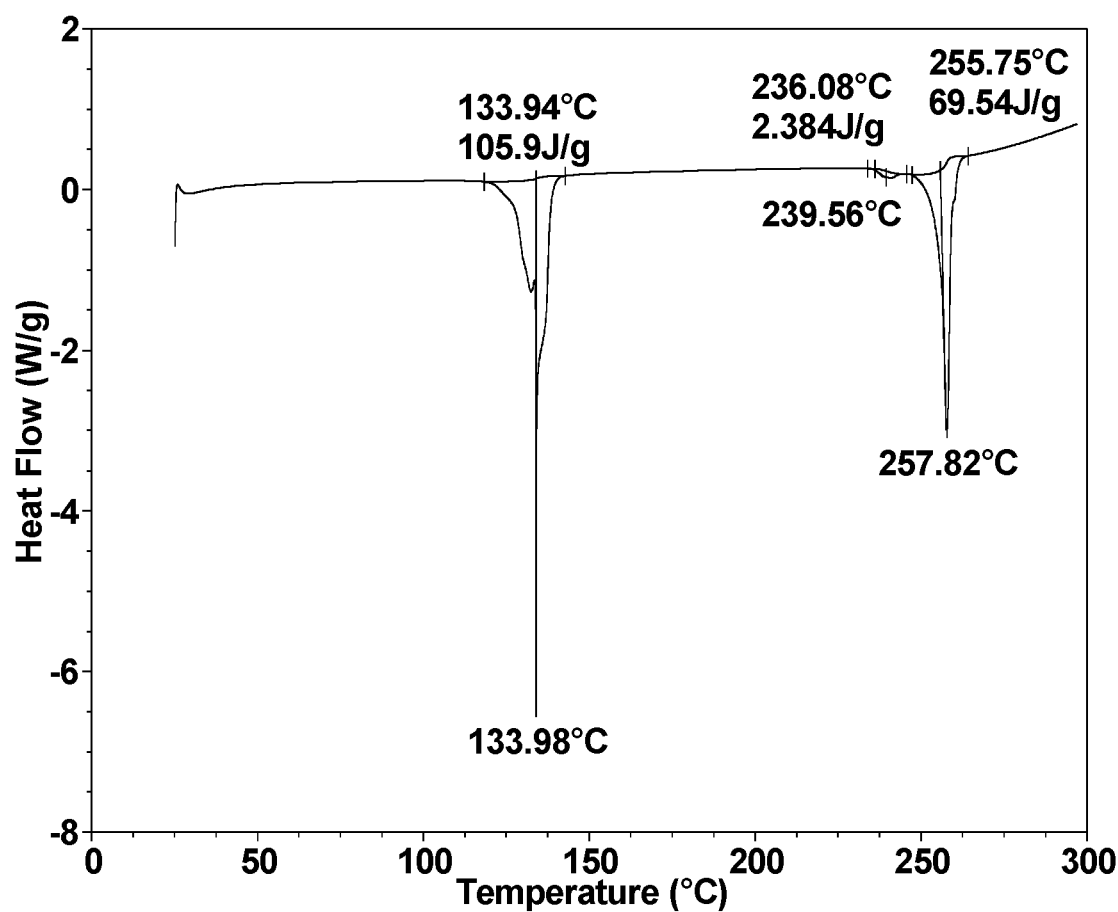
FIG. 20 is a DSC curve of Compound I Form VIII.
Figure 21:
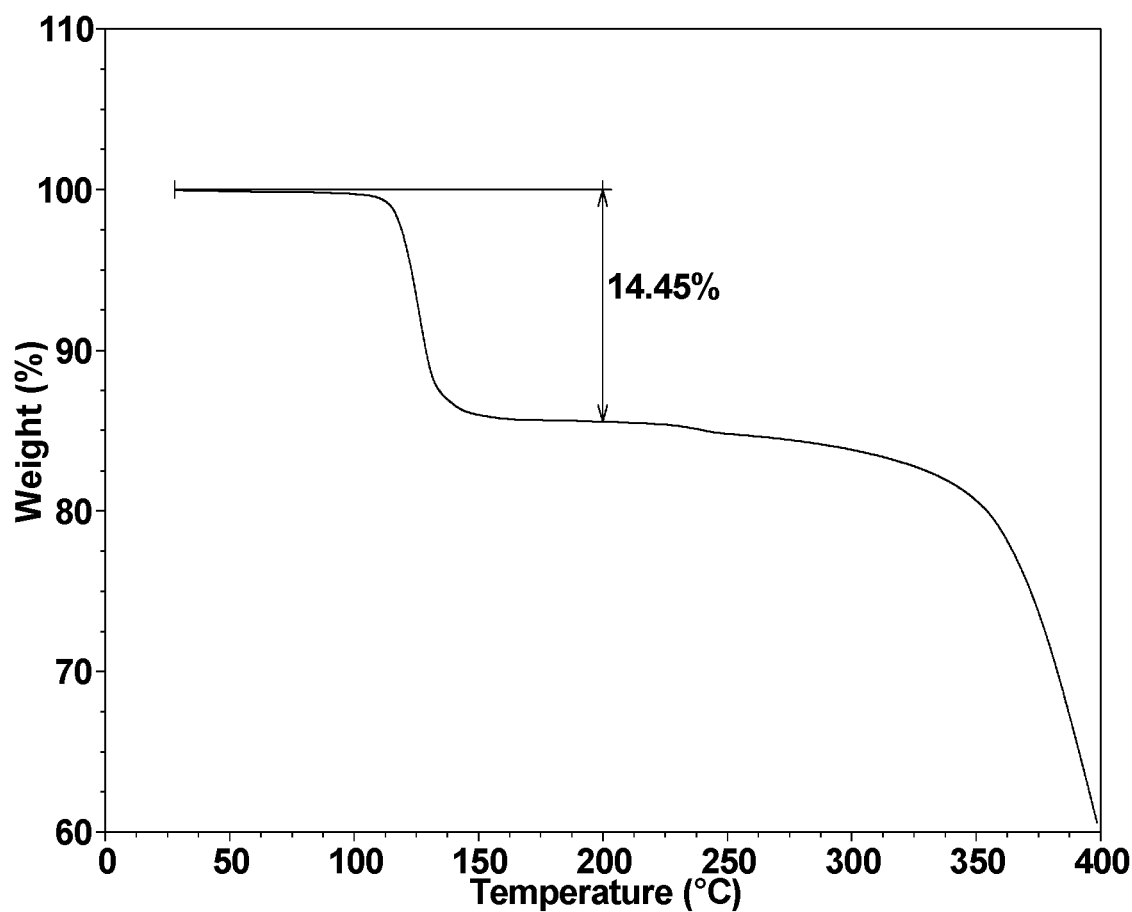
FIG. 21 is a TGA curve of Compound I Form VIII.

In some embodiments, Compound I Form VIII can be characterized by a DSC curve comprising endotherms having onset temperatures of about 133° C., 236° C. and 256° C. The endotherms comprise peaks at about 134° C., 240° C. and 258° C. In another embodiment, Compound I Form VIII can be characterized by a DSC curve substantially as shown in FIG. 20. In some embodiments, Compound I Form VIII can be characterized by a TGA curve substantially as shown in FIG. 21. When heated to about 180° C., Compound I Form VIII desolvates to Compound I Form I.

Compound I Form IX

Figure 22:
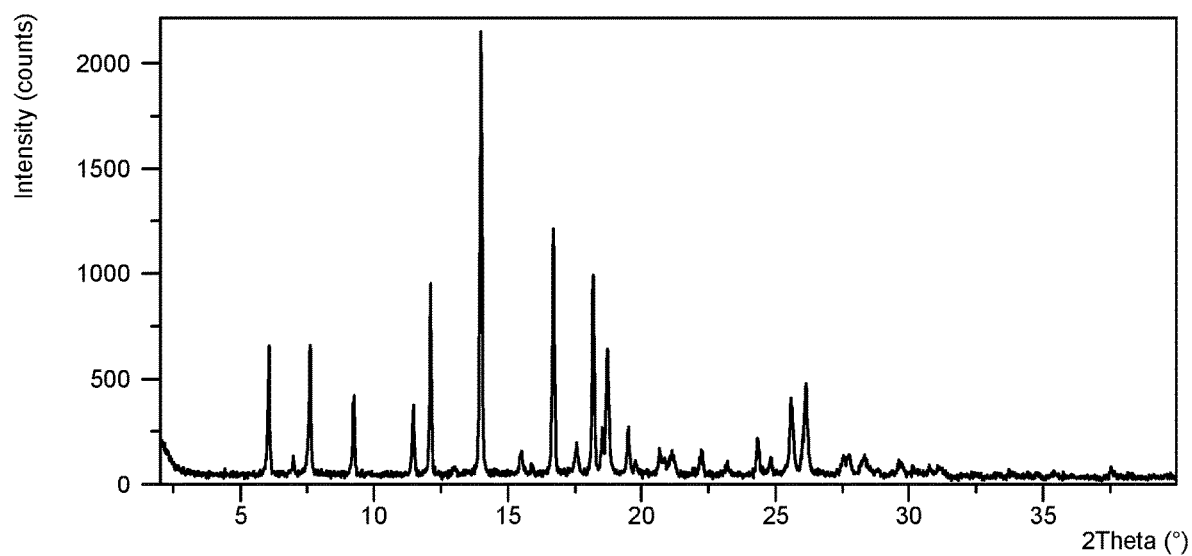
FIG. 22 is an X-ray powder diffractogram of Compound I Form IX.

Compound I Form IX is a tri-hydrate mono-methanolate. Compound I Form IX can be characterized by an X-ray powder diffractogram comprising peaks (±0.2° 2θ) at 14.0, 16.7 and 18.2° 2θ, as determined on a diffractometer using Cu-Kα radiation. The diffractogram can comprise additional peaks (±0.2° 2θ) at 7.6, 12.1 and 18.7° 2θ. Compound I Form IX can be characterized by an X-ray powder diffractogram as substantially shown in FIG. 22. In one embodiment, Compound I Form IX can be characterized by an X-ray powder diffractogram comprising at least three, at least four or at least five peaks (±0.2° 2θ) selected from 14.0, 16.7, 18.2, 12.1, 7.6, 18.7, 6.1, 26.1 and 25.6° 2θ, as determined on a diffractometer using Cu-Kα radiation.

Figure 23:
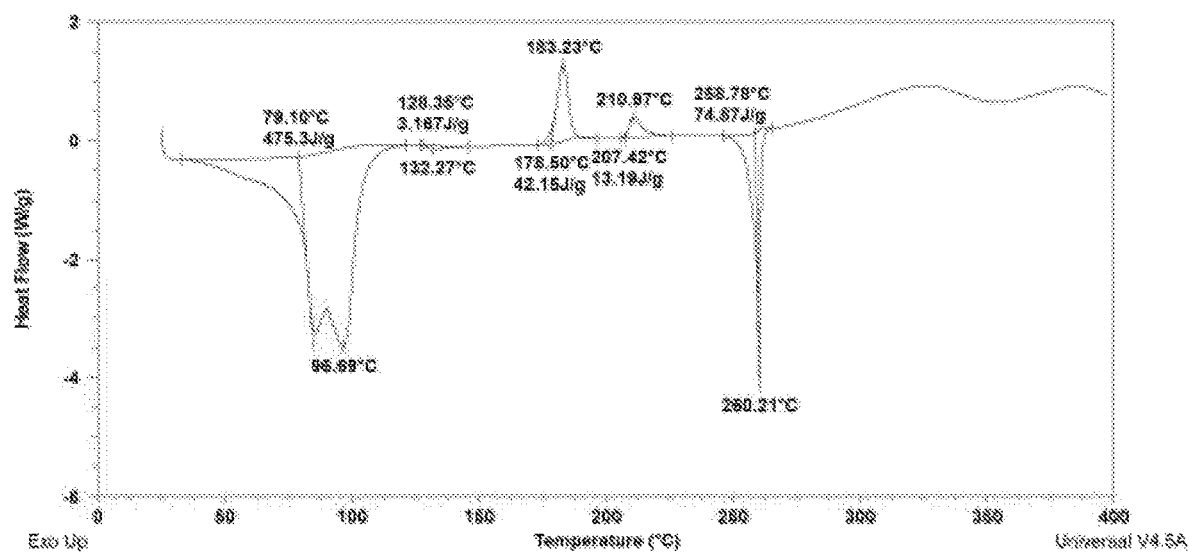
FIG. 23 is a DSC curve of Compound I Form IX.
Figure 24:
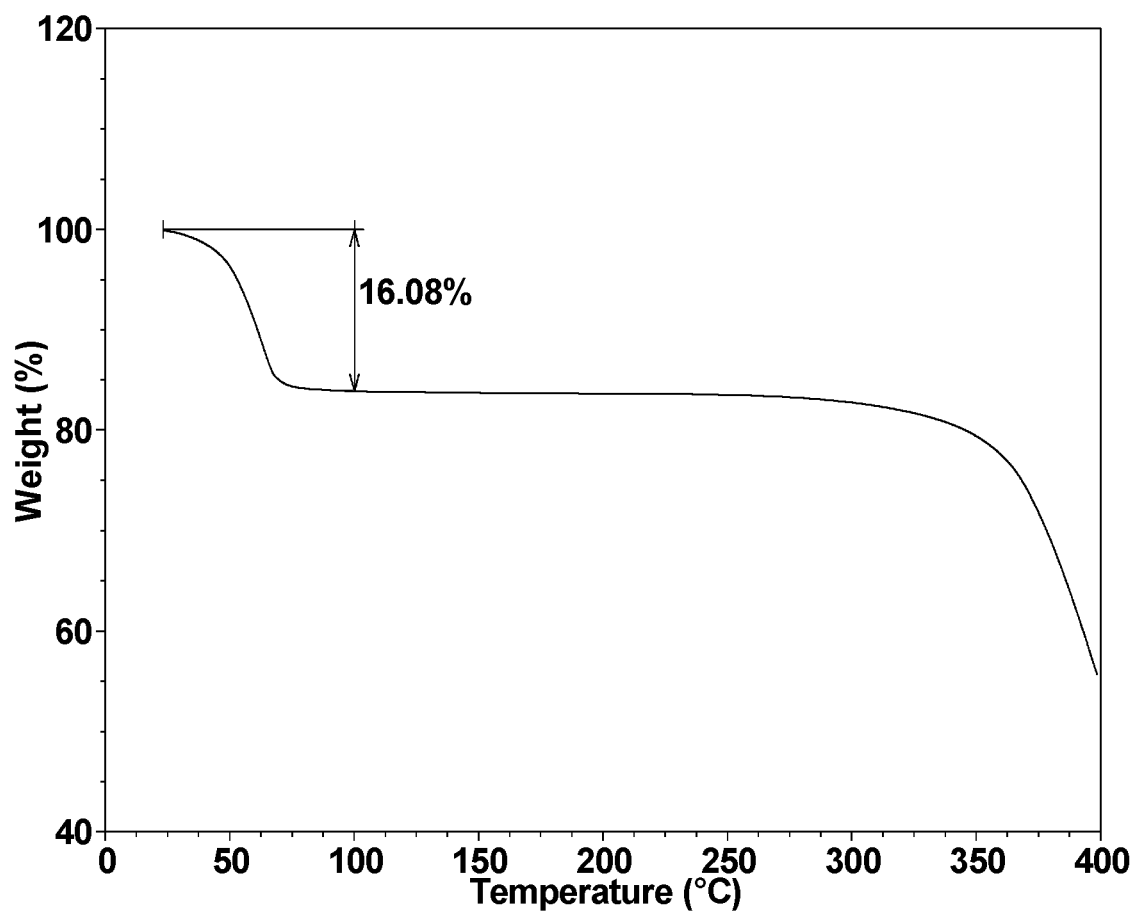
FIG. 24 is a TGA curve of Compound I Form IX.

In some embodiments, Compound I Form IX can be characterized by a differential scanning calorimetry (DSC) curve comprising a broad endotherm between temperatures of about 40° C. and 110° C. In another embodiment, the DSC curve can comprise a further endotherm having an onset temperature of about 259° C. In another embodiment, Compound I Form IX can be characterized by a DSC curve substantially as shown in FIG. 23. In some embodiments, Compound I Form IX can be characterized by a TGA curve substantially as shown in FIG. 24. Compound I Form IX is a monoclinic crystalline form having unit cell parameters: a equal to 6.92 Å, b equal to 28.97 Å, c equal to 12.73 Å, α equal to 90°, β equal to 92.53° and γ equal to 90°. When dried in a vacuum overnight at about 50° C. with a nitrogen purge, Compound I Form IX desolvates to amorphous Compound I.

Compound I Form X

Figure 75:
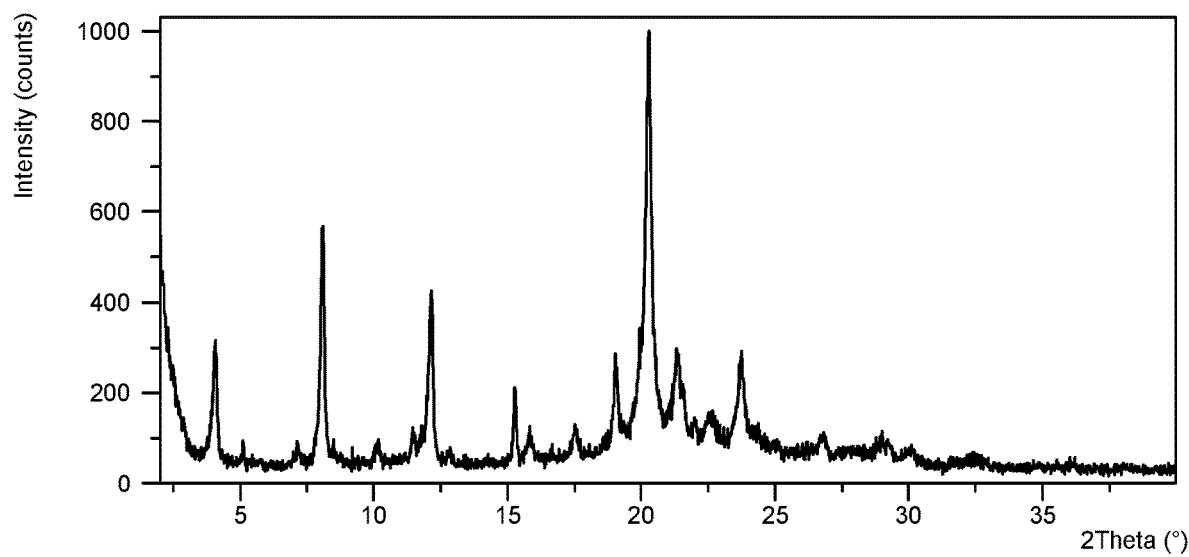
FIG. 75 is an X-ray powder diffractogram of Compound I Form X.

Compound I Form X can be characterized by an X-ray powder diffractogram comprising peaks (±0.2° 2θ) at 8.1, 12.2 and 20.3° 2θ, as determined on a diffractometer using Cu-Kα radiation. The diffractogram can comprise additional peaks (±0.2° 2θ) at 4.1, 19.1 and 21.4° 2θ. Compound I Form X can be characterized by an X-ray powder diffractogram as substantially shown in FIG. 75. In one embodiment, Compound I Form X can be characterized by an X-ray powder diffractogram comprising at least three, at least four or at least five peaks (±0.2° 2θ) selected from 720.3, 8.1, 12.2, 4.1, 21.4, 19.1, 23.7, 15.3 and 22.6° 2θ, as determined on a diffractometer using Cu-Kα radiation.

Compound I Form XI

Figure 76:
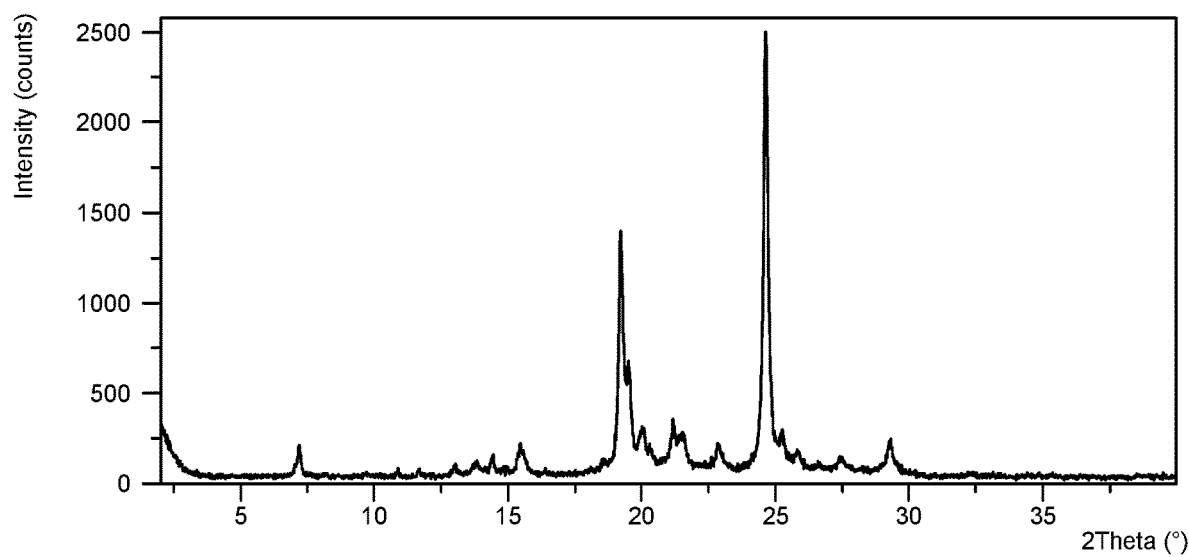
FIG. 76 is an X-ray powder diffractogram of Compound I Form XI.

Compound I Form XI can be characterized by an X-ray powder diffractogram comprising peaks (±0.2° 2θ) at 19.2, 21.2 and 24.6° 2θ, as determined on a diffractometer using Cu-Kα radiation. The diffractogram can comprise additional peaks (±0.2° 2θ) at 19.5, 20.1 and 25.3° 2θ. Compound I Form XI can be characterized by an X-ray powder diffractogram as substantially shown in FIG. 76. In one embodiment, Compound I Form XI can be characterized by an X-ray powder diffractogram comprising at least three, at least four or at least five peaks (±0.2° 2θ) selected from 24.6, 19.2, 21.2, 19.5, 20.1, 25.3, 21.6, 29.3 and 7.2° 2θ, as determined on a diffractometer using Cu-Kα radiation.

Compound I Form XII

Figure 77:
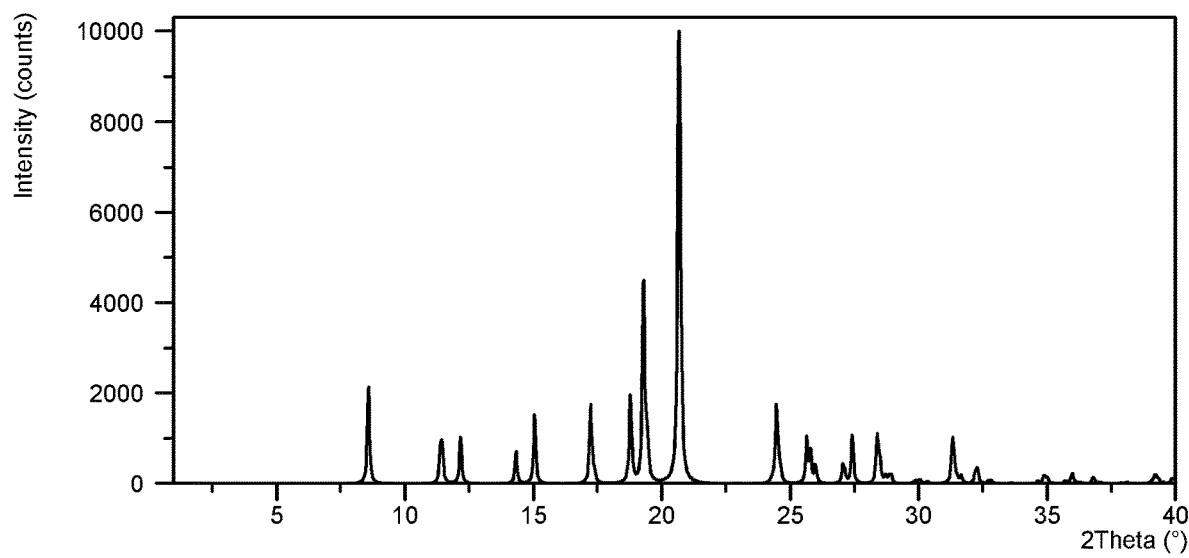
FIG. 77 is a calculated X-ray powder diffractogram of Compound I Form XII.

Compound I Form XII is a mono-acetonitrile solvate. Compound I Form XII can be characterized by a calculated X-ray powder diffractogram comprising peaks (±0.2° 2θ) at 8.6, 19.3 and 20.7° 2θ. The diffractogram can comprise additional peaks (±0.2° 2θ) at 17.2, 18.8 and 24.5° 2θ. Compound I Form XII can be characterized by an X-ray powder diffractogram as substantially shown in FIG. 77. In one embodiment, Compound I Form XII can be characterized by an X-ray powder diffractogram comprising at least three, at least four or at least five peaks (±0.2° 2θ) selected from 20.7, 19.3, 8.6, 18.8, 24.5, 17.2, 15.0, 28.4 and 19.5° 2θ, as determined on a diffractometer using Cu-Kα radiation.

Compound I Form XII is a monoclinic crystalline form having unit cell parameters: a equal to 14.55 Å, b equal to 14.53 Å, c equal to 11.77 Å, α equal to 90°, β equal to 90.46° and γ equal to 90°.

Compound I Form XIII

Figure 25:
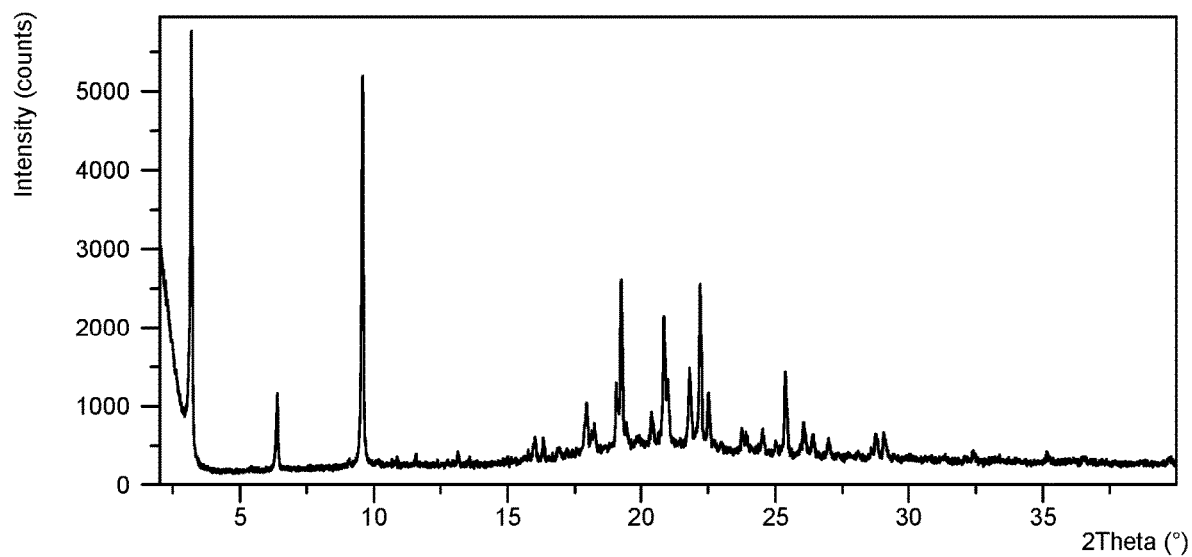
FIG. 25 is an X-ray powder diffractogram of Compound I Form XIII

Compound I Form XIII is a is a propylene glycol solvate. Compound I Form XIII can be characterized by an X-ray powder diffractogram comprising peaks (±0.2° 2θ) at 9.6, 19.3 and 20.8° 2θ, as determined on a diffractometer using Cu-Kα radiation. The diffractogram can comprise additional peaks (±0.2° 2θ) at 21.8, 22.2 and 25.4° 2θ. Compound I Form XIII can be characterized by an X-ray powder diffractogram as substantially shown in FIG. 25. In one embodiment, Compound I Form XIII can be characterized by an X-ray powder diffractogram comprising at least three, at least four or at least five peaks (±0.2° 2θ) selected from 9.6, 19.3, 22.2, 20.8, 21.8, 25.4, 21.0, 19.1 and 6.4° 2θ, as determined on a diffractometer using Cu-Kα radiation.

Compound I Form XIV

Figure 26:
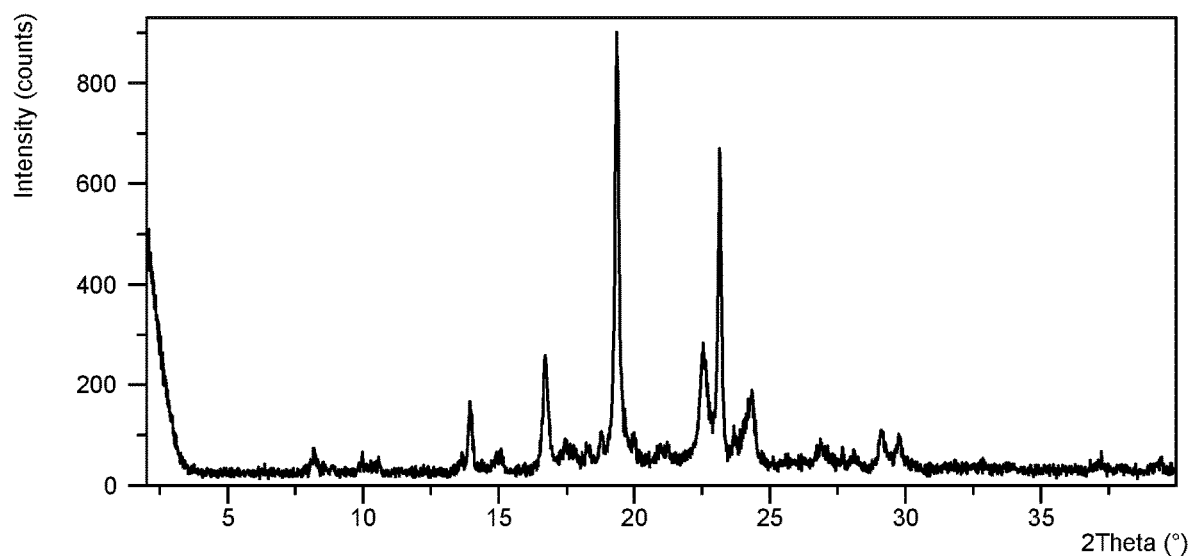
FIG. 26 is an X-ray powder diffractogram of Compound I Form XIV.

Compound I Form XIV can be characterized by an X-ray powder diffractogram comprising peaks (±0.2° 2θ) at 19.4, 22.5 and 23.3° 2θ, as determined on a diffractometer using Cu-Kα radiation. The diffractogram can comprise additional peaks (±0.2° 2θ) at 13.9, 16.7 and 24.3° 2θ. Compound I Form XIV can be characterized by an X-ray powder diffractogram as substantially shown in FIG. 26. In one embodiment, Compound I Form XIV can be characterized by an X-ray powder diffractogram comprising at least three, at least four or at least five peaks (±0.2° 2θ) selected from 19.4, 23.3, 22.5, 16.7, 24.3, 13.9, 18.8, 18.3 and 21.1° 2θ, as determined on a diffractometer using Cu-Kα radiation.

Figure 27:
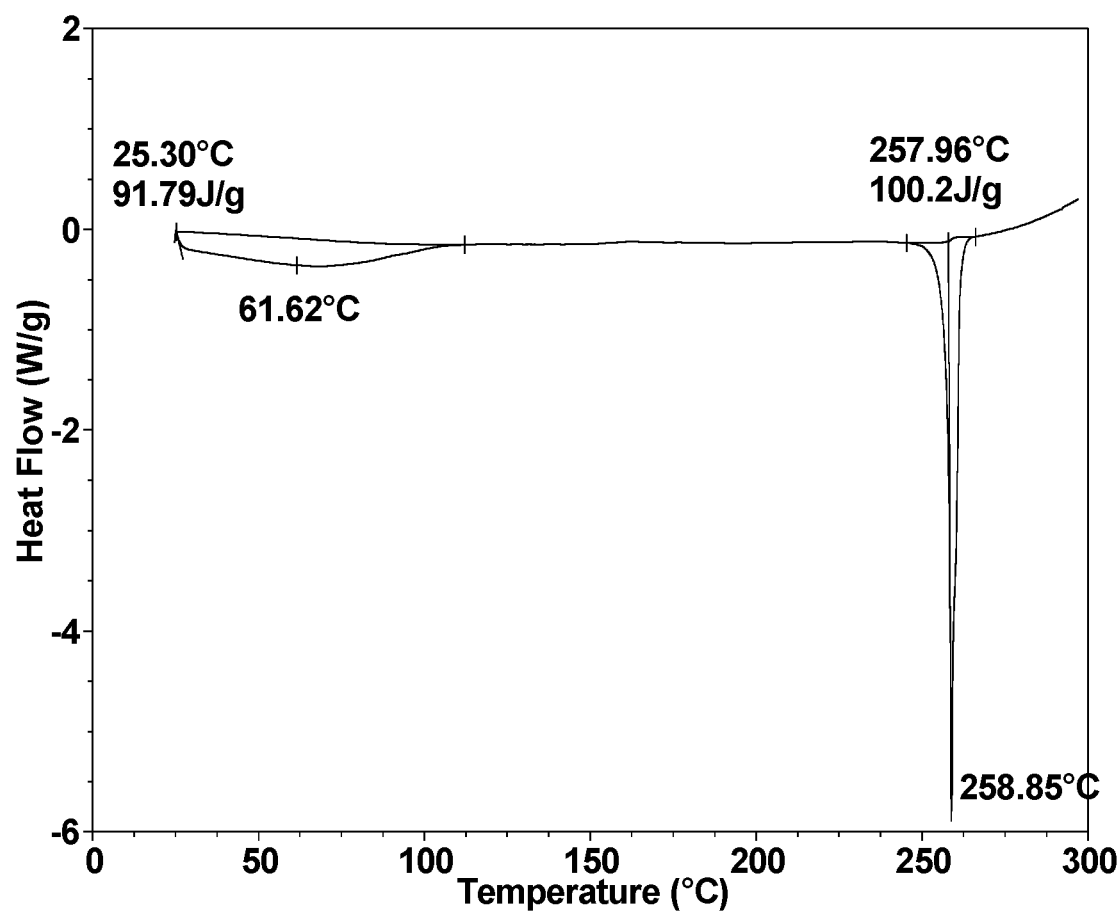
FIG. 27 is a DSC curve of Compound I Form XIV.
Figure 28:
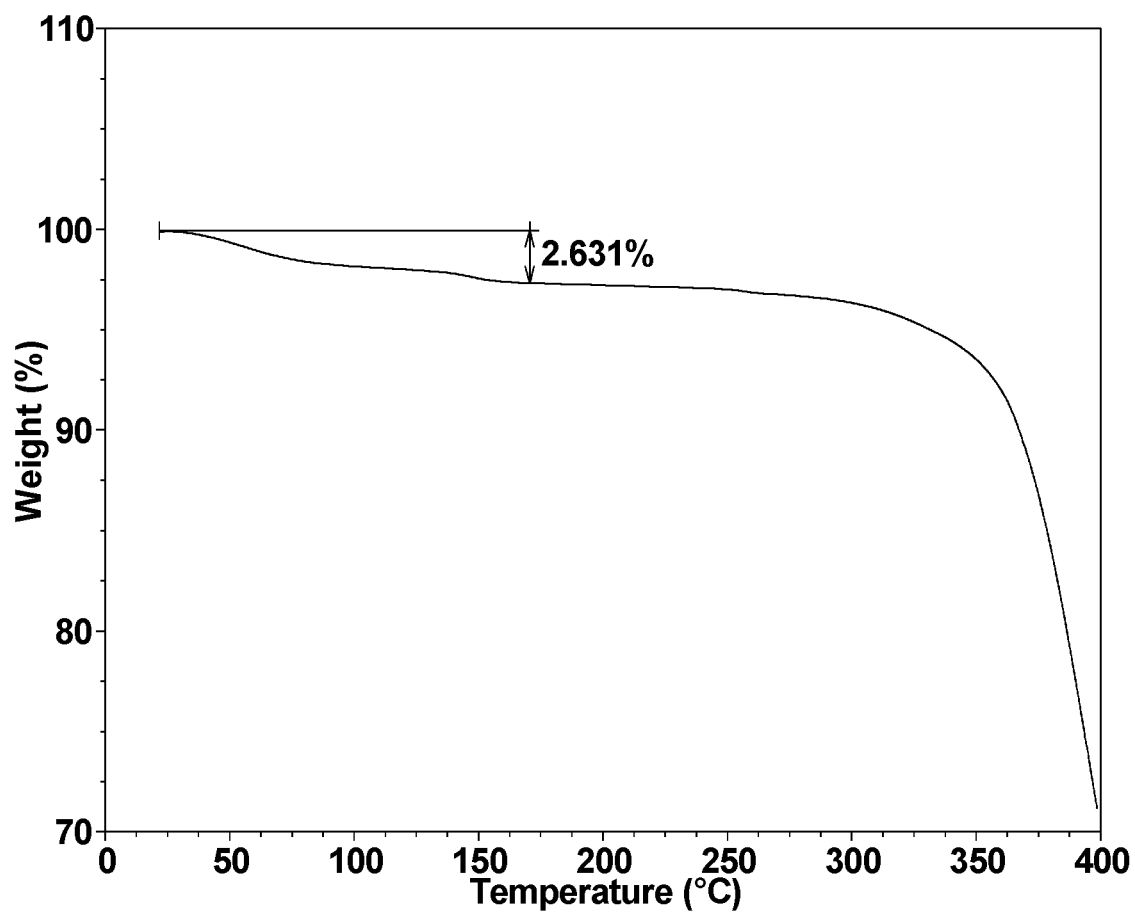
FIG. 28 is a TGA curve of Compound I Form XIV.
Figure 29:
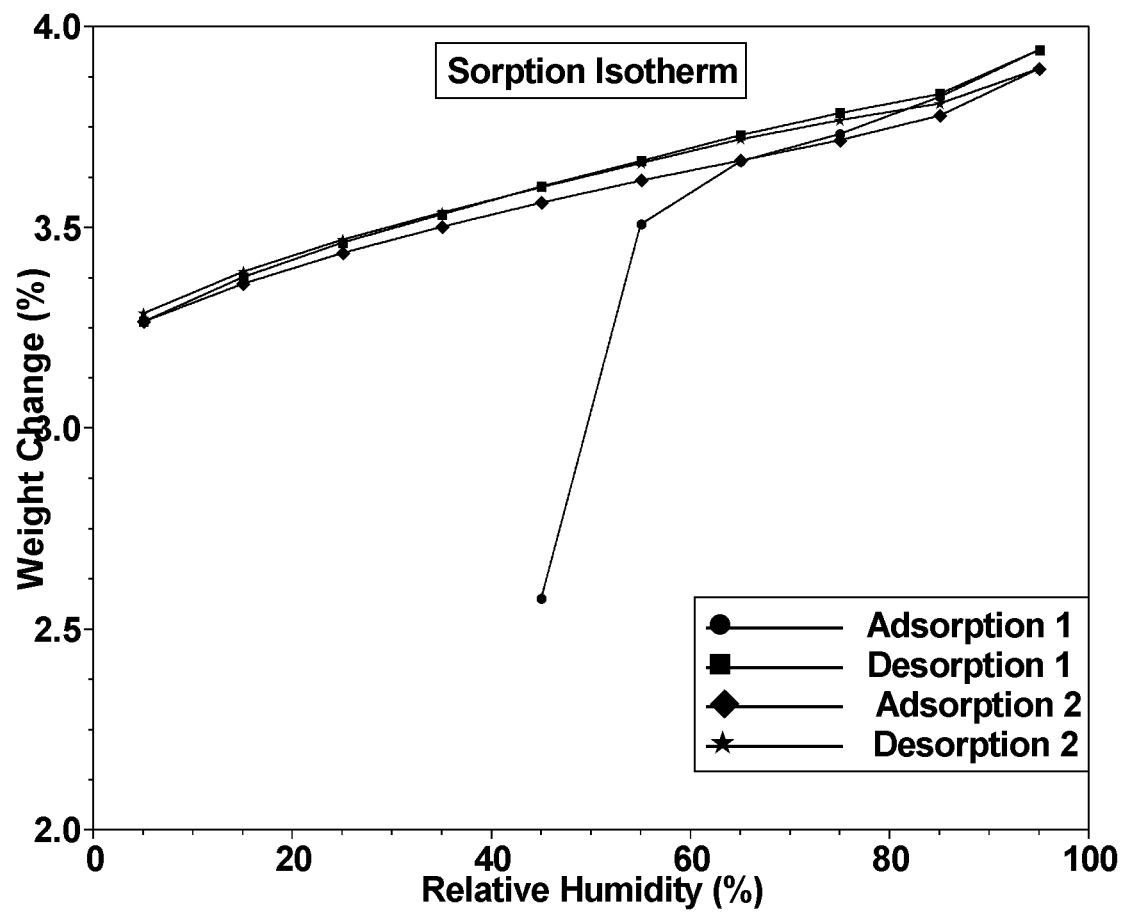
FIG. 29 is a DVS curve of Compound I Form XIV.

In some embodiments, Compound I Form XIV can be characterized by a differential scanning calorimetry (DSC) curve comprising a broad endotherm between temperatures of about 25° C. and 100° C. In another embodiment, the DSC curve further comprises an endotherm having onset temperature of about 258° C. In another embodiment, Compound I Form XIV can be characterized by a DSC curve substantially as shown in FIG. 27. In some embodiments, Compound I Form XIV can be characterized by a TGA curve substantially as shown in FIG. 28. In some embodiments, Compound I Form XIV can be characterized by a DVS curve substantially as shown in FIG. 29.

Crystalline Forms of Salts or Co-crystals of Compound I

The crystalline forms of salts or co-crystals of Compound I are discussed below.

Compound I Sesqui-Succinate Form III

Figure 30:
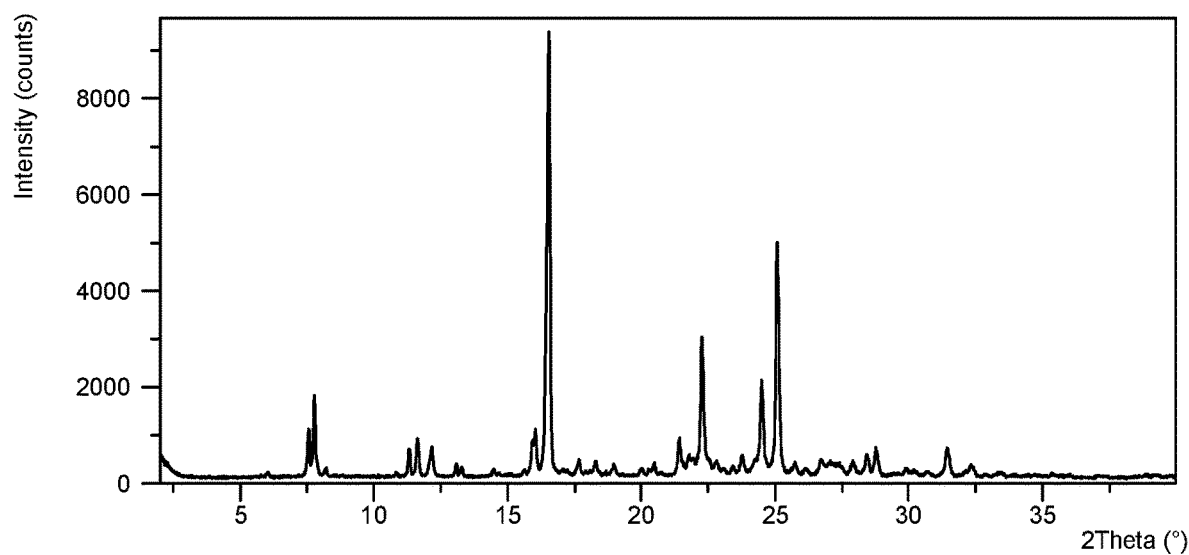
FIG. 30 is an X-ray powder diffractogram of Compound I Sesqui-Succinate Form III.

Compound I Sesqui-Succinate Form III is an ethyl acetate solvate (contains about 0.4 mol. eq. of ethyl acetate). Compound I Sesqui-Succinate Form III can be characterized by an X-ray powder diffractogram comprising peaks (±0.2° 2θ) at 7.8, 16.5 and 21.4° 2θ, as determined on a diffractometer using Cu-Kα radiation. The diffractogram can comprise additional peaks (±0.2° 2θ) at 12.2, 16.0 and 24.5° 2θ. Compound I Sesqui-Succinate Form III can be characterized by an X-ray powder diffractogram as substantially shown in FIG. 30. In one embodiment, Compound I Sesqui-Succinate Form III can be characterized by an X-ray powder diffractogram comprising at least three, at least four or at least five peaks (±0.2° 2θ) selected from 16.5, 24.5, 7.8, 16.0, 21.4, 15.9, 12.2, 8.2 and 6.0° 2θ, as determined on a diffractometer using Cu-Kα radiation.

Figure 31:
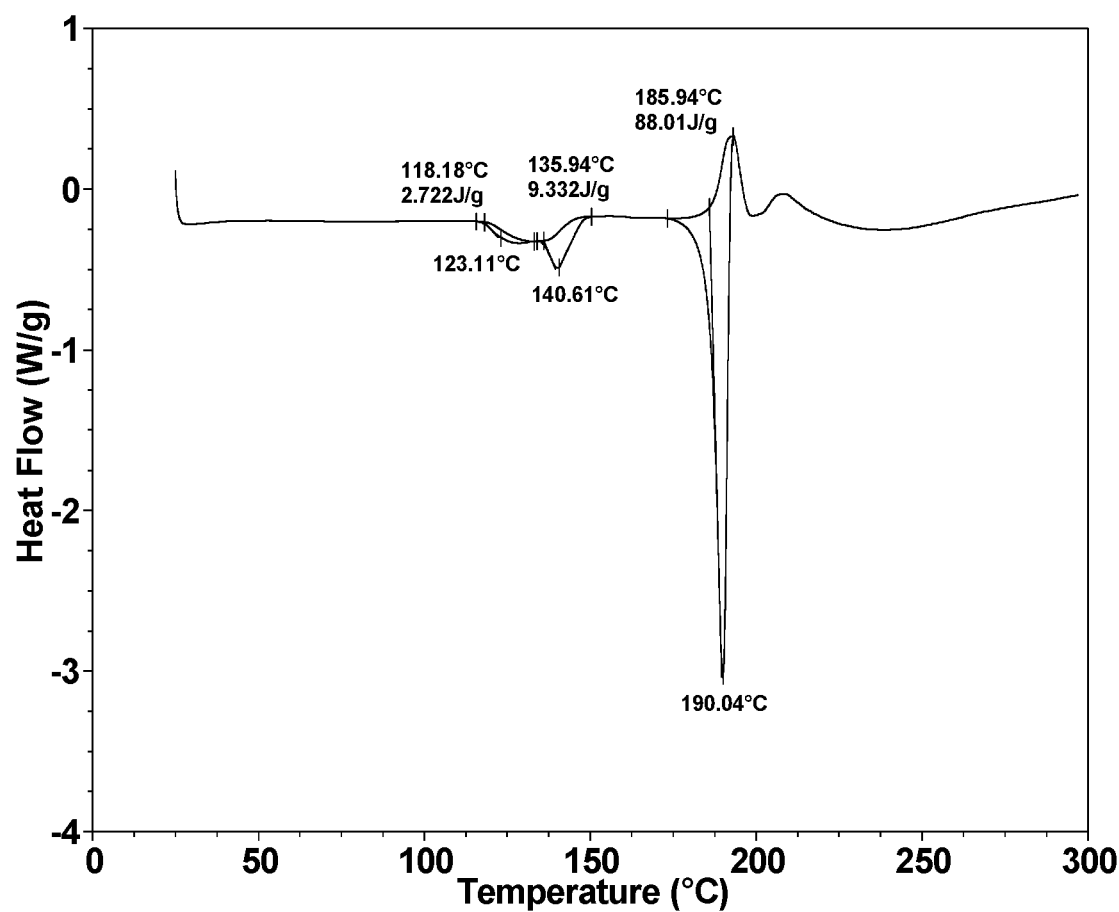
FIG. 31 is a DSC curve of Compound I Sesqui-Succinate Form III.
Figure 32:
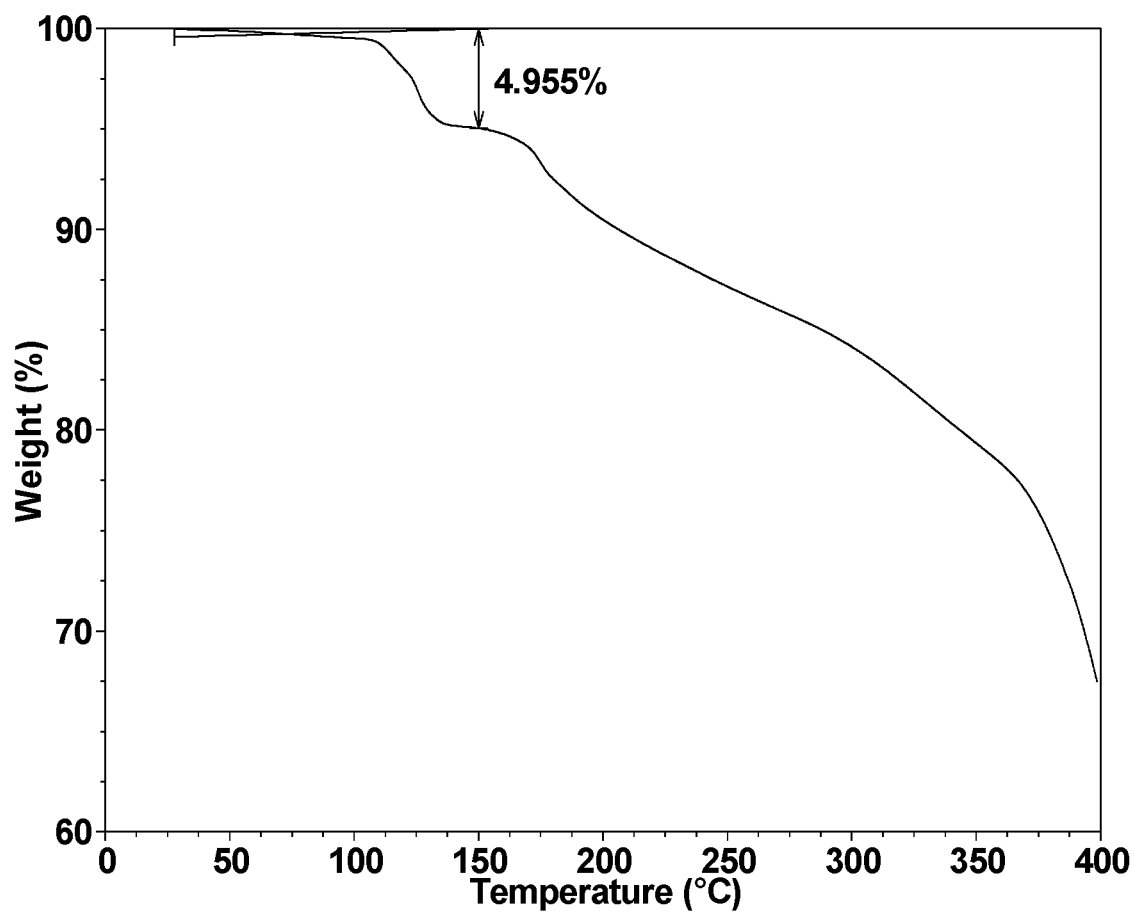
FIG. 32 is a TGA curve of Compound I Sesqui-Succinate Form III.

In some embodiments, Compound I Sesqui-Succinate Form III can be characterized by a DSC curve comprising endotherms having onset temperatures of about 118° C., 136° C. and 186° C. The endotherms can comprise peaks at about 123° C., 141° C. and 190° C. In another embodiment, Compound I Sesqui-Succinate Form III can be characterized by a DSC curve substantially as shown in FIG. 31. In some embodiments, Compound I Sesqui-Succinate Form III can be characterized by a TGA curve substantially as shown in FIG. 32. When heated to about 150° C., Compound I Sesqui-Succinate Form III converts to Compound I Succinate Form I which is disclosed in the U.S. Pat. No. 9,290,505.

Compound I Sesqui-Succinate Form IV

Figure 33:
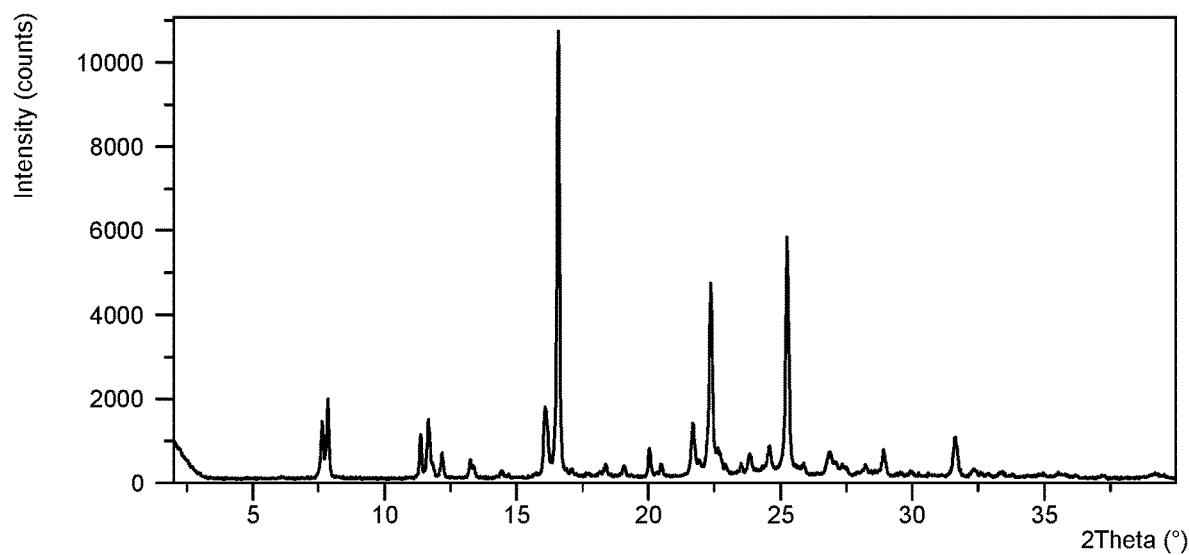
FIG. 33 is an X-ray powder diffractogram of Compound I Sesqui-Succinate Form IV.

Compound I Sesqui-Succinate Form IV is a MEK solvate. Compound I Sesqui-Succinate Form IV can be characterized by an X-ray powder diffractogram comprising peaks (±0.2° 2θ) at 16.6, 22.4 and 25.2° 2θ, as determined on a diffractometer using Cu-Kα radiation. The diffractogram can comprise additional peaks (±0.2° 2θ) at 7.9, 11.7 and 21.7° 2θ±0.2°. Compound I Sesqui-Succinate Form IV can be characterized by an X-ray powder diffractogram as substantially shown in FIG. 33. In one embodiment, Compound I Sesqui-Succinate Form IV can be characterized by an X-ray powder diffractogram comprising at least three, at least four or at least five peaks (±0.2° 2θ) selected from 16.6, 25.2, 22.4, 7.9, 11.7, 7.6, 21.7, 11.4 and 20.0° 2θ, as determined on a diffractometer using Cu-Kα radiation.

Figure 34:
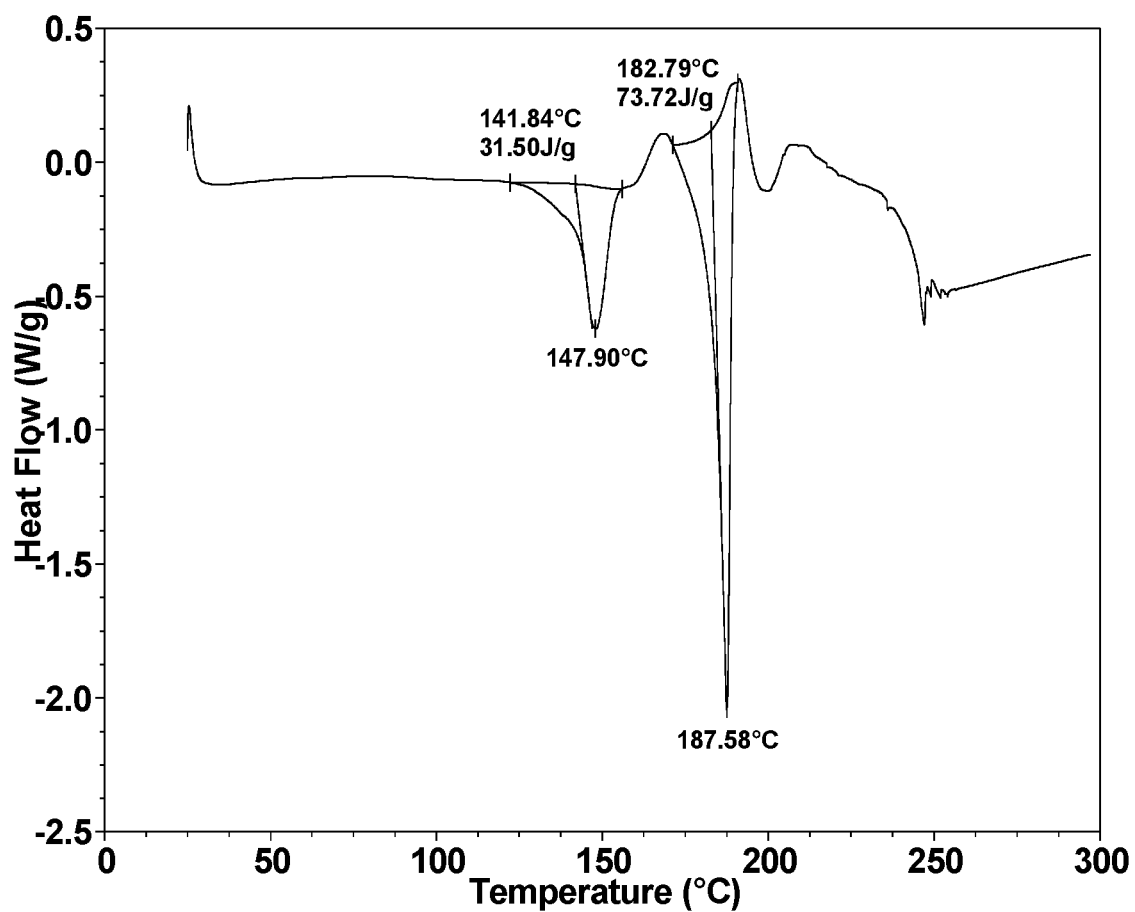
FIG. 34 is a DSC curve of Compound I Sesqui-Succinate Form IV.
Figure 35:
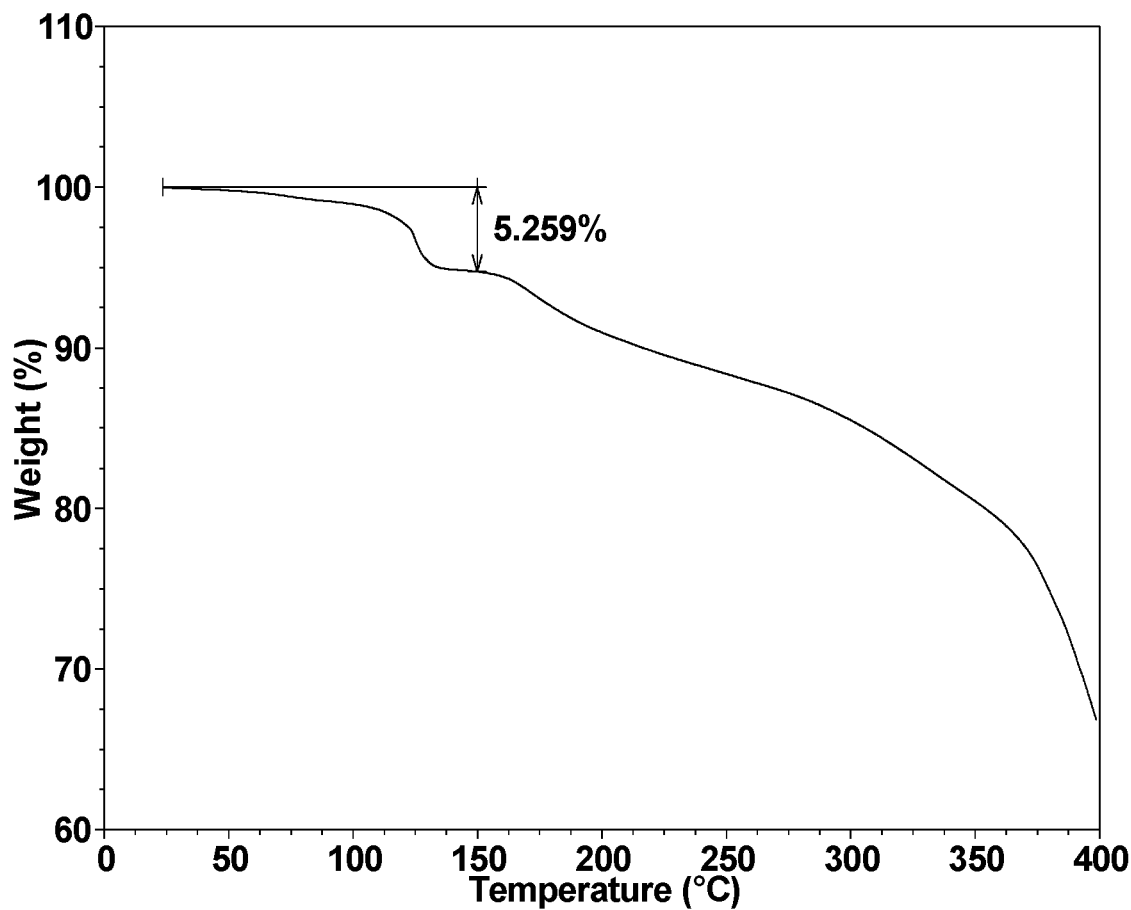
FIG. 35 is a TGA curve of Compound I Sesqui-Succinate Form IV.

In some embodiments, Compound I Sesqui-Succinate Form IV can be characterized by a DSC curve comprising endotherms having onset temperatures of about 142° C. and 183° C. The endotherms comprise peaks at about 148° C. and 188° C. In another embodiment, Compound I Sesqui-Succinate Form IV can be characterized by a DSC curve is substantially as shown in FIG. 34. In some embodiments, Compound I Sesqui-Succinate Form IV can be characterized by a TGA curve substantially as shown in FIG. 35.

Compound I Sesqui-Succinate Form V

Figure 36:
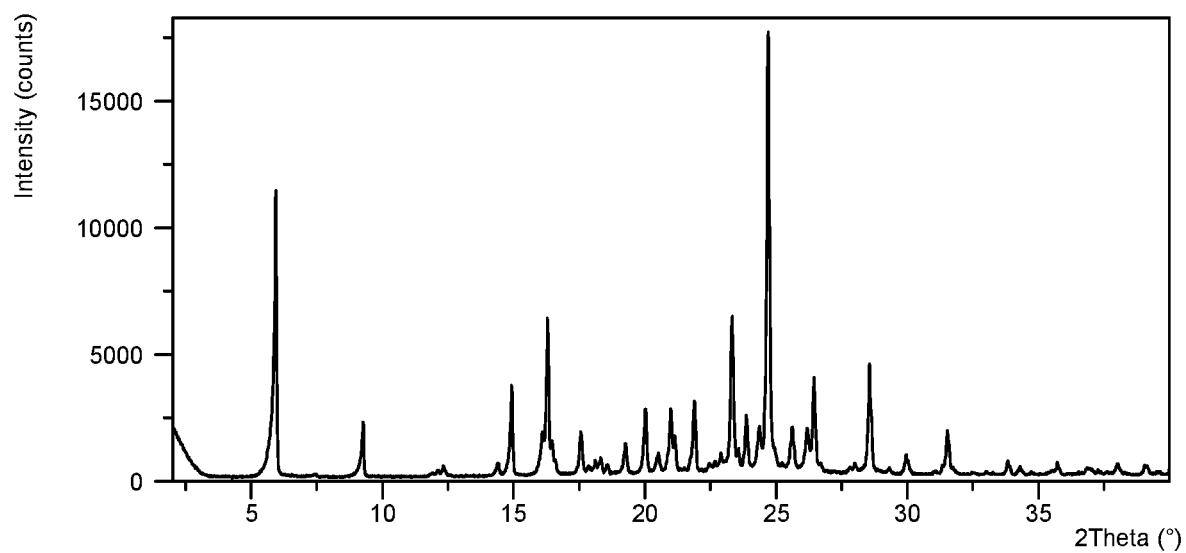
FIG. 36 is an X-ray powder diffractogram of Compound I Sesqui-Succinate Form V.

Compound I Sesqui-Succinate Form V is a THF solvate. Compound I Sesqui-Succinate Form V can be characterized by an X-ray powder diffractogram comprising peaks (±0.2° 2θ) at 5.9, 23.3 and 24.7° 2θ, as determined on a diffractometer using Cu-Kα radiation. The diffractogram can comprise additional peaks (±0.2° 2θ) at 16.3, 26.4 and 28.6° 2θ. Compound I Sesqui-Succinate Form V can be characterized by an X-ray powder diffractogram as substantially shown in FIG. 36. In one embodiment, Compound I Sesqui-Succinate Form V can be characterized by an X-ray powder diffractogram comprising at least three, at least four or at least five peaks (±0.2° 2θ) selected from 24.7, 5.9, 23.3, 16.3, 28.6, 26.4, 14.9, 21.9 and 21.0° 2θ, as determined on a diffractometer using Cu-Kα radiation.

Figure 37:
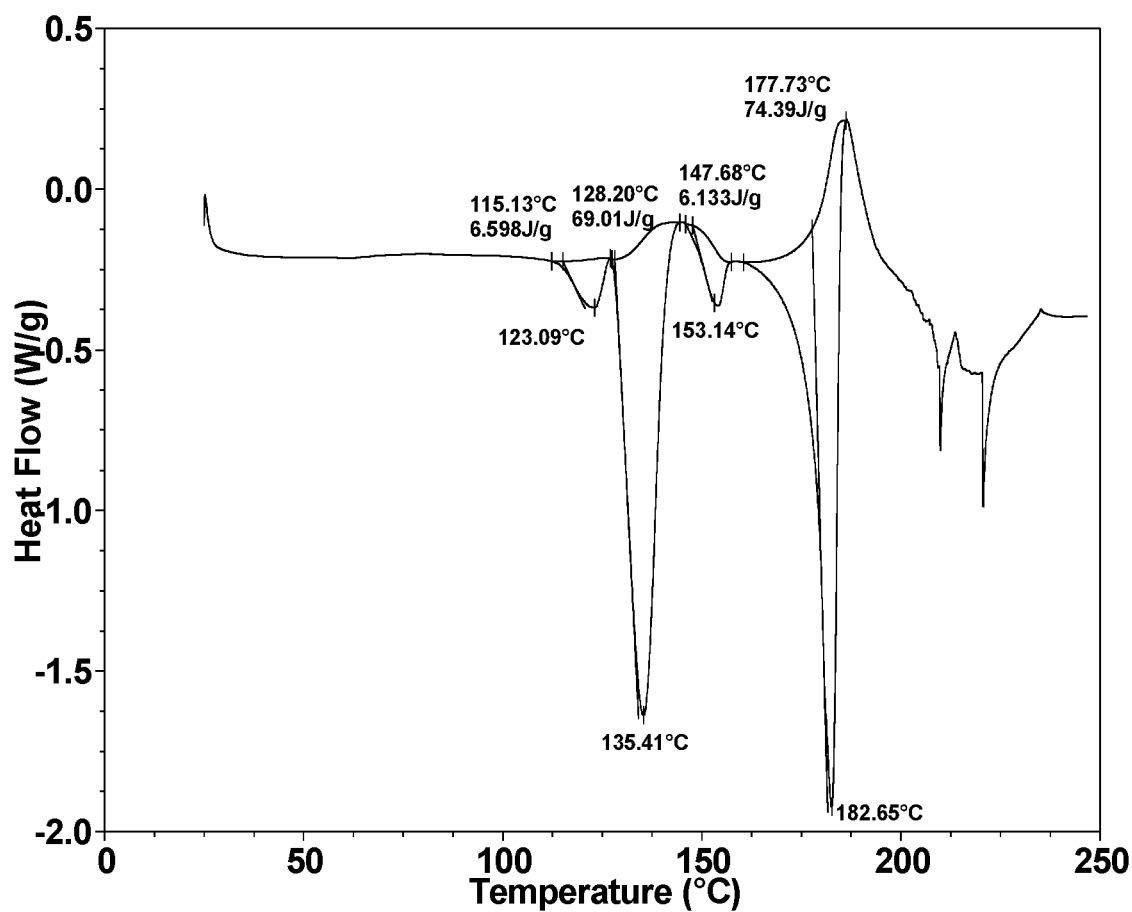
FIG. 37 is a DSC curve of Compound I Sesqui-Succinate Form V.
Figure 38:
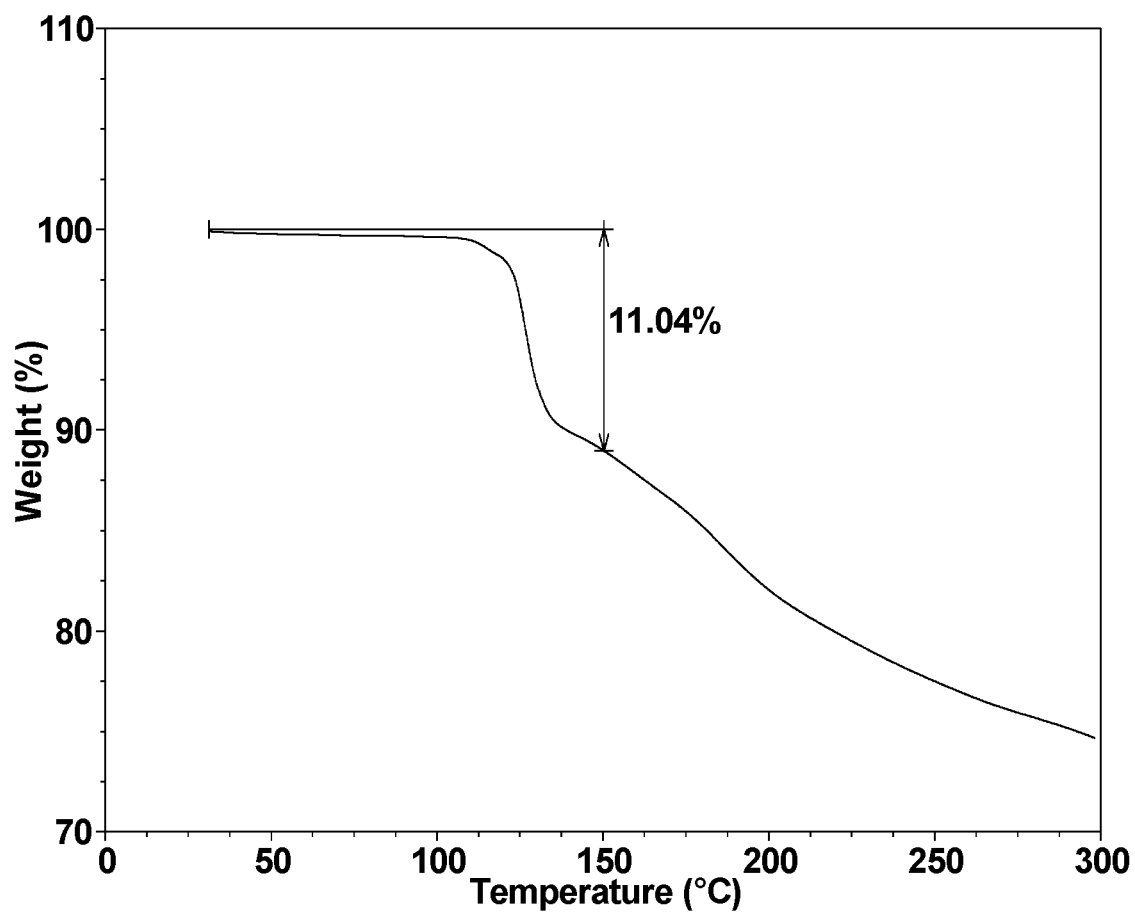
FIG. 38 is a TGA curve of Compound I Sesqui-Succinate Form V.

In some embodiments, Compound I Sesqui-Succinate Form V can be characterized by a DSC curve comprising endotherms having onset temperatures of about 115° C., 128° C., 148° C. and 178° C. The endotherms comprise peaks at about 123° C., 135° C., 153° C. and 183° C. In another embodiment, Compound I Sesqui-Succinate Form V can be characterized by a DSC curve substantially as shown in FIG. 37. In some embodiments, Compound I Sesqui-Succinate Form V can be characterized by a TGA curve substantially as shown in FIG. 38. When heated to about 150° C., Compound I Sesqui-Succinate Form V converts to Compound I Succinate Form I which is disclosed in the U.S. Pat. No. 9,290,505.

Compound I Hemi-Succinate Form I

Figure 39:
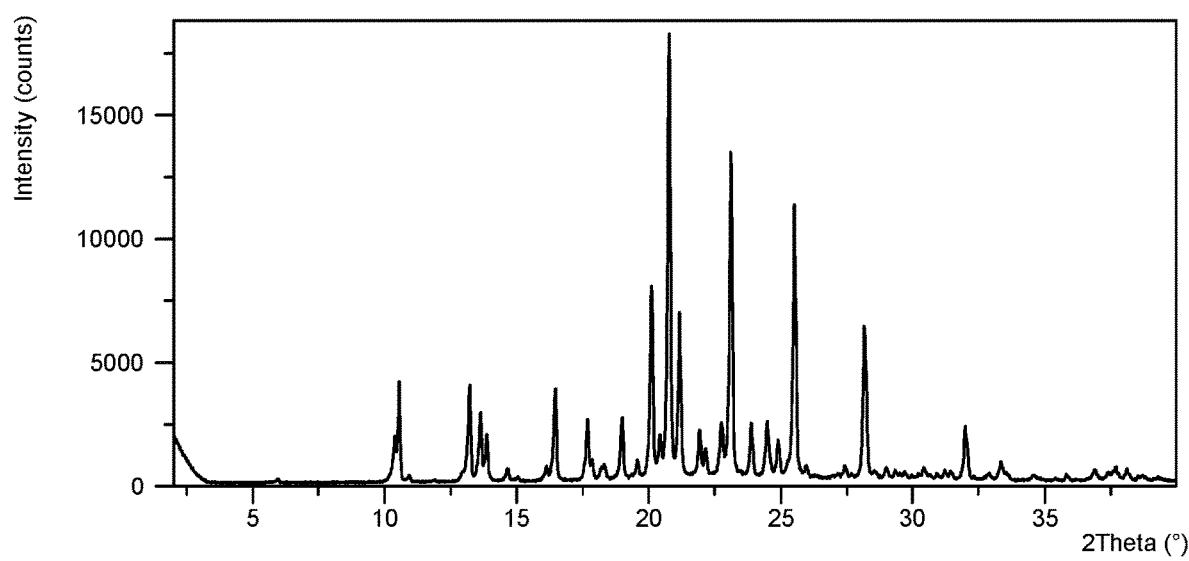
FIG. 39 is an X-ray powder diffractogram of Compound I Hemi-Succinate Form I.

Compound I Hemi-Succinate Form I is a monohydrate. Compound I Hemi-Succinate Form I can be characterized by an X-ray powder diffractogram comprising peaks (±0.2° 2θ) at 20.8, 23.1 and 25.5° 2θ, as determined on a diffractometer using Cu-Kα radiation. The diffractogram can comprise additional peaks (±0.2° 2θ) at 20.1, 21.2 and 28.1° 2θ. Compound I Hemi-Succinate Form I can be characterized by an X-ray powder diffractogram as substantially shown in FIG. 39. In one embodiment, Compound I Hemi-Succinate Form I can be characterized by an X-ray powder diffractogram comprising at least three, at least four or at least five peaks (±0.2° 2θ) selected from 20.8, 23.1, 25.5, 20.1, 21.2, 28.1, 10.6, 13.2 and 16.5° 2θ, as determined on a diffractometer using Cu-Kα radiation.

Figure 40:
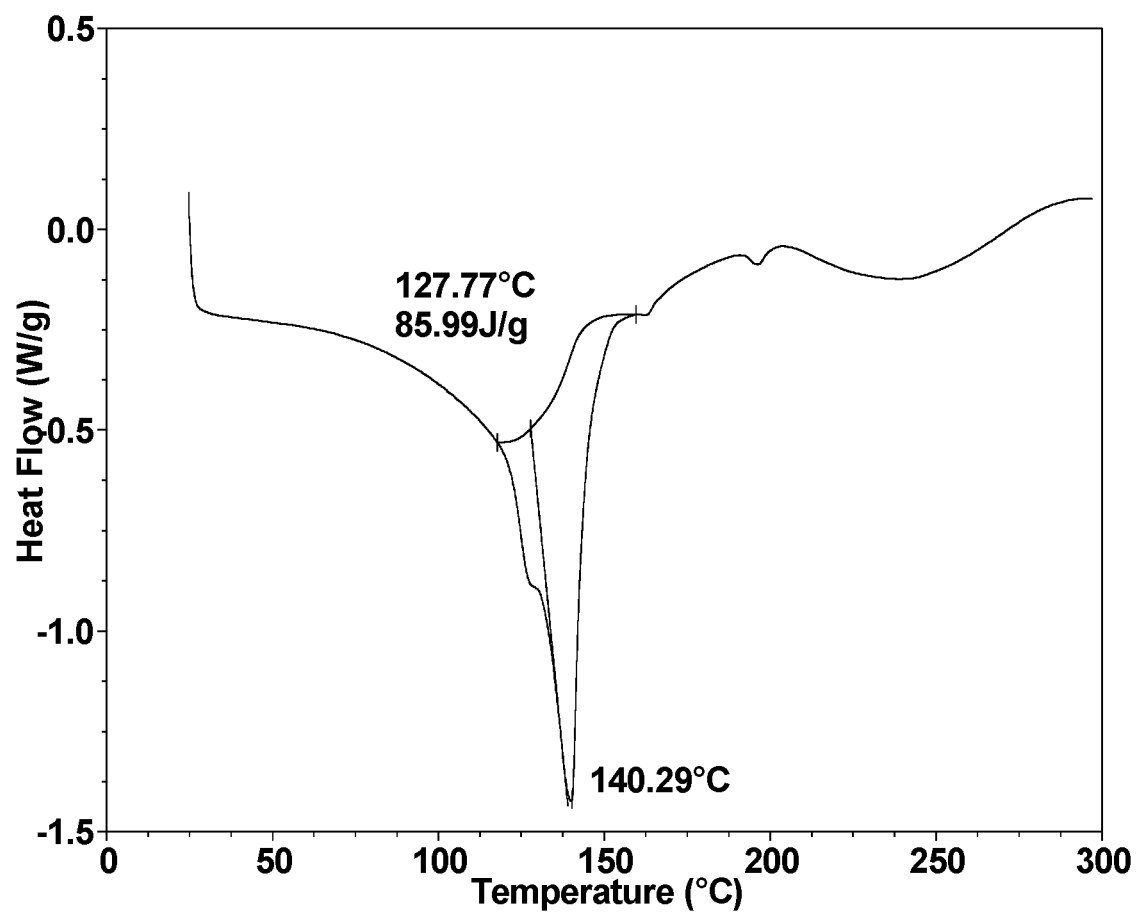
FIG. 40 is a DSC curve of Compound I Hemi-Succinate Form I.
Figure 41:
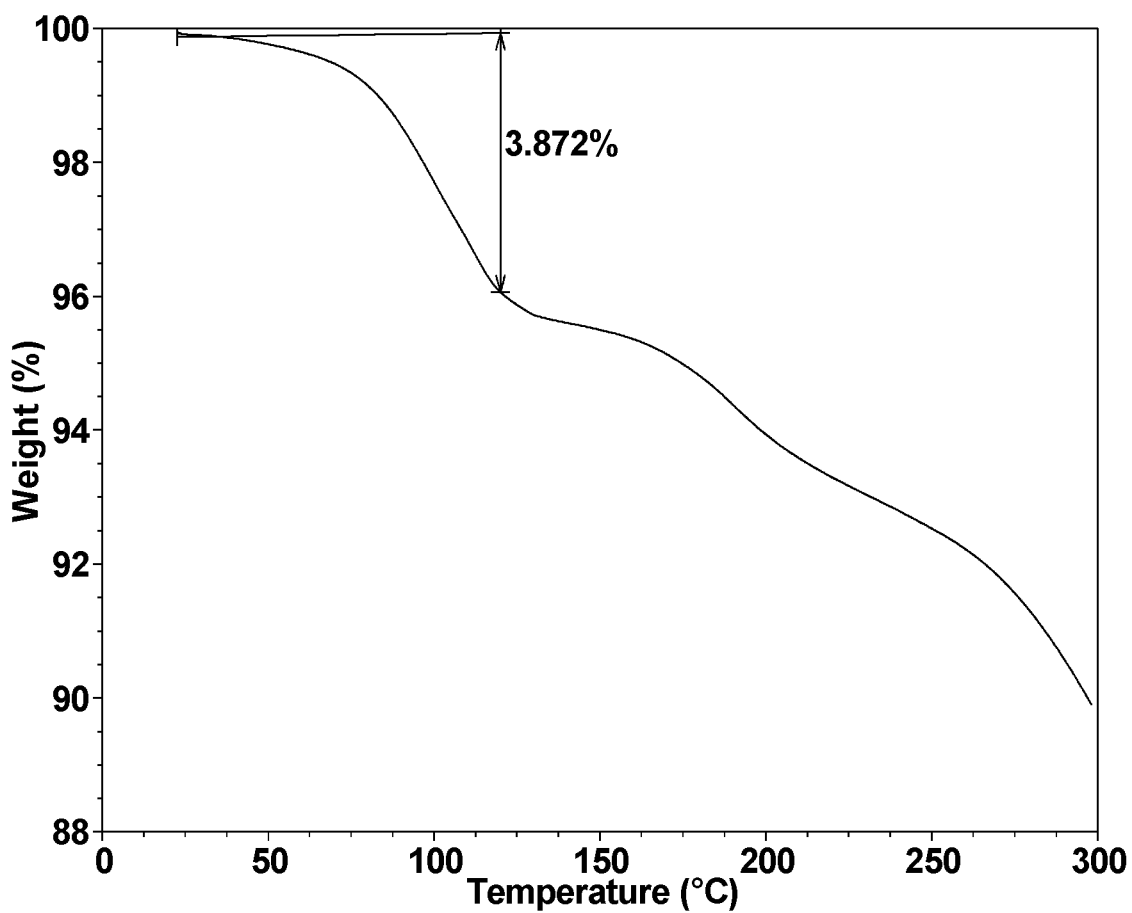
FIG. 41 is a TGA curve of Compound I Hemi-Succinate Form I.
Figure 42:
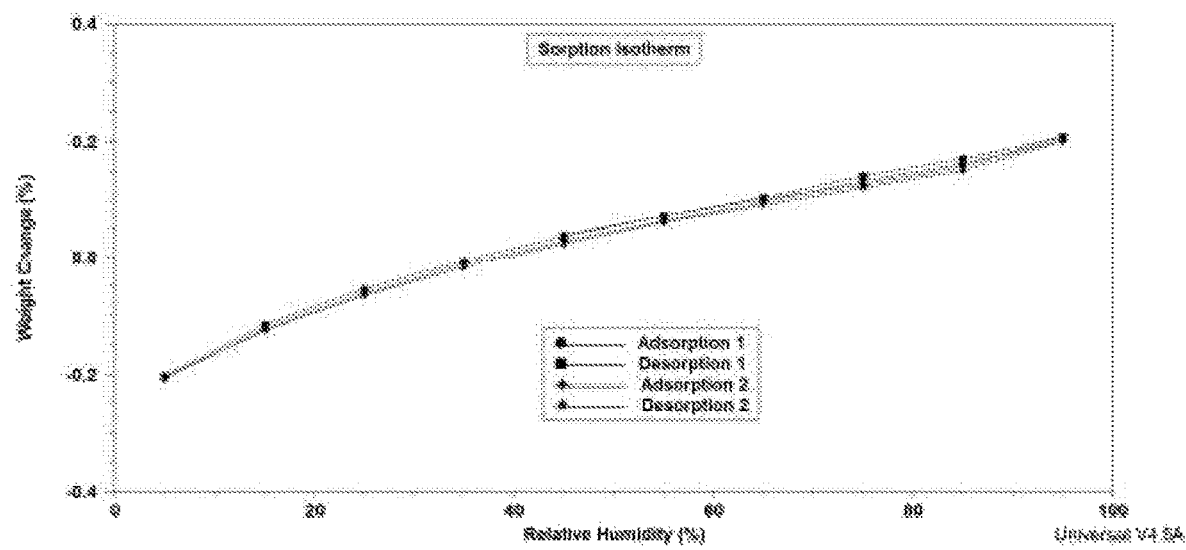
FIG. 42 is a DVS curve of Compound I Hemi-Succinate Form I.

In some embodiments, Compound I Hemi-Succinate Form I can be characterized by a DSC curve comprising an endotherm having an onset temperature of about 128° C. The endotherm comprises a peak at about 140° C. In another embodiment, Compound I Hemi-Succinate Form I can be characterized by a DSC curve substantially as shown in FIG. 40. In some embodiments, Compound I Hemi-Succinate Form I can be characterized by a TGA curve substantially as shown in FIG. 41. In some embodiments, Compound I Hemi-Succinate Form I can be characterized by a DVS curve substantially as shown in FIG. 42 DVS analysis shows that it is slightly hygroscopic with an uptake of about 0.4 wt. % of water at 90% RH at 25° C. Compound I Hemi-Succinate Form I is a monoclinic crystalline form having unit cell parameters: a equal to 15.68 Å, b equal to 9.63 Å, c equal to 17.66 Å, α equal to 90°, β equal to 108.12° and γ equal to 90°.

Compound I Mono-HCl salt Form I

Figure 43:
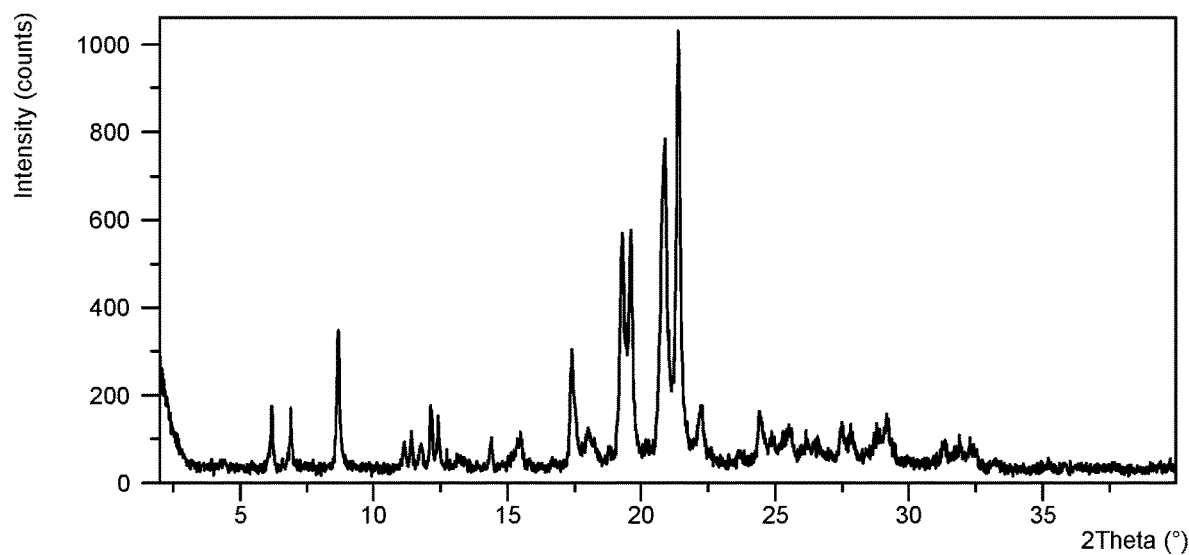
FIG. 43 is an X-ray powder diffractogram of Compound I Mono-HCl Salt Form I.

Compound I Mono-HCl salt Form I can be characterized by an X-ray powder diffractogram comprising peaks (±0.2° 2θ) at 8.7, 19.3 and 21.4° 2θ, as determined on a diffractometer using Cu-Kα radiation. The diffractogram can comprise additional peaks (±0.2° 2θ) at 17.4, 19.6 and 20.9° 2θ. Compound I Mono-HCl salt Form I can be characterized by an X-ray powder diffractogram as substantially shown in FIG. 43. In one embodiment, Compound I Mono-HCl salt Form I can be characterized by an X-ray powder diffractogram comprising at least three, at least four or at least five peaks (±0.2° 2θ) selected from 21.4, 8.7, 19.3, 20.9, 19.6, 17.4, 12.1, 6.2 and 6.9° 2θ, as determined on a diffractometer using Cu-Kα radiation.

Figure 44:
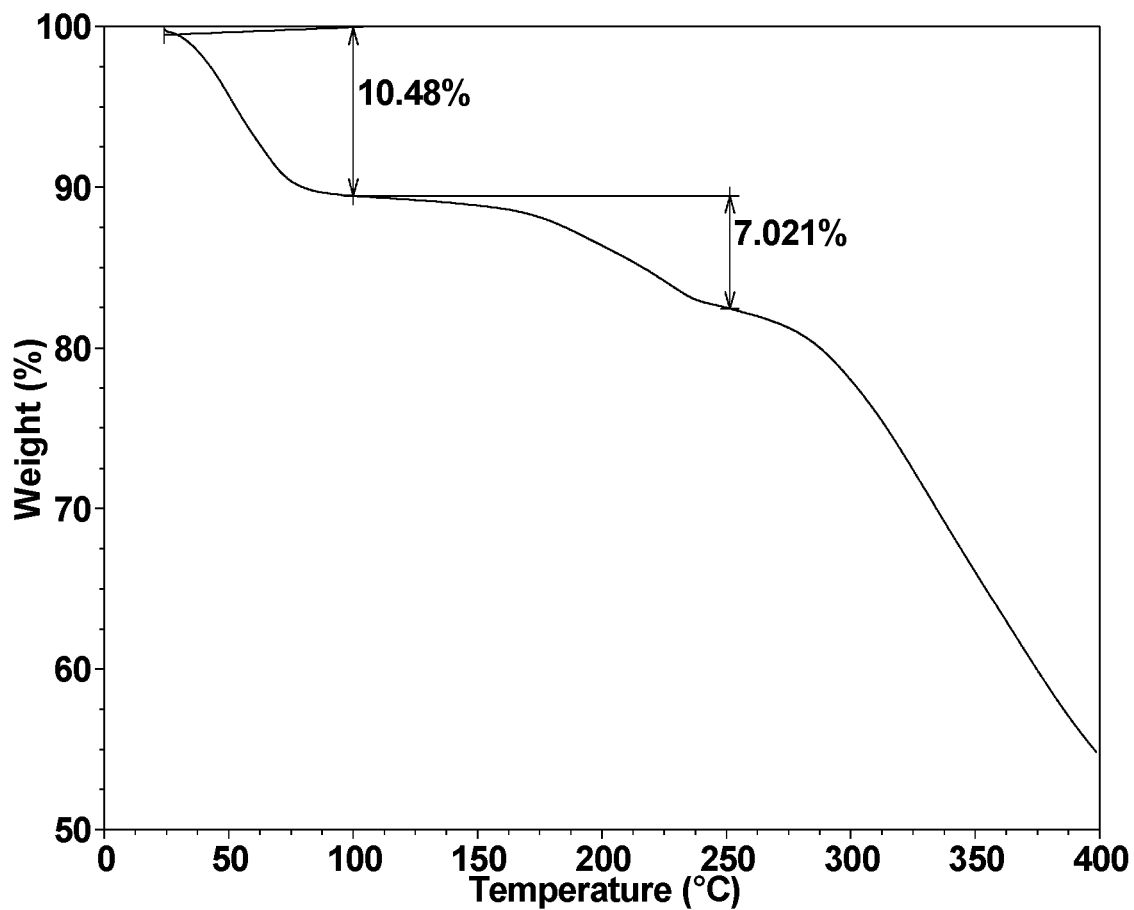
FIG. 44 is a TGA curve of Compound I Mono-HCl Salt Form I.

In some embodiments, Compound I Mono-HCl salt Form I can be characterized by a TGA curve substantially as shown in FIG. 44.

Compound I Mono-HCl salt Form II

Figure 45:
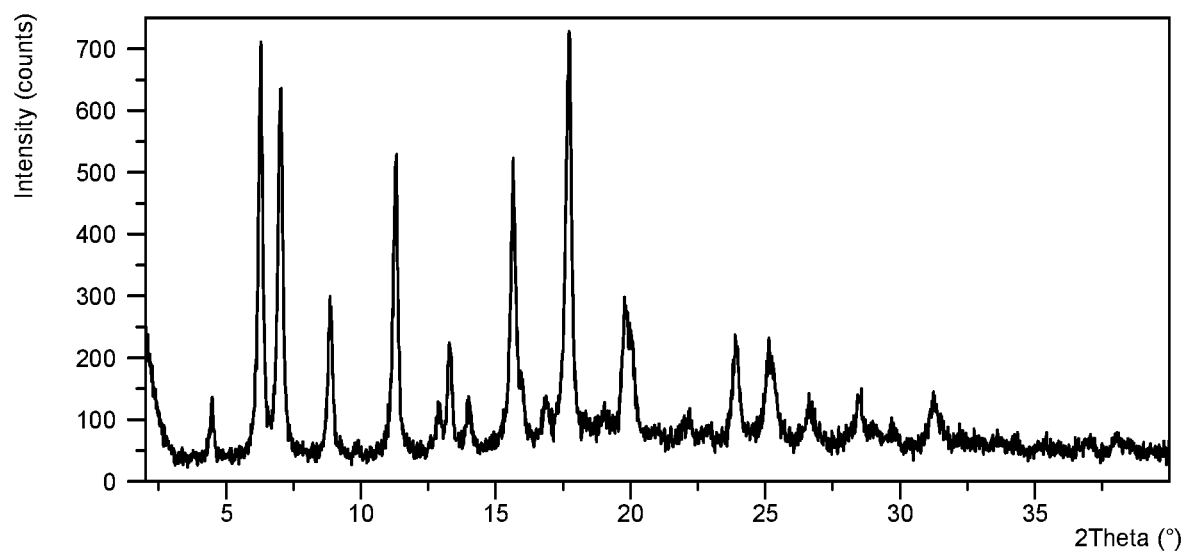
FIG. 45 is an X-ray powder diffractogram of Compound I Mono-HCl Salt Form II.

Compound I Mono-HCl salt Form II can be characterized by an X-ray powder diffractogram comprising peaks (±0.2° 2θ) at 6.3, 11.3 and 17.7° 2θ, as determined on a diffractometer using Cu-Kα radiation. The diffractogram can comprise additional peaks (±0.2° 2θ) at 7.0, 8.9 and 15.7° 2θ. Compound I Mono-HCl salt Form II can be characterized by an X-ray powder diffractogram as substantially shown in FIG. 45. In one embodiment, Compound I Mono-HCl salt Form II can be characterized by an X-ray powder diffractogram comprising at least three, at least four or at least five peaks (±0.2° 2θ) selected from 17.7, 6.3, 11.3, 7.0, 15.7, 8.9, 19.8, 23.9 and 13.3° 2θ, as determined on a diffractometer using Cu-Kα radiation.

Figure 46:
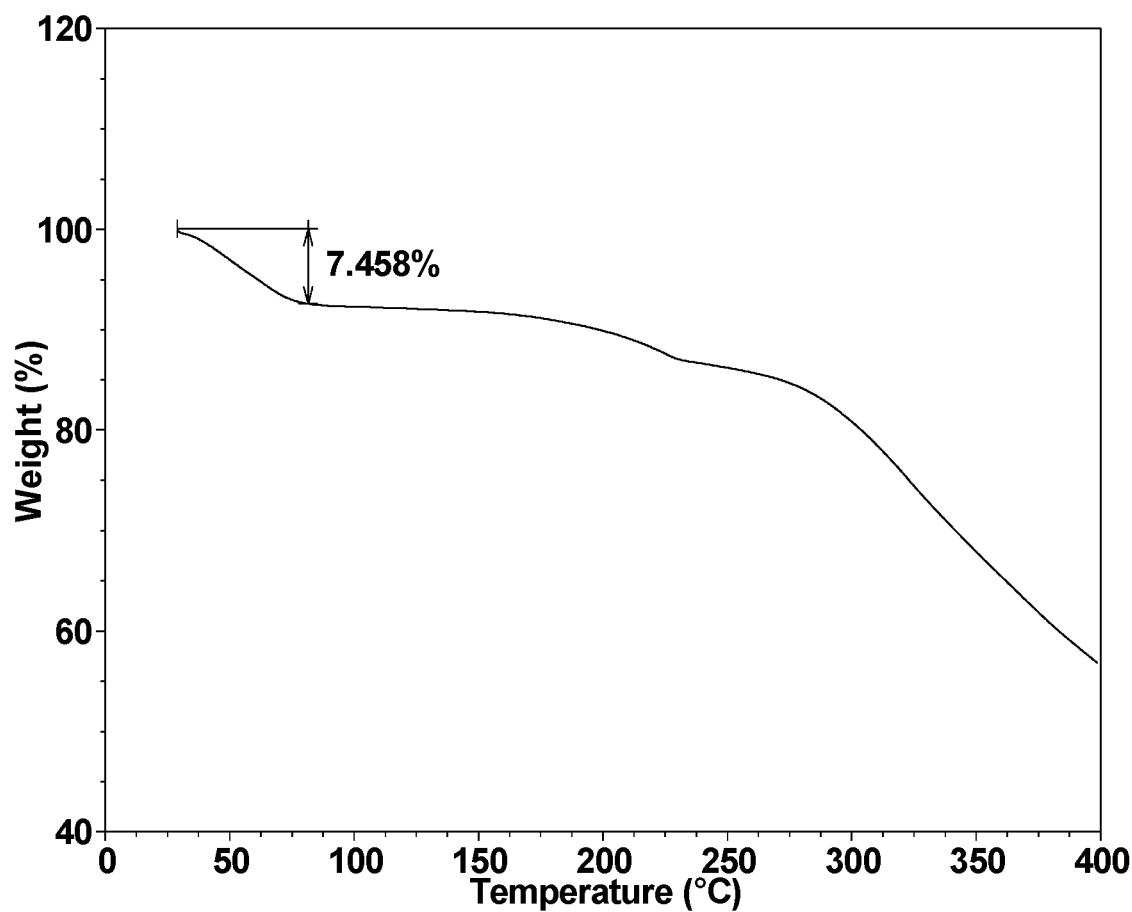
FIG. 46 is a TGA curve of Compound I Mono-HCl Salt Form II.
Figure 47:
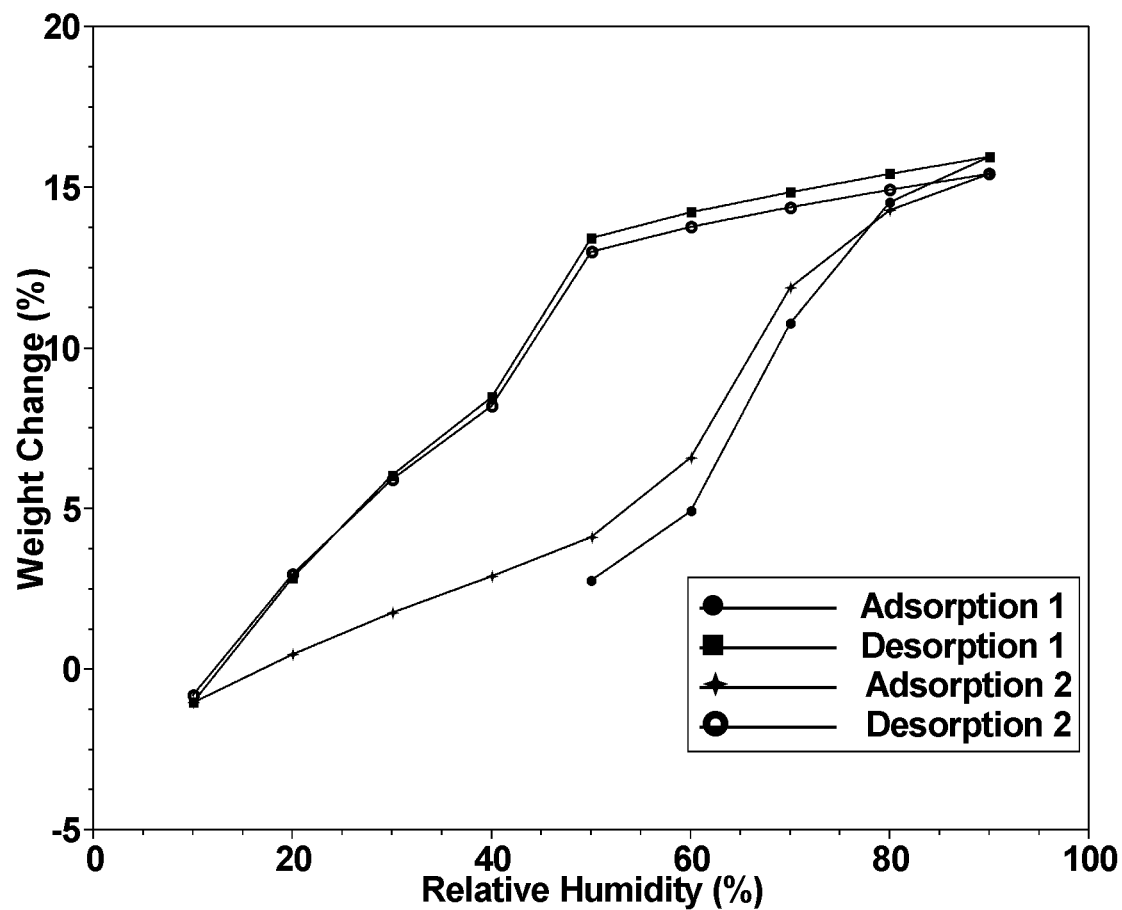
FIG. 47 is a DVS curve of Compound I Mono-HCl Salt Form II.

In some embodiments, Compound I Mono-HCl salt Form II can be characterized by a TGA curve substantially as shown in FIG. 46. In some embodiments, Compound I Mono-HCl salt Form II can be characterized by a DVS curve substantially as shown in FIG. 47. DVS analysis shows that it absorbs up to about 16 wt. % of water at 90% RH at 25° C. (very hygroscopic).

Compound I Mono-HCl salt Form III

Figure 48:
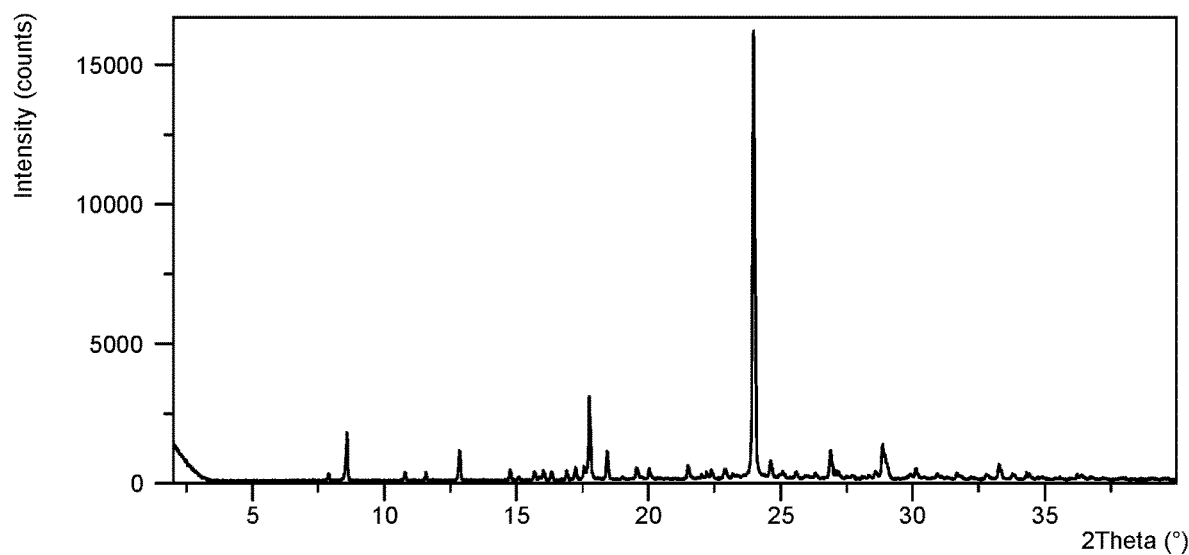
FIG. 48 is an X-ray powder diffractogram of Compound I Mono-HCl Salt Form III.

Compound I Mono-HCl salt Form III is a di-propylene glycol solvate. Compound I Mono-HCl salt Form III can be characterized by an X-ray powder diffractogram comprising peaks (±0.2° 2θ) at 8.6, 17.8 and 24.0° 2θ, as determined on a diffractometer using Cu-Kα radiation. The diffractogram can comprise additional peaks (±0.2° 2θ) at 12.8, 26.9 and 28.9° 2θ. Compound I Mono-HCl salt Form III can be characterized by an X-ray powder diffractogram as substantially shown in FIG. 48. In one embodiment, Compound I Mono-HCl salt Form III can be characterized by an X-ray powder diffractogram comprising at least three, at least four or at least five peaks (±0.2° 2θ) selected from 24.0, 17.8, 8.6, 28.9, 12.8, 26.9, 18.4, 24.6 and 33.3° 2θ, as determined on a diffractometer using Cu-Kα radiation.

Figure 49:
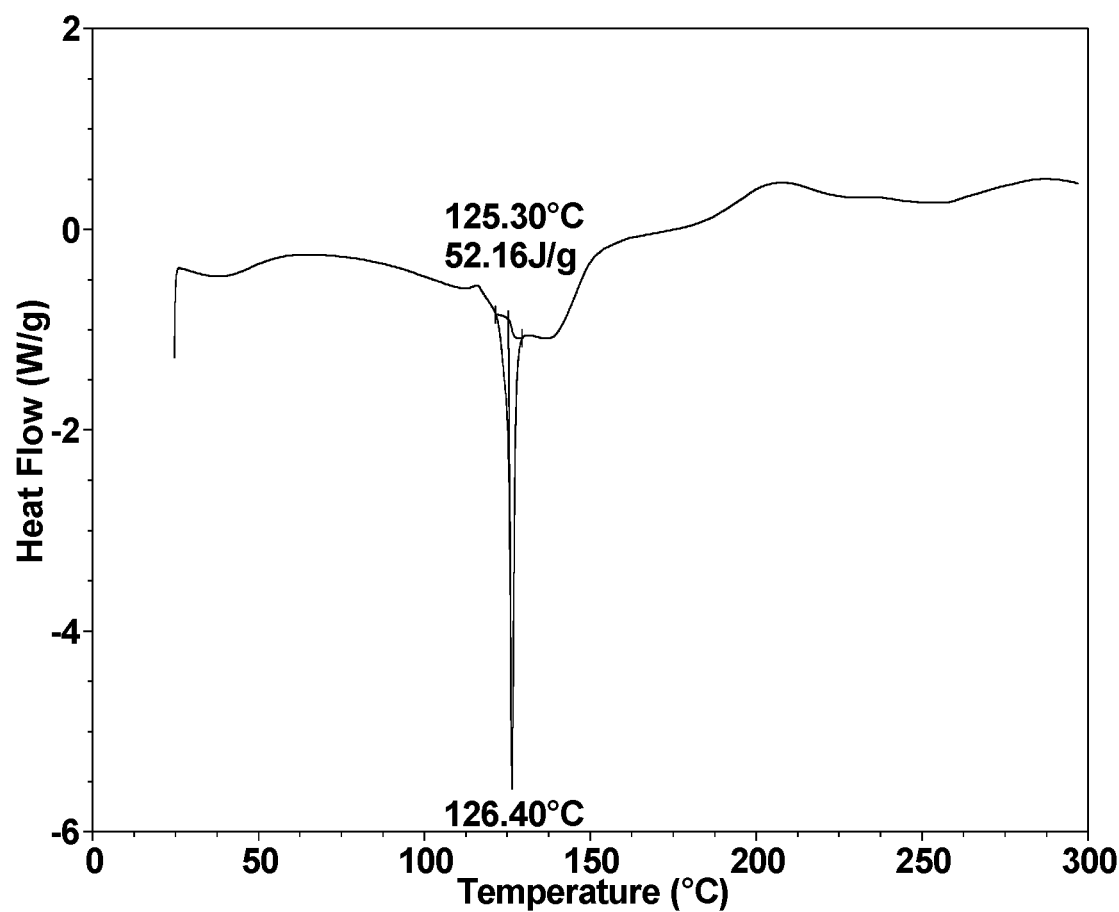
FIG. 49 is a DSC curve of Compound I Mono-HCl Salt Form III.
Figure 50:
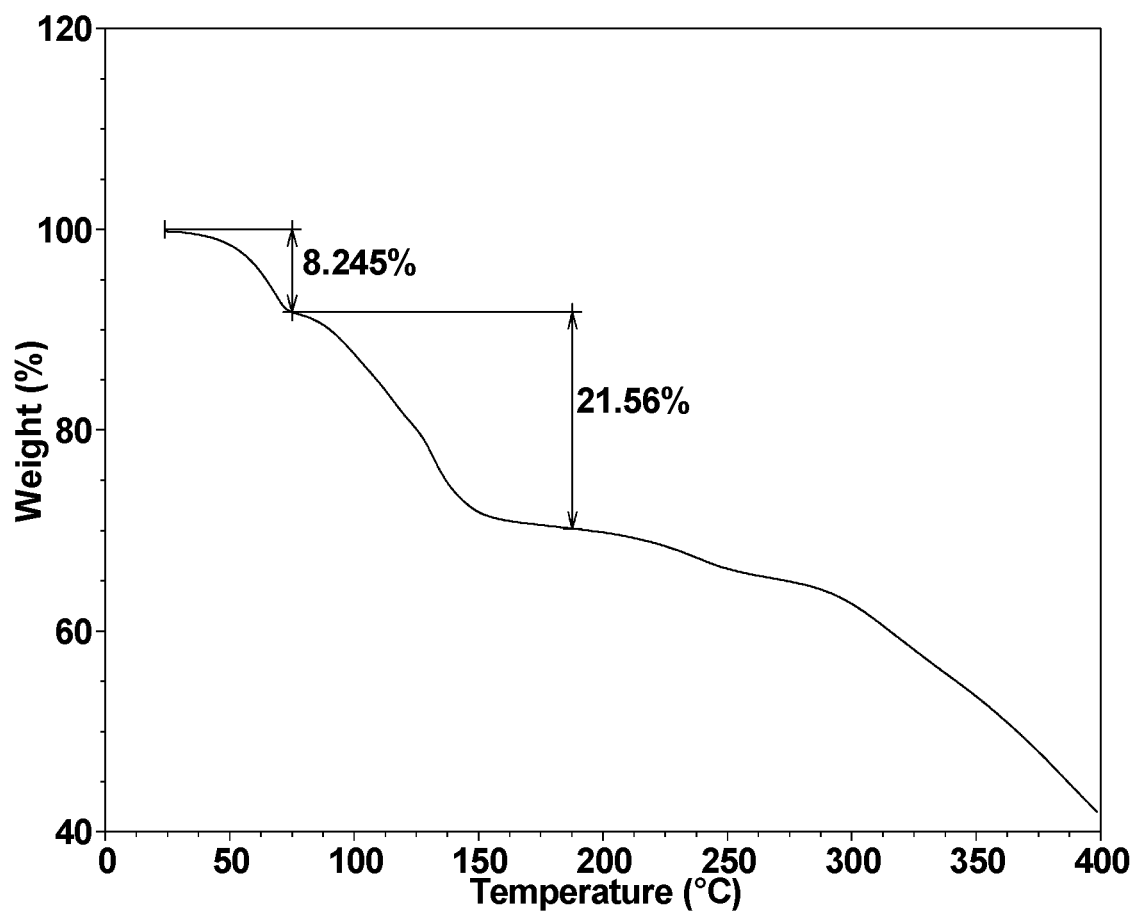
FIG. 50 is a TGA curve of Compound I Mono-HCl Salt Form III.

In some embodiments, Compound I Mono-HCl salt Form III can be characterized by a DSC curve comprising endotherms having an onset temperature of about 125° C. The endotherm comprises a peak at about 126° C. In another embodiment, Compound I Mono-HCl salt Form III can be characterized by a DSC curve substantially as shown in FIG. 49. In some embodiments, Compound I Mono-HCl salt Form III can be characterized by a TGA curve substantially as shown in FIG. 50. Compound I Mono-HCl salt Form III is a triclinic crystalline form having unit cell parameters: a equal to 11.03 Å, b equal to 12.13 Å, c equal to 12.89 Å, α equal to 66.9°, β equal to 79.52° and γ equal to 83.88°.

Compound I Sesqui-Adipate Form I

Figure 51:
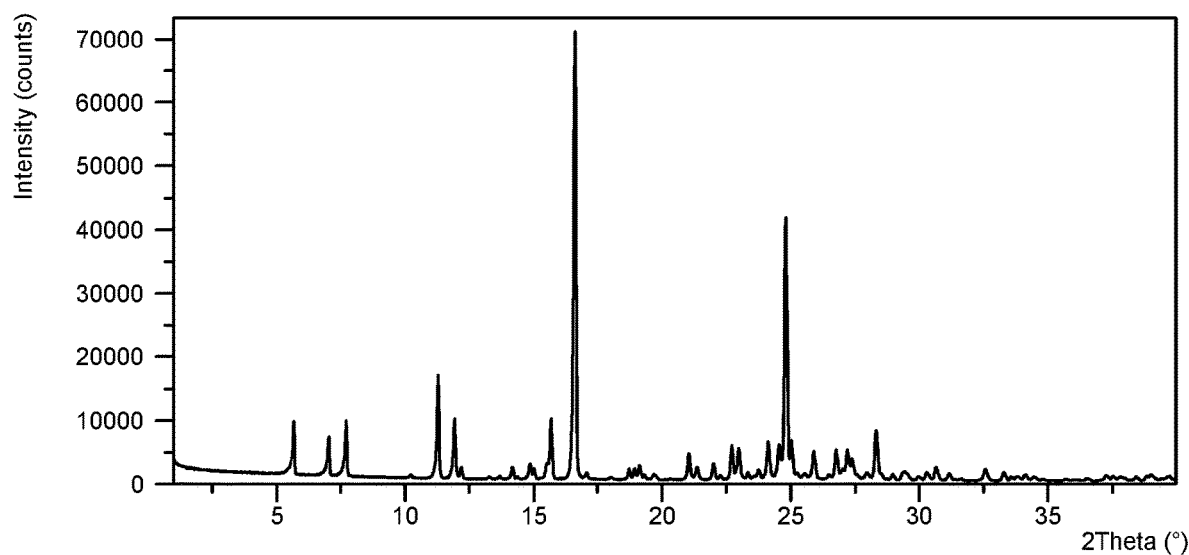
FIG. 51 is an X-ray powder diffractogram of Compound I Sesqui Adipate Form I.

Compound I Sesqui-Adipate Form I can be characterized by an X-ray powder diffractogram comprising peaks (±0.2° 2θ) at 11.3, 16.6 and 24.8° 2θ, as determined on a diffractometer using Cu-Kα radiation. The diffractogram can comprise additional peaks (±0.2° 2θ) at 7.7, 11.9 and 15.7° 2θ. Compound I Sesqui-Adipate Form I can be characterized by an X-ray powder diffractogram as substantially shown in FIG. 51. In one embodiment, Compound I Sesqui-Adipate Form I can be characterized by an X-ray powder diffractogram comprising at least three, at least four or at least five peaks (±0.2° 2θ) selected from 16.6, 24.8, 11.3, 15.7, 11.9, 7.7, 5.7, 28.3 and 25.0° 2θ, as determined on a diffractometer using Cu-Kα radiation.

Figure 52:
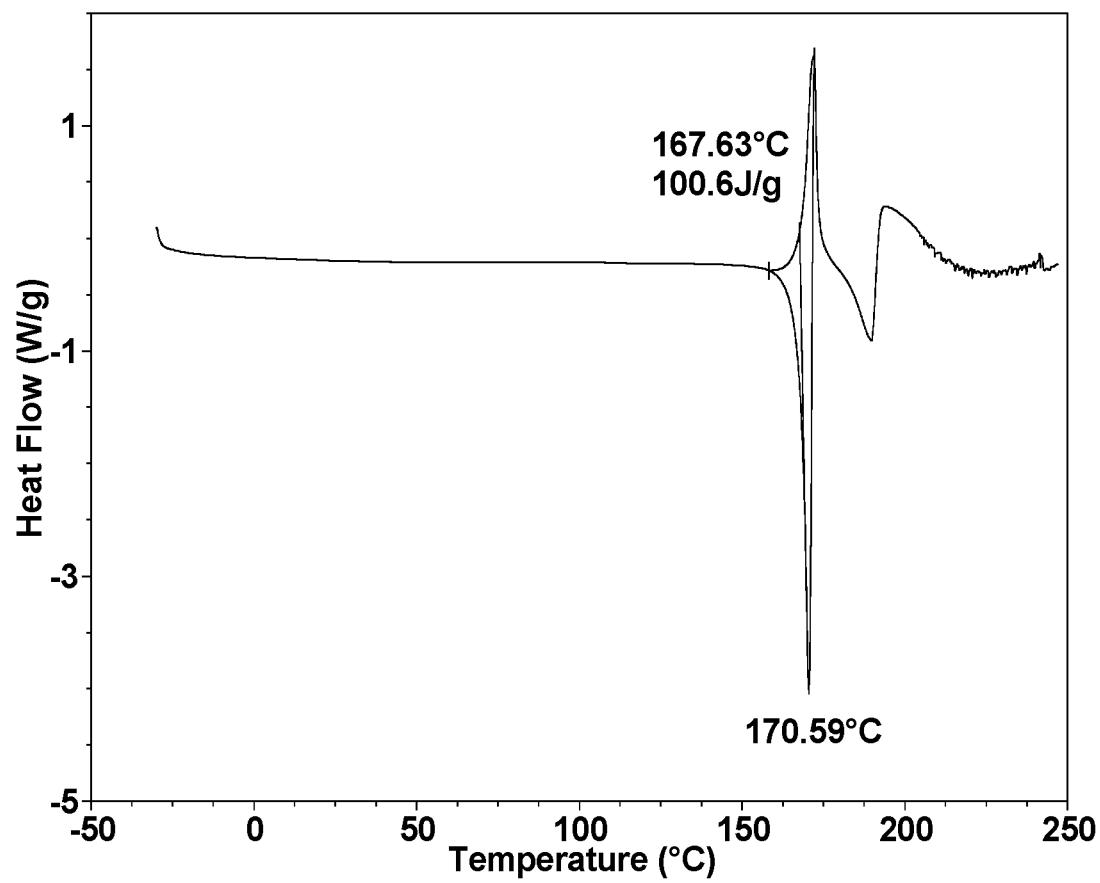
FIG. 52 is a DSC curve of Compound I Sesqui Adipate Form I.
Figure 53:
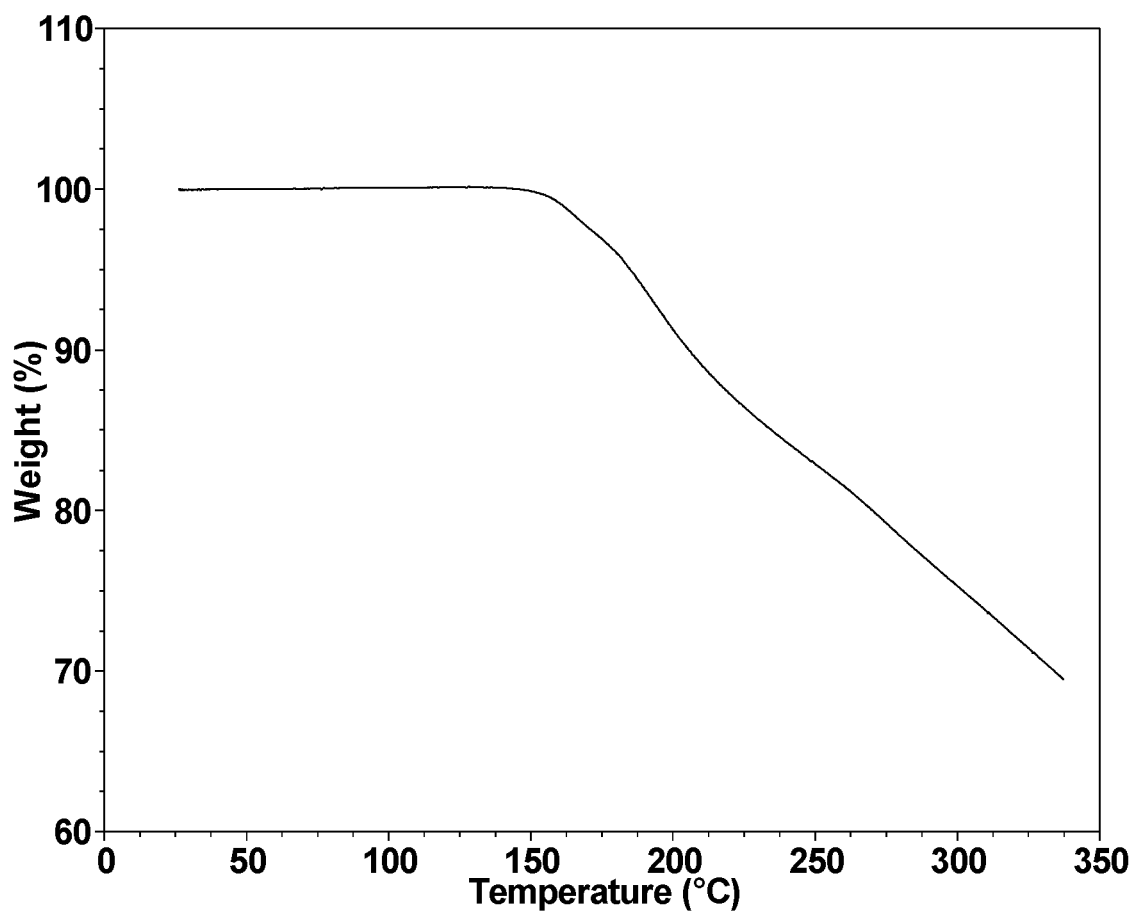
FIG. 53 is a TGA curve of Compound I Sesqui Adipate Form I.
Figure 54:
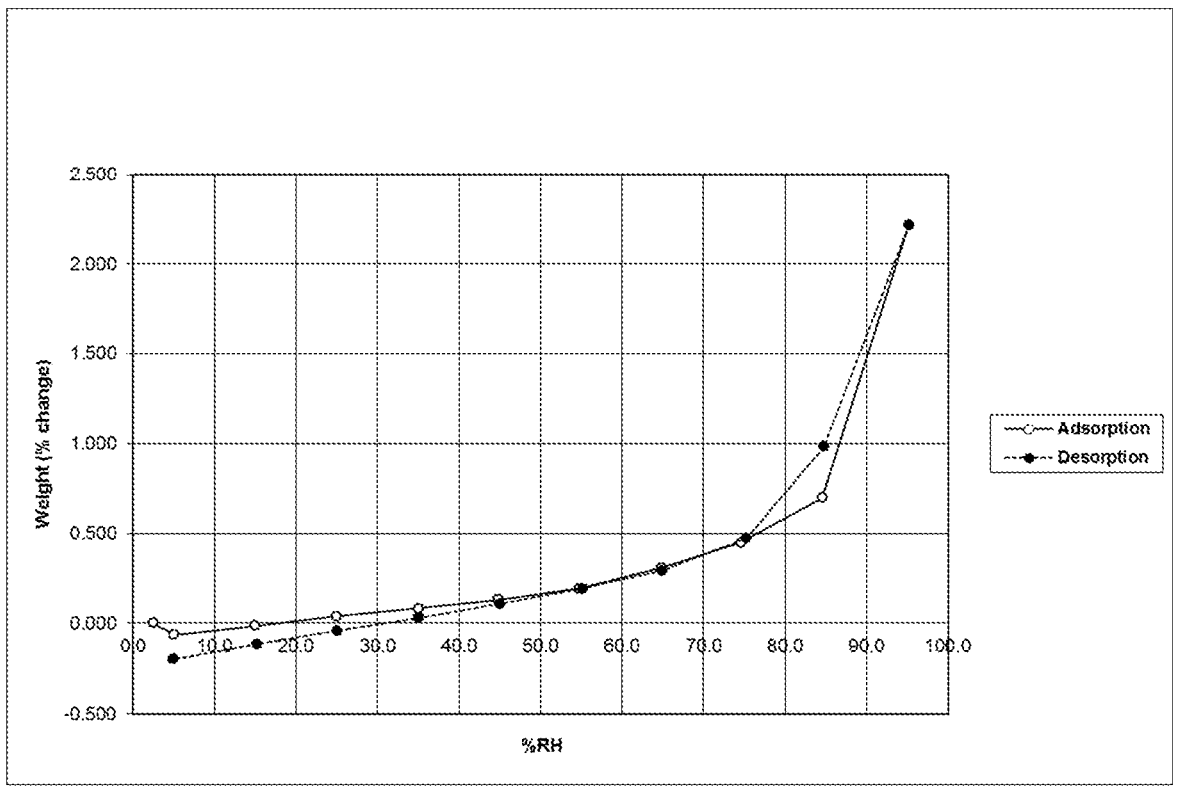
FIG. 54 is a DVS curve of Compound I Sesqui Adipate Form I.

In some embodiments, Compound I Sesqui-Adipate Form I can be characterized by a DSC curve comprising endotherms having an onset temperature of about 168° C. The endotherm comprises a peak at about 171° C. In another embodiment, Compound I Sesqui-Adipate Form I can be characterized by a DSC curve is substantially as shown in FIG. 52. In some embodiments, Compound I Sesqui-Adipate Form I can be characterized by a TGA curve substantially as shown in FIG. 53. In some embodiments, Compound I Sesqui-Adipate Form I can be characterized by a DVS curve substantially as shown in FIG. 54. DVS analysis shows that it is moderately hygroscopic, showing an uptake of about 2.1 wt. % of water at 90% RH at 25° C. Compound I Sesqui-Adipate Form I is triclinic crystalline form having unit cell parameters: a equal to 8.10 Å, b equal to 13.38 Å, c equal to 16.46 Å, α equal to 71.91°, β equal to 79.15° and γ equal to 76.92°.

Compound I Mono-Adipate Form I

Figure 55:
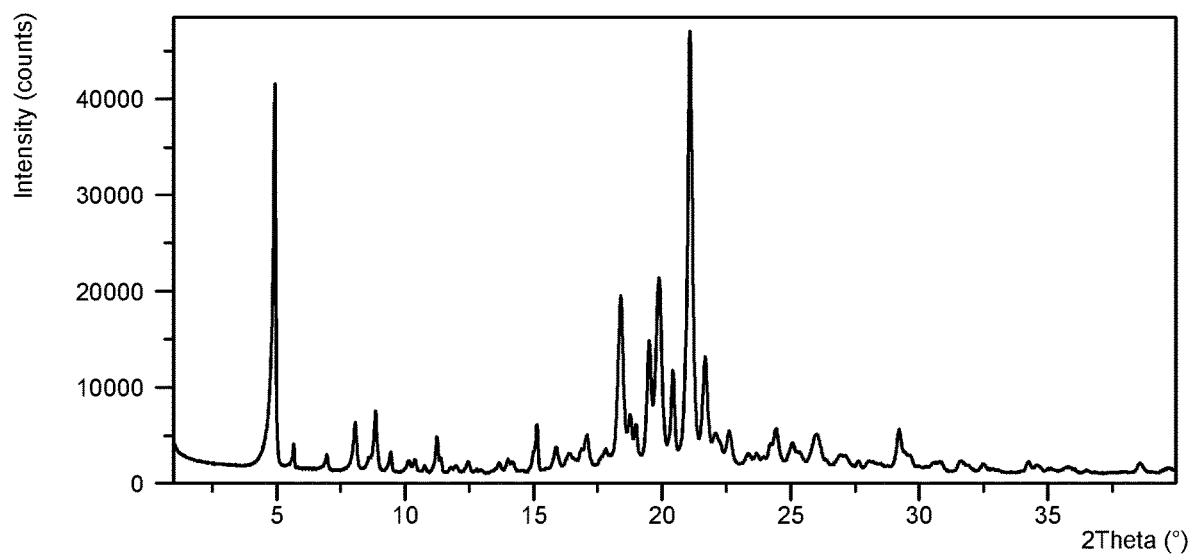
FIG. 55 is an X-ray powder diffractogram of Compound I Mono Adipate Form I.

Compound I Mono-Adipate Form I is a THF solvate. Compound I Mono-Adipate Form I can be characterized by an X-ray powder diffractogram comprising peaks (±0.2° 2θ) at 4.9, 19.9 and 21.1° 2θ, as determined on a diffractometer using Cu-Kα radiation. The diffractogram can comprise additional peaks (±0.2° 2θ) at 18.4, 19.5 and 21.7° 2θ. Compound I Mono-Adipate Form I can be characterized by an X-ray powder diffractogram as substantially shown in FIG. 55. In one embodiment, Compound I Mono-Adipate Form I can be characterized by an X-ray powder diffractogram comprising at least three, at least four or at least five peaks (±0.2° 2θ) selected from 21.1, 4.9, 19.9, 18.4, 19.5, 21.7, 20.4, 8.9 and 18.8° 2θ, as determined on a diffractometer using Cu-Kα radiation.

Figure 56:
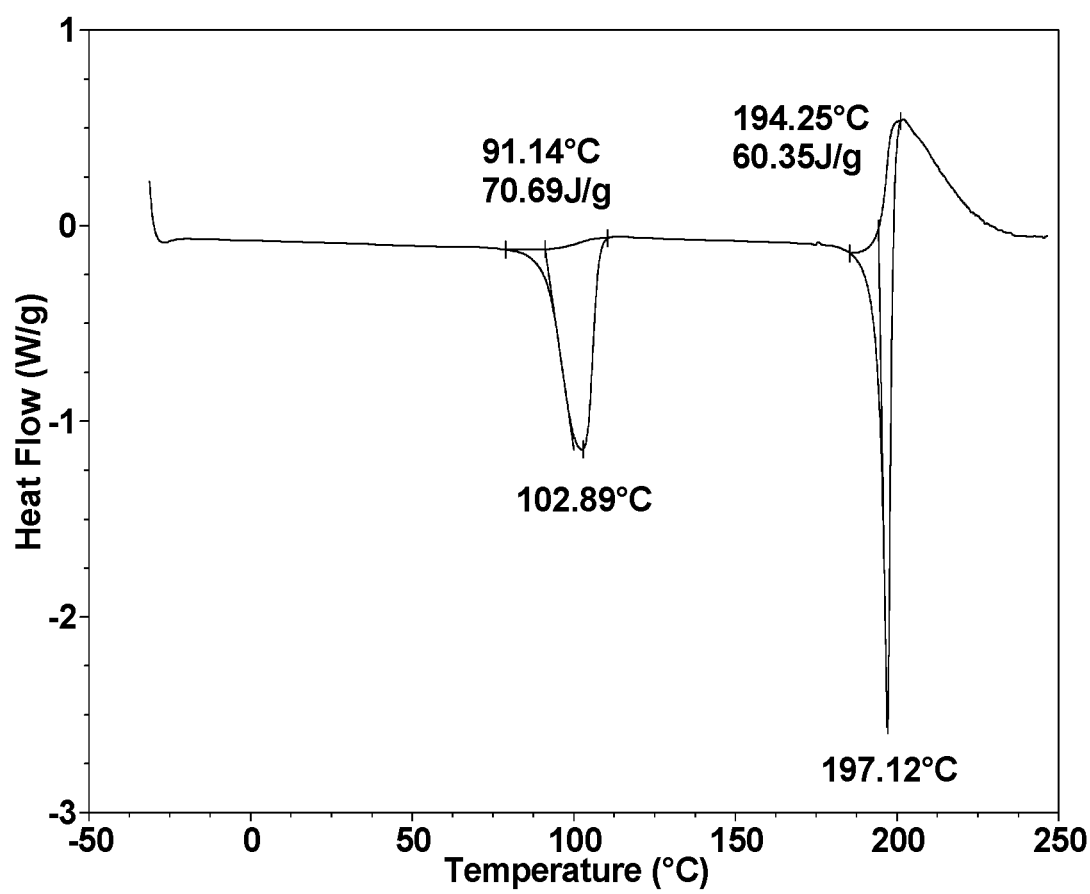
FIG. 56 is a DSC curve of Compound I Mono Adipate Form I.
Figure 57:
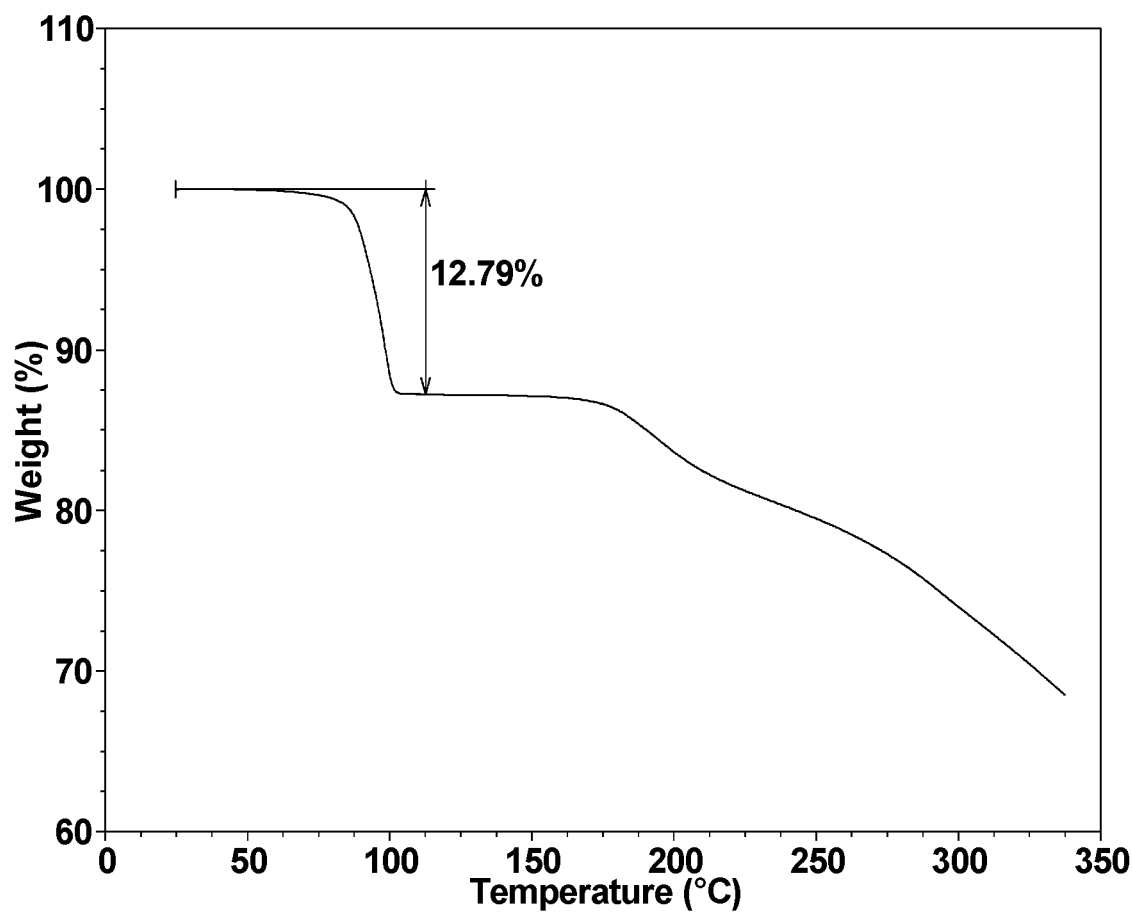
FIG. 57 is a TGA curve of Compound I Mono Adipate Form I.

In some embodiments, Compound I Mono-Adipate Form I can be characterized by a DSC curve comprising endotherms having onset temperatures of about 91° C. and 194° C. The endotherms comprise peak at about 103° C. and 197° C. In another embodiment, Compound I Mono-Adipate Form I can be characterized by a DSC curve substantially as shown in FIG. 56. In some embodiments, Compound I Mono-Adipate Form I can be characterized by a TGA curve substantially as shown in FIG. 57. Compound I Mono-Adipate Form I is monoclinic crystalline form having unit cell parameters: a equal to 11.04 Å, b equal to 31.08 Å, c equal to 22.23 Å, α equal to 90.00°, β equal to 100.23° and γ equal to 90.00°.

Compound I Bis-Citrate Form I

Figure 58:
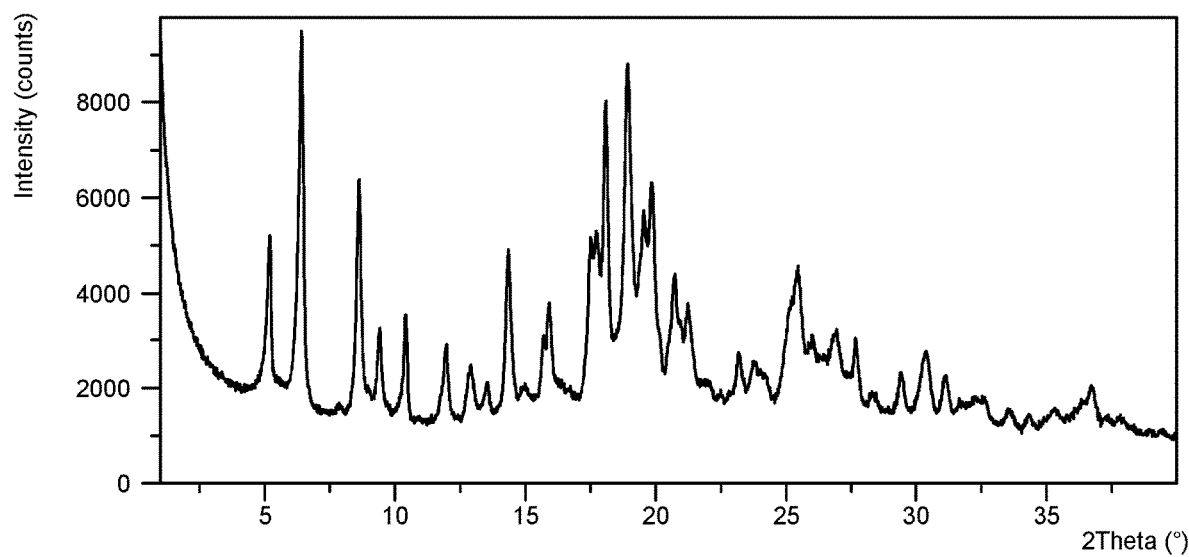
FIG. 58 is an X-ray powder diffractogram of Compound I Bis-Citrate Form I.

Compound I Bis-Citrate Form I is a THF solvate. Compound I Bis-Citrate Form I can be characterized by an X-ray powder diffractogram comprising peaks (±0.2° 2θ) at 6.4, 18.1 and 18.9° 2θ, as determined on a diffractometer using Cu-Kα radiation. The diffractogram can comprise additional peaks (±0.2° 2θ) at 8.6, 17.8 and 19.9° 2θ. Compound I Bis-Citrate Form I can be characterized by an X-ray powder diffractogram as substantially shown in FIG. 58. In one embodiment, Compound I Bis-Citrate Form I can be characterized by an X-ray powder diffractogram comprising at least three, at least four or at least five peaks (±0.2° 2θ) selected from 6.4, 18.9, 18.1, 8.6, 19.9, 19.5, 17.8, 17.5 and 14.3° 2θ, as determined on a diffractometer using Cu-Kα radiation.

Figure 59:
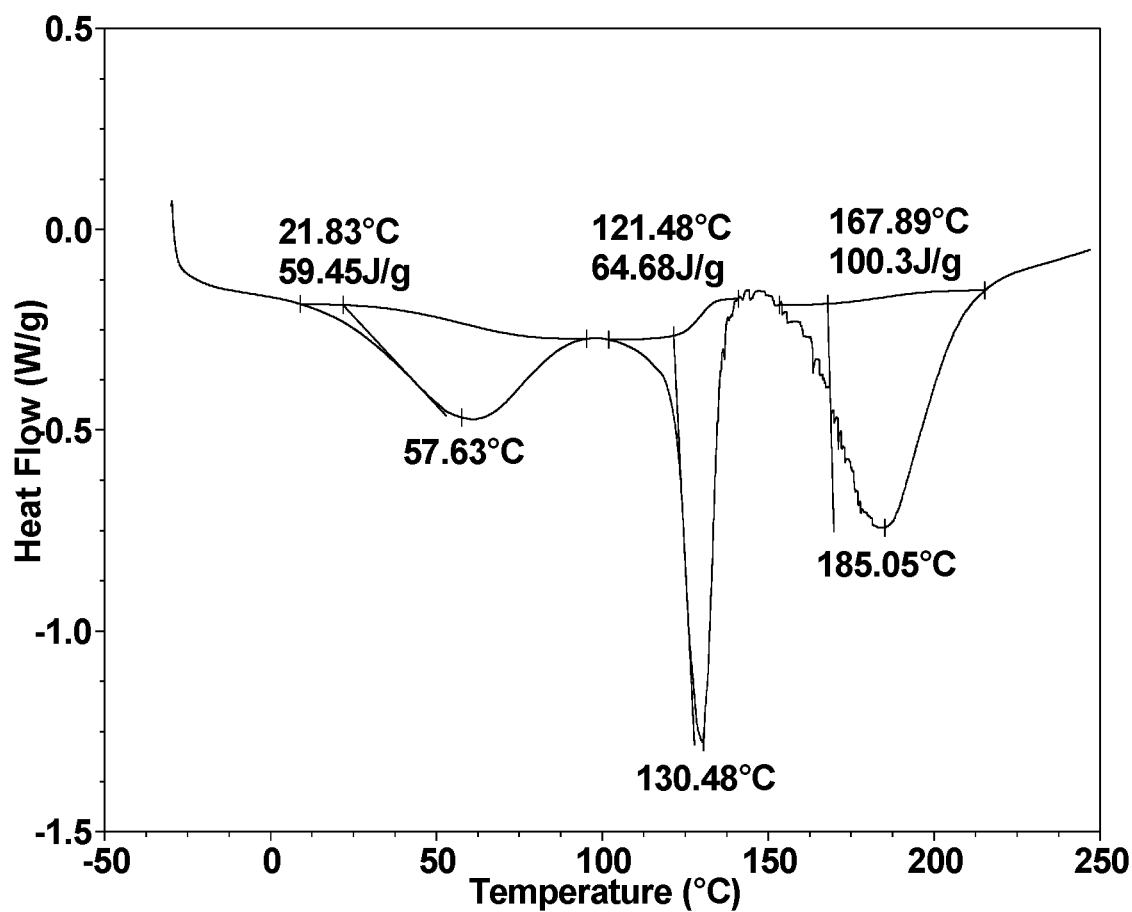
FIG. 59 is a DSC curve of Compound I Bis-Citrate Form I.
Figure 60:
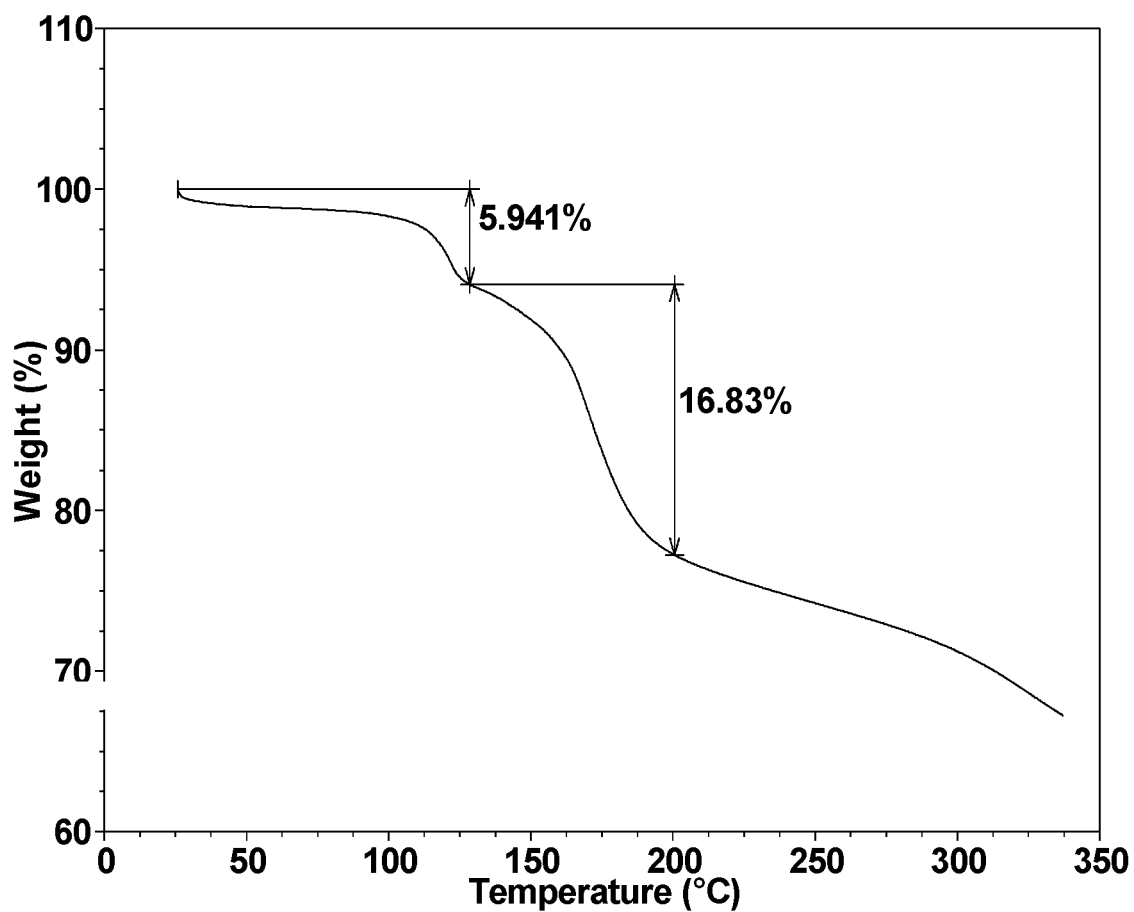
FIG. 60 is a TGA curve of Compound I Bis-Citrate Form I.

In some embodiments, Compound I Bis-Citrate Form I can be characterized by a DSC curve comprising a broad endotherm between temperatures of about 22° C. and 87° C. The DSC curve can further comprise endotherms having onset temperature of about 121° C. and 168° C. In another embodiment, Compound I Bis-Citrate Form I can be characterized by a DSC curve is substantially as shown in FIG. 59. In some embodiments, Compound I Bis-Citrate Form I can be characterized by a TGA curve substantially as shown in FIG. 60.

Compound I Sesqui-Fumarate Form I

Figure 61:
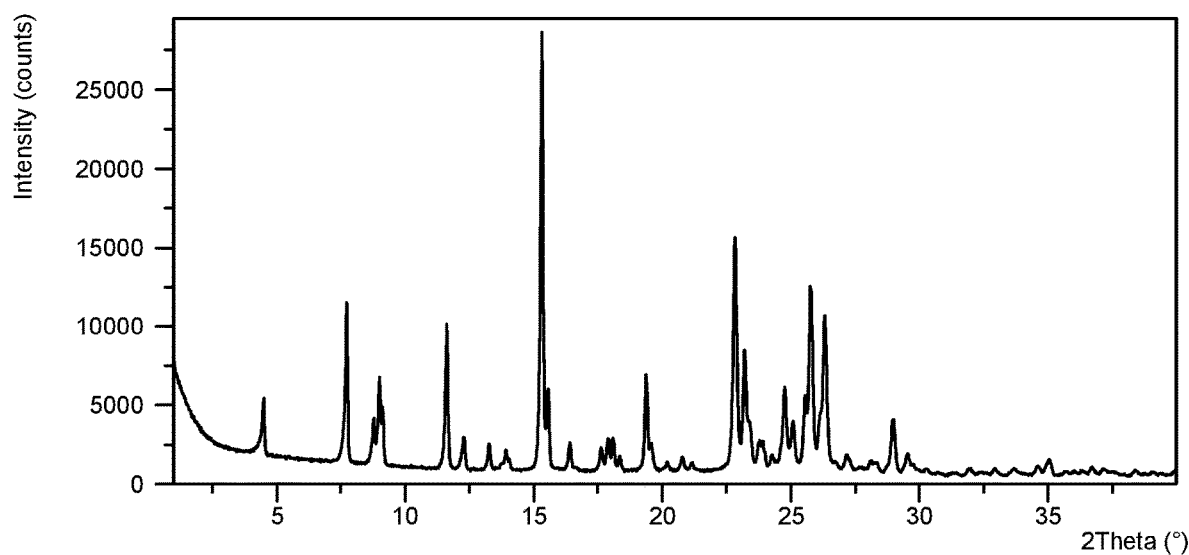
FIG. 61 is an X-ray powder diffractogram of Compound I Sesqui-Fumarate Form I.

Compound I Sesqui-Fumarate Form I can be characterized by an X-ray powder diffractogram comprising peaks (±0.2° 2θ) at 15.3, 22.8 and 25.8° 2θ, as determined on a diffractometer using Cu-Kα radiation. The diffractogram can comprise additional peaks (±0.2° 2θ) at 7.8, 11.6 and 26.3° 2θ. Compound I Sesqui-Fumarate Form I can be characterized by an X-ray powder diffractogram as substantially shown in FIG. 61. In one embodiment, Compound I Sesqui-Fumarate Form I can be characterized by an X-ray powder diffractogram comprising at least three, at least four or at least five peaks (±0.2° 2θ) selected from 15.3, 22.8, 25.8, 7.8, 26.3, 11.6, 23.2, 19.4 and 9.0° 2θ, as determined on a diffractometer using Cu-Kα radiation.

Figure 62:
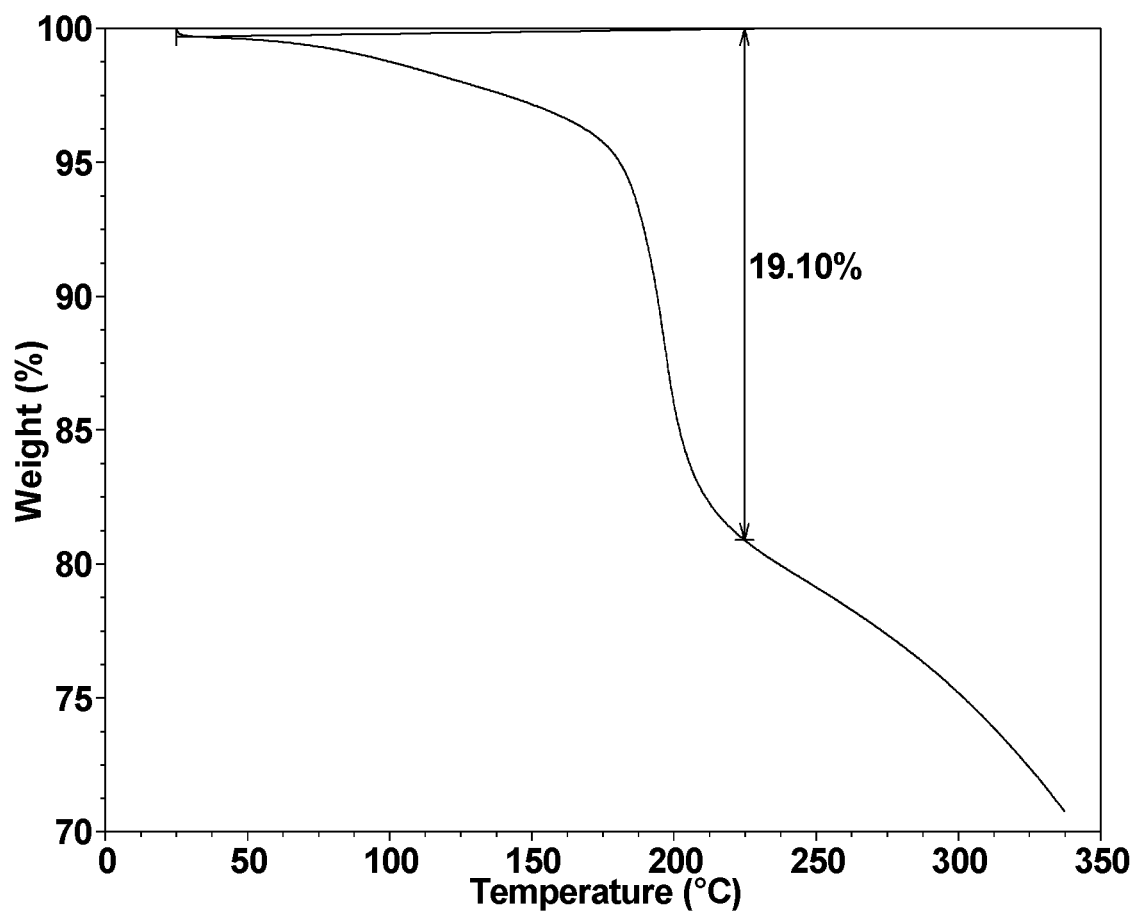
FIG. 62 is a TGA curve of Compound I Sesqui-Fumarate Form I.

In some embodiments, Compound I Sesqui-Fumarate Form I can be characterized by a TGA curve substantially as shown in FIG. 62.

Compound I Bis-Gentisate Form I

Figure 63:
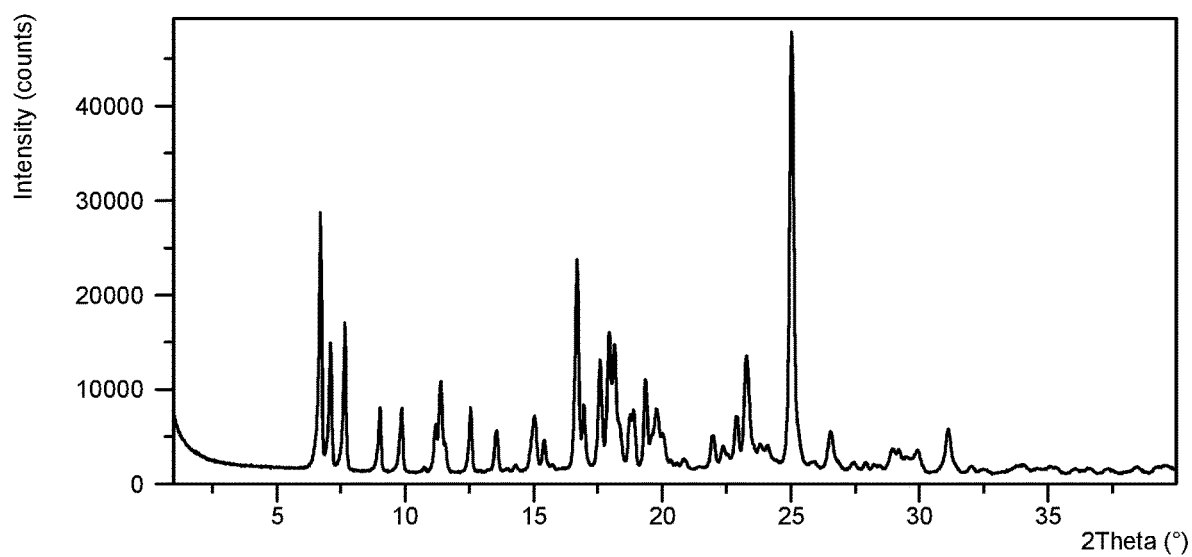
FIG. 63 is an X-ray powder diffractogram of Compound I Bis-Gentisate Form I.

Compound I Bis-Gentisate Form I is a THF solvate. Compound I Bis-Gentisate Form I can be characterized by an X-ray powder diffractogram comprising peaks (±0.2° 2θ) at 6.7, 16.7 and 25.0° 2θ, as determined on a diffractometer using Cu-Kα radiation. The diffractogram can comprise additional peaks (±0.2° 2θ) at 7.7, 17.9 and 23.3° 2θ. Compound I Bis-Gentisate Form I can be characterized by an X-ray powder diffractogram as substantially shown in FIG. 63. In one embodiment, Compound I Bis-Gentisate Form I can be characterized by an X-ray powder diffractogram comprising at least three, at least four or at least five peaks (±0.2° 2θ) selected from 25.0, 6.7, 16.7, 7.7, 17.9, 23.3, 18.2, 7.1 and 17.6° 2θ, as determined on a diffractometer using Cu-Kα radiation.

Figure 64:
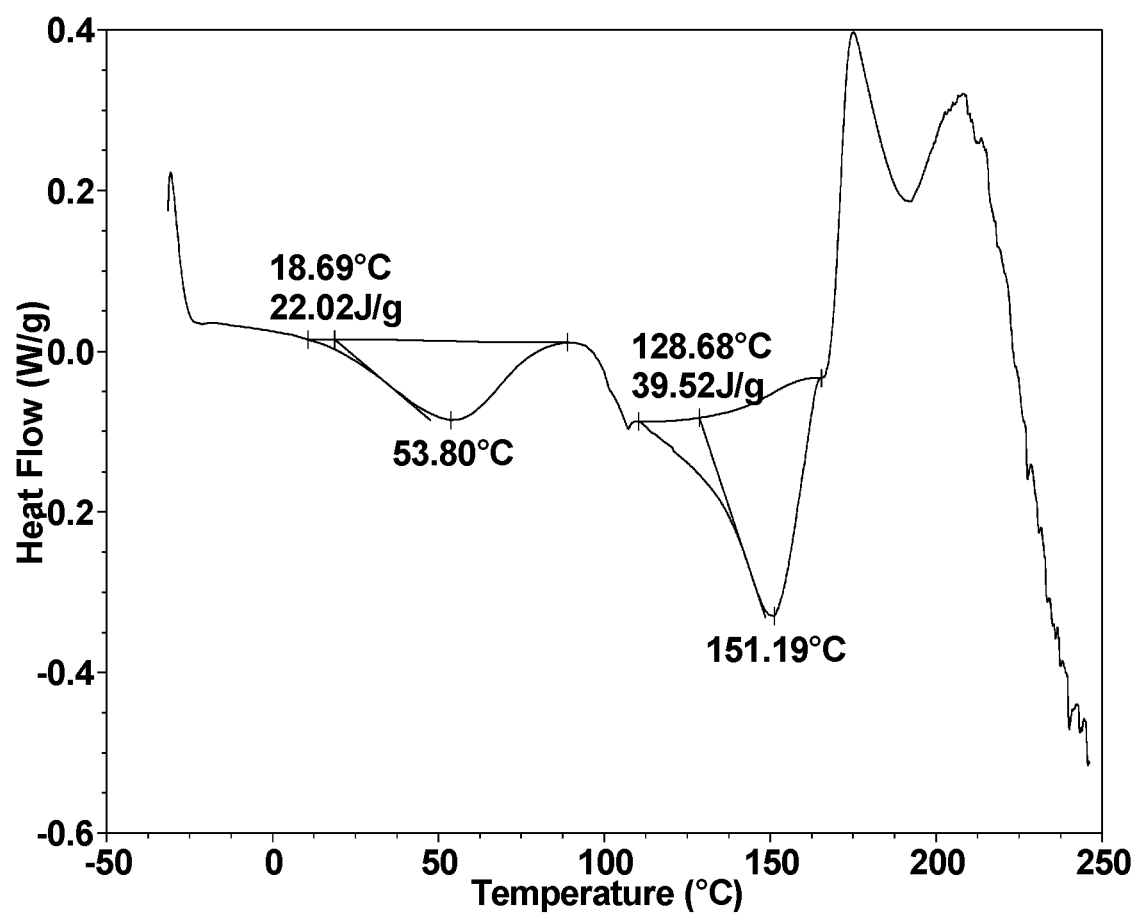
FIG. 64 is a DSC curve of Compound I Bis-Gentisate Form I.
Figure 65:
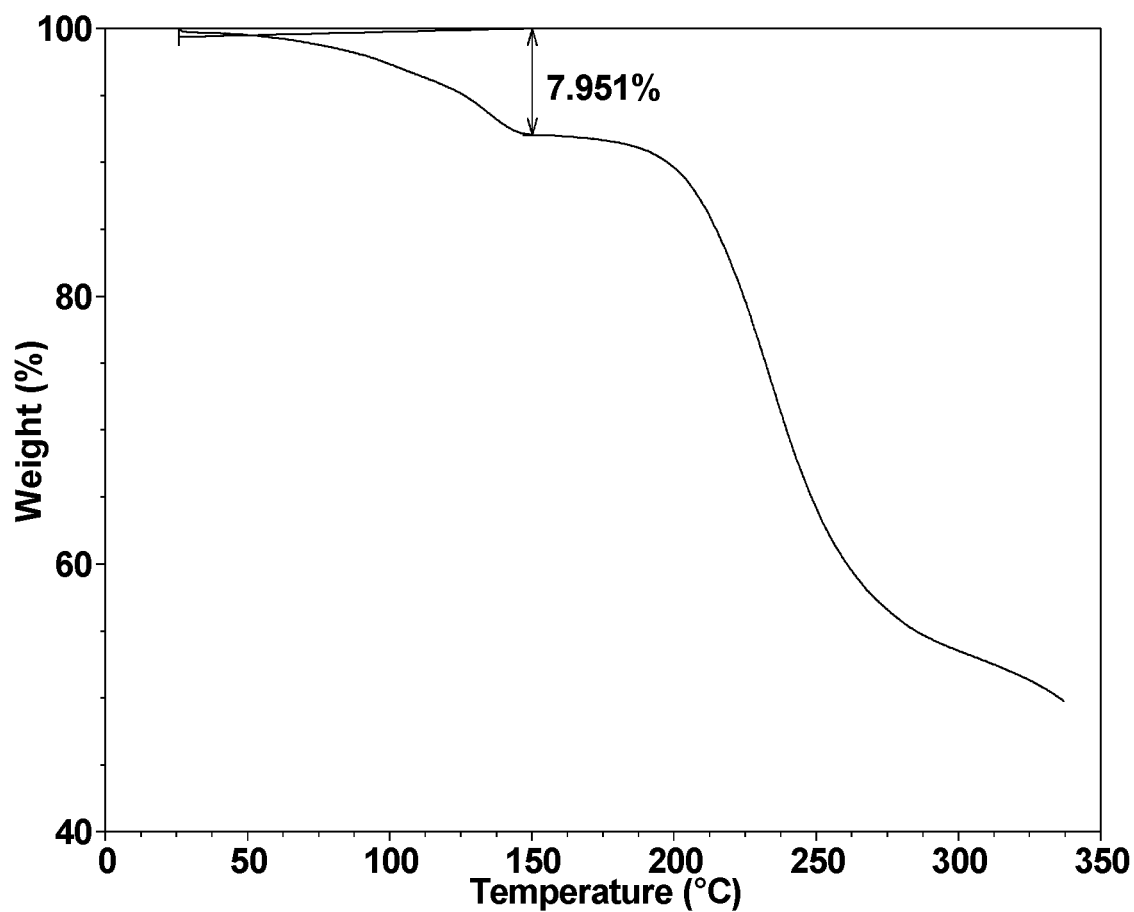
FIG. 65 is a TGA curve of Compound I Bis-Gentisate Form I.

In some embodiments, Compound I Bis-Gentisate Form I can be characterized by a DSC curve comprising endotherms having peaks at about 54° C. and 151° C. In another embodiment, Compound I Bis-Gentisate Form I can be characterized by a DSC curve substantially as shown in FIG. 64. In some embodiments, Compound I Bis-Gentisate Form I can be characterized by a TGA curve substantially as shown in FIG. 65. Compound I Bis-Gentisate Form I is a triclinic crystalline form having unit cell parameters: a equal to 12.06 Å, b equal to 13.73 Å, c equal to 14.88 Å, α equal to 64.57°, β equal to 73.71° and γ equal to 77.01°.

Compound I Mono-BSA Form I

Figure 66:
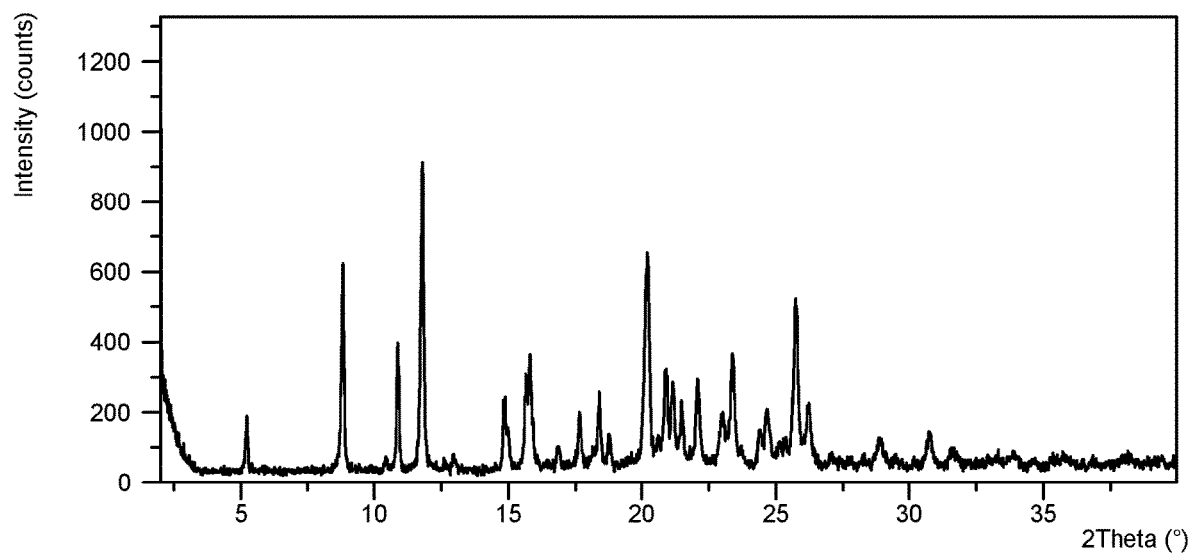
FIG. 66 is an X-ray powder diffractogram of Compound I Mono-BSA Salt Form I.

Compound I Mono-BSA Form I is a hydrated form. Compound I Mono-BSA Form I can be characterized by an X-ray powder diffractogram comprising peaks (±0.2° 2θ) at 8.8, 11.8 and 20.2° 2θ, as determined on a diffractometer using Cu-Kα radiation. The diffractogram can comprise additional peaks (±0.2° 2θ) at 10.9, 15.8 and 25.7° 2θ. Compound I Mono-BSA Form I can be characterized by an X-ray powder diffractogram as substantially shown in FIG. 66. In one embodiment, Compound I Mono-BSA Form I can be characterized by an X-ray powder diffractogram comprising at least three, at least four or at least five peaks (±0.2° 2θ) selected from 11.8, 8.8, 20.2, 25.7, 10.9, 15.8, 23.4, 20.9 and 21.2° 2θ, as determined on a diffractometer using Cu-Kα radiation.

Figure 67:
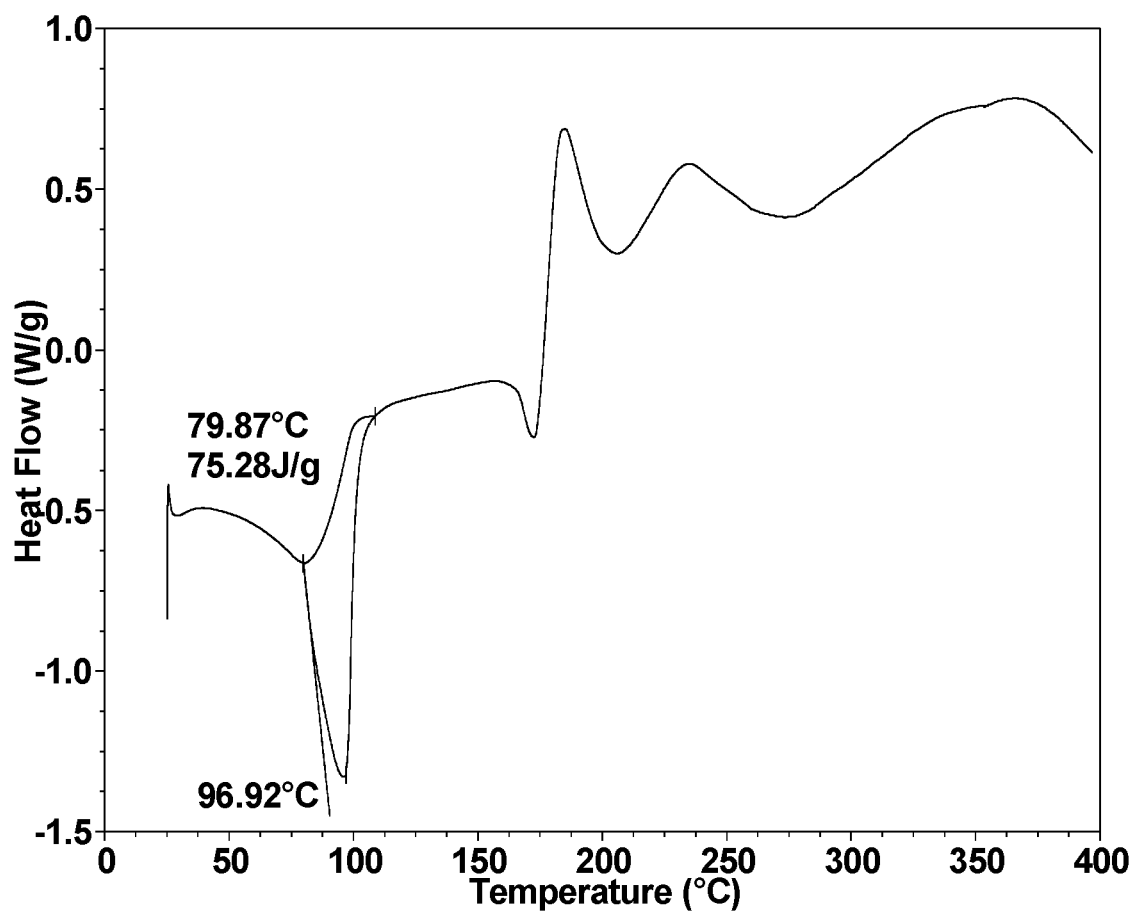
FIG. 67 is a DSC curve of Compound I Mono-BSA Salt Form I.
Figure 68:
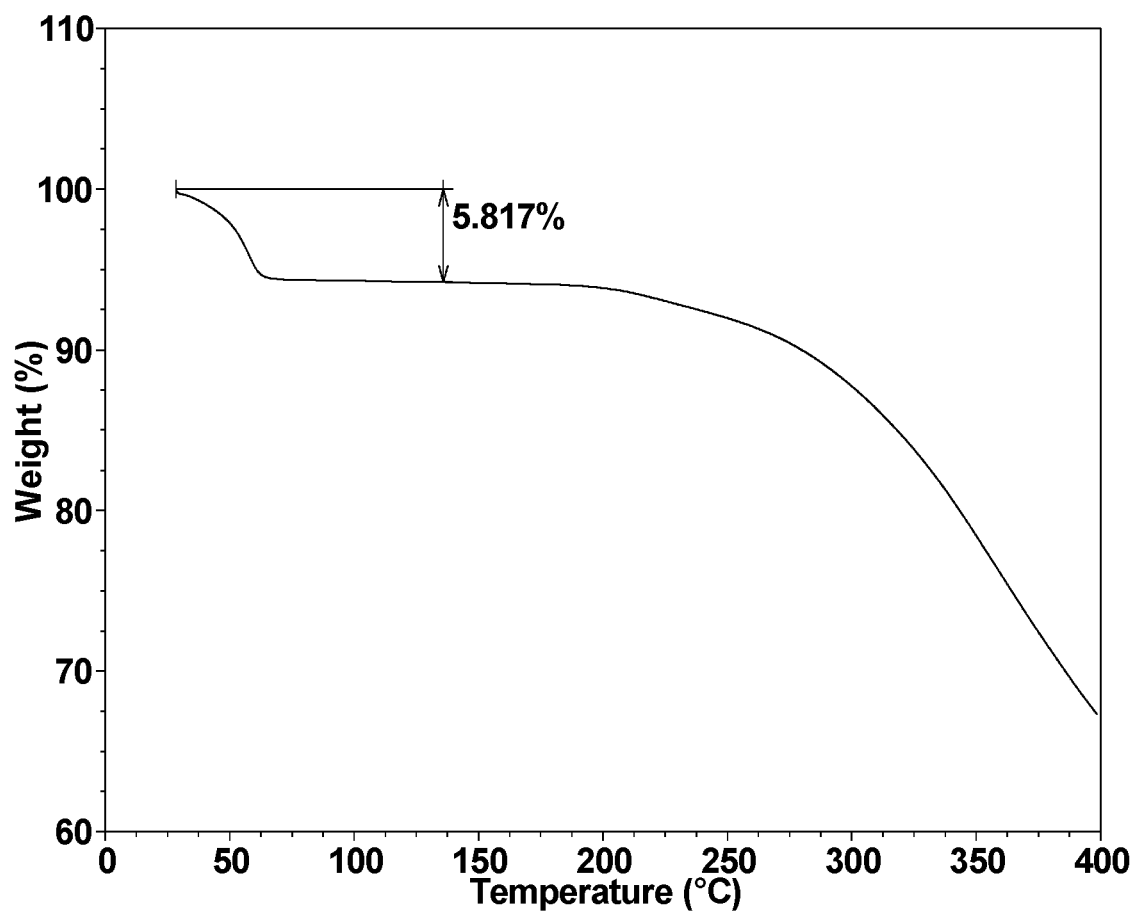
FIG. 68 is a TGA curve of Compound I Mono-BSA Salt Form I.
Figure 69:
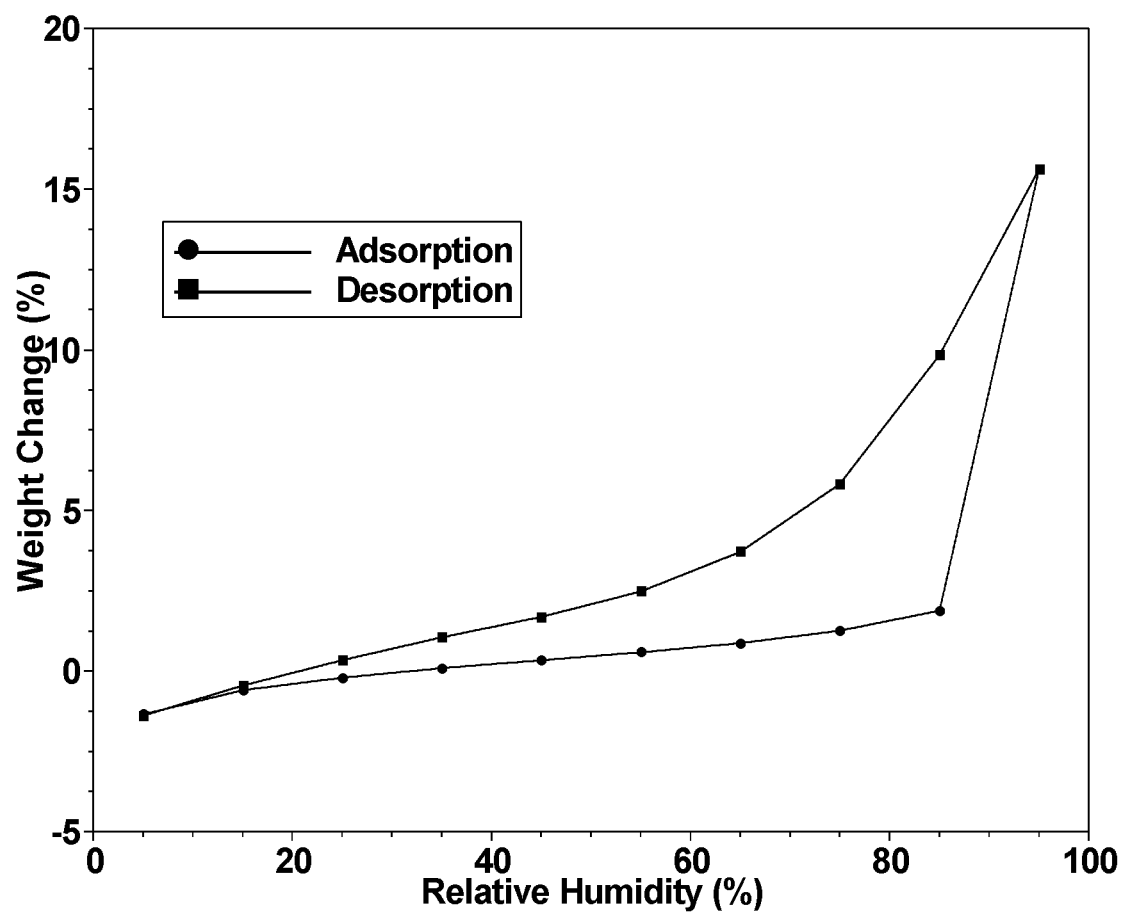
FIG. 69 is a DVS curve of Compound I Mono-BSA Salt Form I.

In some embodiments, Compound I Mono-BSA Form I can be characterized by a DSC curve comprising an endotherm having an onset temperature of about 80° C. The endotherm can comprise a peak at about 97° C. In another embodiment, Compound I Mono-BSA Form I can be characterized by a DSC curve substantially as shown in FIG. 67. In some embodiments, Compound I Mono-BSA Form I can be characterized by a TGA curve substantially as shown in FIG. 68. In some embodiments, Compound I Mono-BSA Form I can be characterized by a DVS curve substantially as shown in FIG. 69. DVS analysis shows that it is slightly hygroscopic, picks up about 1.5 wt. % of water at 85% RH at 25° C. However, it is very hygroscopic above 85% RH as there is a >15 wt. % change at 95% RH and 25° C. which lead to deliquescence.

Compound I Sesqui-Oxalate Form I

Figure 70:
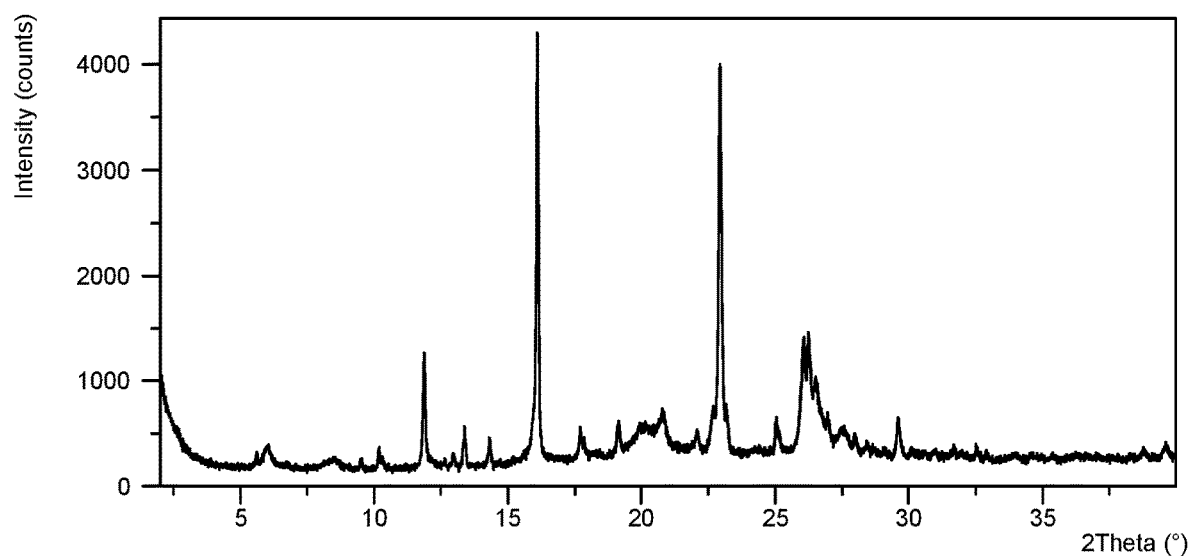
FIG. 70 is an X-ray powder diffractogram of Compound I Sesqui-Oxalate Form I.

Compound I Sesqui-Oxalate Form I can be characterized by an X-ray powder diffractogram comprising peaks (±0.2° 2θ) at 16.1, 23.0 and 26.1° 2θ, as determined on a diffractometer using Cu-Kα radiation. The diffractogram can comprise additional peaks (±0.2° 2θ) at 11.9, 19.2 and 20.8° 2θ. Compound I Sesqui-Oxalate Form I can be characterized by an X-ray powder diffractogram as substantially shown in FIG. 70. In one embodiment, Compound I Sesqui-Oxalate Form I can be characterized by an X-ray powder diffractogram comprising at least three, at least four or at least five peaks (±0.2° 2θ) selected from 16.1, 23.0, 26.1, 11.9, 20.8, 19.2, 20.0, 25.1 and 17.7° 2θ, as determined on a diffractometer using Cu-Kα radiation.

Figure 71:
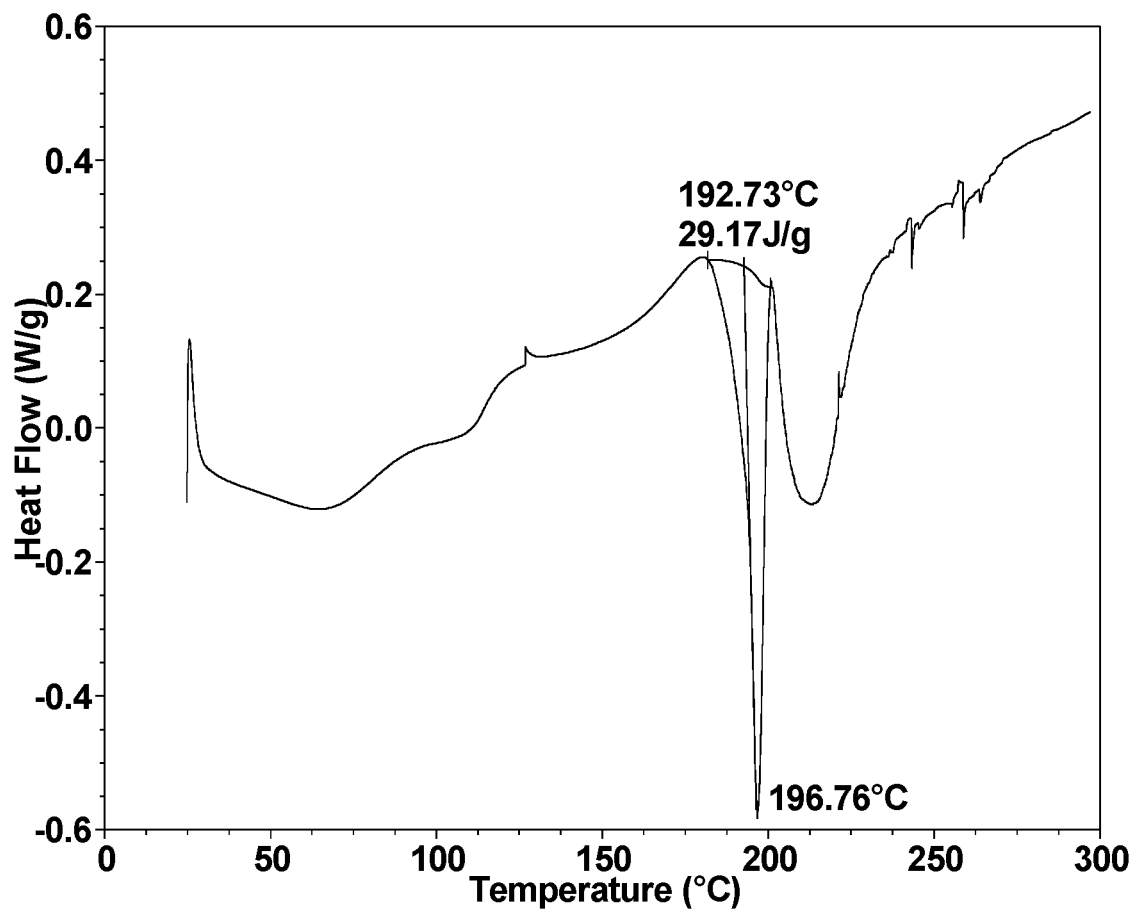
FIG. 71 is a DSC curve of Compound I Sesqui-Oxalate Form I.
Figure 72:
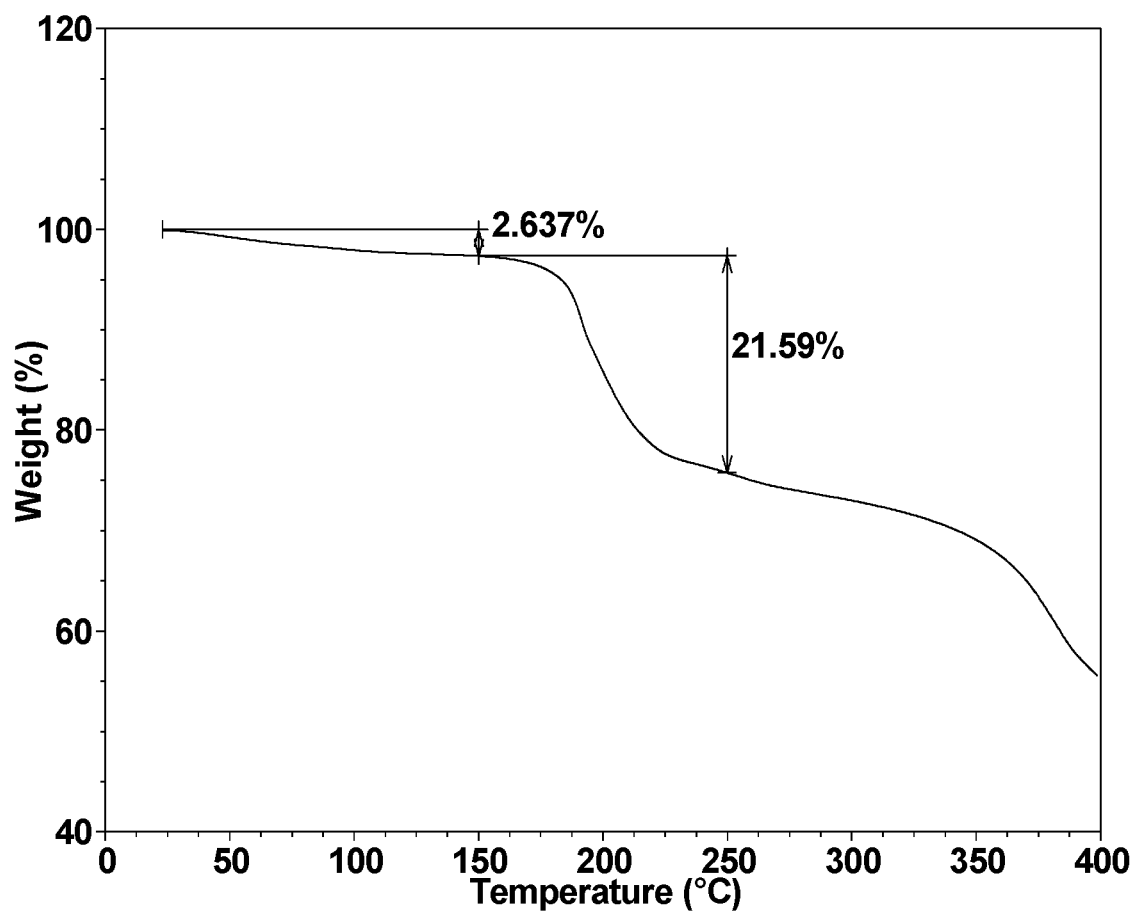
FIG. 72 is a TGA curve of Compound I Sesqui-Oxalate Form I.

In some embodiments, Compound I Sesqui-Oxalate Form I can be characterized by a DSC curve comprising an endotherm having an onset temperature of about 193° C. The endotherm can comprise a peak at about 197° C. In another embodiment, Compound I Sesqui-Oxalate Form I can be characterized by a DSC curve substantially as shown in FIG. 71. In some embodiments, Compound I Sesqui-Oxalate Form I can be characterized by a TGA curve substantially as shown in FIG. 72.

Compound I HCl Material A

Figure 78:
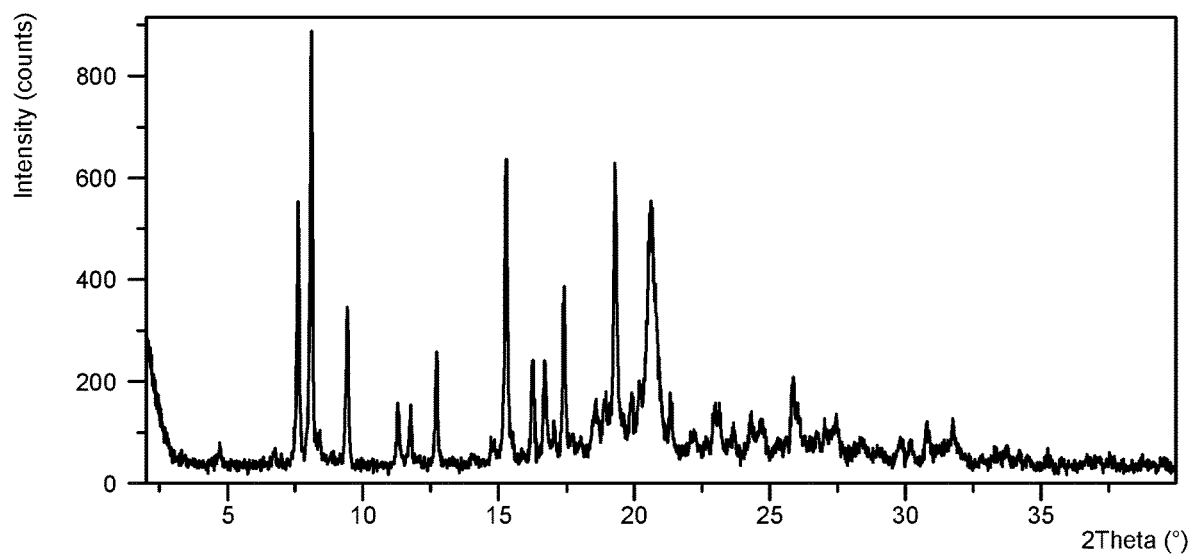
FIG. 78 is an X-ray powder diffractogram of Compound I HCl Material A.

Compound I HCl Material A can be characterized by an X-ray powder diffractogram comprising peaks (±0.2° 2θ) at 8.1, 15.3 and 19.3° 2θ, as determined on a diffractometer using Cu-Kα radiation. The diffractogram can comprise additional peaks (±0.2° 2θ) at 7.6, 17.4 and 20.6° 2θ. Compound I HCl Material A can be characterized by an X-ray powder diffractogram as substantially shown in FIG. 78. In one embodiment, Compound I HCl Material A can be characterized by an X-ray powder diffractogram comprising at least three, at least four or at least five peaks (±0.2° 2θ) selected from 8.1, 15.3, 19.3, 7.6, 20.6, 17.4, 9.4, 12.7 and 16.7° 2θ, as determined on a diffractometer using Cu-Kα radiation.

Compound I HCl Material B

Compound I HCl Material B can be characterized by an X-ray powder diffractogram comprising peaks (±0.2° 2θ) at 17.7, 19.6 and 22.6° 2θ, as determined on a diffractometer using Cu-Kα radiation. The diffractogram can comprise additional peaks (±0.2° 2θ) at 20.0, 21.9 and 25.7° 2θ. Compound I HCl Material B can be characterized by an X-ray powder diffractogram as substantially shown in FIG.

79. In one embodiment, Compound I HCl Material B can be characterized by an X-ray powder diffractogram comprising at least three, at least four or at least five peaks (±0.2° 2θ) selected from 19.6, 22.6, 17.7, 20.0, 25.7, 21.9, 10.0, 26.0 and 27.6° 2θ, as determined on a diffractometer using Cu-Kα radiation.

Synthesis of Compound I

Compound I can be synthesized according to methods known to persons skilled in the art, such as the synthetic procedure described in Example 1.

Formulations and Administration

Crystalline forms of Compound I or crystalline forms of a salt or a co-crystal of Compound I are usually administered in the form of pharmaceutical compositions. This disclosure therefore provides pharmaceutical compositions that contain, as the active ingredient, one or more of the crystalline forms described and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

In some embodiments, a pharmaceutical composition comprises crystalline forms of Compound I or crystalline forms of a salt or a co-crystal of Compound I, or combinations thereof. In some embodiments, a pharmaceutical composition comprises Compound I Form I, Compound I Form II, Compound I Form III, Compound I Form IV, Compound I Form V, Compound I Form VII, Compound I Form VIII, Compound I Form IX, Compound I Form X, Compound I Form XI, Compound I Form XII, Compound I Form XIII, Compound I Form XIV, Compound I Sesqui-Succinate Form III, Compound I Sesqui-Succinate Form IV, Compound I Sesqui-Succinate Form V, Compound I Hemi-Succinate Form I, Compound I Mono-HCl salt Form I, Compound I Mono-HCl salt Form II, Compound I Mono-HCl salt Form III, Compound I Sesqui-Adipate Form I, Compound I Mono-Adipate Form I, Compound I Bis-Citrate Form I, Compound I Sesqui-Fumarate Form I, Compound I Bis-Gentisate Form I, Compound I Mono-BSA salt Form I or Compound I Sesqui-Oxalate Form I.

In some embodiments, a pharmaceutical composition comprises a compound of Formula I, wherein at least 95% of Formula I is Compound I Form I, and no more than 5%, 4%, 3%, 2% or 1% of other forms. In some embodiments, a pharmaceutical composition comprises a compound of Formula I, wherein at least 95% of Formula I is Compound I Form II, and no more than 5%, 4%, 3%, 2% or 1% of other forms. In some embodiments, a pharmaceutical composition comprises a compound of Formula I, wherein at least 95% of Formula I is Compound I Form III, and no more than 5%, 4%, 3%, 2% or 1% of other forms. In some embodiments, a pharmaceutical composition comprises a compound of Formula I, wherein at least 95% of Formula I is Compound I Form IV, and no more than 5%, 4%, 3%, 2% or 1% of other forms. In some embodiments, a pharmaceutical composition comprises a compound of Formula I, wherein at least 95% of Formula I is Compound I Form V, and no more than 5%, 4%, 3%, 2% or 1% of other forms. In some embodiments, a pharmaceutical composition comprises a compound of Formula I, wherein at least 95% of Formula I is Compound I Form V, and no more than 5%, 4%, 3%, 2% or 1% of other forms. In some embodiments, a pharmaceutical composition comprises a compound of Formula I, wherein at least 95% of Formula I is Compound I Form VI, and no more than 5%, 4%, 3%, 2% or 1% of other forms. In some embodiments, a pharmaceutical composition comprises a compound of Formula I, wherein at least 95% of Formula I is Compound I Form VII, and no more than 5%, 4%, 3%, 2% or 1% of other forms. In some embodiments, a pharmaceutical composition comprises a compound of Formula I, wherein at least 95% of Formula I is Compound I Form VIII, and no more than 5%, 4%, 3%, 2% or 1% of other forms. In some embodiments, a pharmaceutical composition comprises a compound of Formula I, wherein at least 95% of Formula I is Compound I Form IX, and no more than 5%, 4%, 3%, 2% or 1% of other forms. In some embodiments, a pharmaceutical composition comprises a compound of Formula I, wherein at least 95% of Formula I is Compound I Form X, and no more than 5%, 4%, 3%, 2% or 1% of other forms. In some embodiments, a pharmaceutical composition comprises a compound of Formula I, wherein at least 95% of Formula I is Compound I Form XI, and no more than 5%, 4%, 3%, 2% or 1% of other forms. In some embodiments, a pharmaceutical composition comprises a compound of Formula I, wherein at least 95% of Formula I is Compound I Form XII, and no more than 5%, 4%, 3%, 2% or 1% of other forms. In some embodiments, a pharmaceutical composition comprises a compound of Formula I, wherein at least 95% of Formula I is Compound I Form XIII, and no more than 5%, 4%, 3%, 2% or 1% of other forms. In some embodiments, a pharmaceutical composition comprises a compound of Formula I, wherein at least 95% of Formula I is Compound I Form XIV, and no more than 5%, 4%, 3%, 2% or 1% of other forms.

In some embodiments, a pharmaceutical composition comprises a compound of Formula I, wherein at least 95% of Formula I is Compound I Sesqui-Succinate Form III, and no more than 5%, 4%, 3%, 2% or 1% of other forms. In some embodiments, a pharmaceutical composition comprises a compound of Formula I, wherein at least 95% of Formula I is Compound I Sesqui-Succinate Form IV, and no more than 5%, 4%, 3%, 2% or 1% of other forms. In some embodiments, a pharmaceutical composition comprises a compound of Formula I, wherein at least 95% of Formula I is Compound I Sesqui-Succinate Form V, and no more than 5%, 4%, 3%, 2% or 1% of other forms. In some embodiments, a pharmaceutical composition comprises a compound of Formula I, wherein at least 95% of Formula I is Compound I Hemi-Succinate Form I, and no more than 5%, 4%, 3%, 2% or 1% of other forms. In some embodiments, a pharmaceutical composition comprises a compound of Formula I, wherein at least 95% of Formula I is Compound I Mono-HCl salt Form I, and no more than 5%, 4%, 3%, 2% or 1% of other forms. In some embodiments, a pharmaceutical composition comprises a compound of Formula I, wherein at least 95% of Formula I is Compound I Mono-HCl salt Form II, and no more than 5%, 4%, 3%, 2% or 1% of other forms. In some embodiments, a pharmaceutical composition comprises a compound of Formula I, wherein at least 95% of Formula I is Compound I Mono-HCl salt Form III, and no more than 5%, 4%, 3%, 2% or 1% of other forms. In some embodiments, a pharmaceutical composition comprises a compound of Formula I, wherein at least 95% of Formula I is Compound I Sesqui-Adipate Form I, and no more than 5%, 4%, 3%, 2% or 1% of other forms. In some embodiments, a pharmaceutical composition comprises a compound of Formula I, wherein at least 95% of Formula I is Compound I Mono-Adipate Form I, and no more than 5%, 4%, 3%, 2% or 1% of other forms. In some embodiments, a pharmaceutical composition comprises a compound of Formula I, wherein at least 95% of Formula I is Compound I Bis-Citrate Form I, and no more than 5%, 4%, 3%, 2% or 1% of other forms. In some embodiments, a pharmaceutical composition comprises a compound of Formula I, wherein at least 95% of Formula I is Compound I Sesqui-Fumarate Form I, and no more than 5%, 4%, 3%, 2% or 1% of other forms. In some embodiments, a pharmaceutical composition comprises a compound of Formula I, wherein at least 95% of Formula I is Compound I Bis-Gentisate Form I, and no more than 5%, 4%, 3%, 2% or 1% of other forms. In some embodiments, a pharmaceutical composition comprises a compound of Formula I, wherein at least 95% of Formula I is Compound I Mono-BSA salt Form I, and no more than 5%, 4%, 3%, 2% or 1% of other forms. In some embodiments, a pharmaceutical composition comprises a compound of Formula I, wherein at least 95% of Formula I is Compound I Sesqui-Oxalate Form I, and no more than 5%, 4%, 3%, 2% or 1% of other forms.

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the crystalline forms of Compound I or the crystalline forms of a salt or a co-crystal of Compound I may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions can be prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which can yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of a crystalline form as described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the of a crystalline form as described herein. Administration may be via capsule or enteric coated tablets, or the like. In making the pharmaceutical compositions that include crystalline forms of Compound I or the crystalline forms of a salt or co-crystal of Compound I, the active ingredient can be diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions described herein are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 1 mg to about 5000 mg, about 1 mg to about 4000 mg, about 1 mg to about 3000 mg, about 1 mg to about 2000 mg, about 2 mg to about 2000 mg, about 5 mg to about 2000 mg, about 10 mg to about 2000 mg, about 1 mg to about 1000 mg, about 2 mg to about 1000 mg, about 5 mg to about 1000 mg, about 10 mg to about 1000 mg, about 25 mg to about 1000 mg, about 50 mg to about 1000 mg, about 75 mg to about 1000 mg, about 100 mg to about 1000 mg, about 125 mg to about 1000 mg, about 150 mg to about 1000 mg, about 175 mg to about 1000 mg, about 200 mg to about 1000 mg, about 225 mg to about 1000 mg, about 250 mg to about 1000 mg, about 300 mg to about 1000 mg, about 350 mg to about 1000 mg, about 400 mg to about 1000 mg, about 450 mg to about 1000 mg, about 500 mg to about 1000 mg, about 550 mg to about 1000 mg, about 600 mg to about 1000 mg, about 650 mg to about 1000 mg, about 700 mg to about 1000 mg, about 750 mg to about 1000 mg, about 800 mg to about 1000 mg, about 850 mg to about 1000 mg, about 900 mg to about 1000 mg, about 950 mg to about 1000 mg, about 1 mg to about 750 mg, about 2 mg to about 750 mg, about 5 mg to about 750 mg, about 10 mg to about 750 mg, about 25 mg to about 750 mg, about 50 mg to about 750 mg, about 75 mg to about 750 mg, about 100 mg to about 750 mg, about 125 mg to about 750 mg, about 150 mg to about 750 mg, about 175 mg to about 750 mg, about 200 mg to about 750 mg, about 225 mg to about 750 mg, about 250 mg to about 750 mg, about 300 mg to about 750 mg, about 350 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, about 700 mg to about 750 mg, about 1 mg to about 500 mg, about 2 mg to about 500 mg, about 5 mg to about 500 mg, about 10 mg to about 500 mg, about 25 mg to about 500 mg, about 50 mg to about 500 mg, about 75 mg to about 500 mg, about 100 mg to about 500 mg, about 125 mg to about 500 mg, about 150 mg to about 500 mg, about 175 mg to about 500 mg, about 200 mg to about 500 mg, about 225 mg to about 500 mg, about 250 mg to about 500 mg, about 300 mg to about 500 mg, about 350 mg to about 500 mg, about 400 mg to about 500 mg, about 450 mg to about 500 mg, about 1 mg to about 400 mg, about 2 mg to about 400 mg, about 5 mg to about 400 mg, about 10 mg to about 400 mg, about 25 mg to about 400 mg, about 50 mg to about 400 mg, about 75 mg to about 400 mg, about 100 mg to about 400 mg, about 125 mg to about 400 mg, about 150 mg to about 400 mg, about 175 mg to about 400 mg, about 200 mg to about 400 mg, about 225 mg to about 400 mg, about 250 mg to about 400 mg, about 300 mg to about 400 mg, about 350 mg to about 400 mg, about 1 mg to about 300 mg, about 2 mg to about 300 mg, about 5 mg to about 300 mg, about 10 mg to about 300 mg, about 25 mg to about 300 mg, about 50 mg to about 300 mg, about 75 mg to about 300 mg, about 100 mg to about 300 mg, about 125 mg to about 300 mg, about 150 mg to about 300 mg, about 175 mg to about 300 mg, about 200 mg to about 300 mg, about 225 mg to about 300 mg, about 250 mg to about 300 mg, about 1 mg to about 250 mg, about 2 mg to about 250 mg, about 5 mg to about 250 mg, about 10 mg to about 250 mg, about 25 mg to about 250 mg, about 50 mg to about 250 mg, about 75 mg to about 250 mg, about 100 mg to about 250 mg, about 125 mg to about 250 mg, about 150 mg to about 250 mg, about 175 mg to about 250 mg, about 200 mg to about 250 mg, about 225 mg to about 250 mg, about 1 mg to about 225 mg, about 2 mg to about 225 mg, about 5 mg to about 225 mg, about 10 mg to about 225 mg, about 25 mg to about 225 mg, about 50 mg to about 225 mg, about 75 mg to about 225 mg, about 100 mg to about 225 mg, about 125 mg to about 225 mg, about 150 mg to about 225 mg, about 175 mg to about 225 mg, about 200 mg to about 225 mg, about 1 mg to about 200 mg, about 2 mg to about 200 mg, about 5 mg to about 200 mg, about 10 mg to about 200 mg, about 25 mg to about 200 mg, about 50 mg to about 200 mg, about 75 mg to about 200 mg, about 100 mg to about 200 mg, about 125 mg to about 200 mg, about 150 mg to about 200 mg, about 175 mg to about 200 mg, about 1 mg to about 175 mg, about 2 mg to about 175 mg, about 5 mg to about 175 mg, about 10 mg to about 175 mg, about 25 mg to about 175 mg, about 50 mg to about 175 mg, about 75 mg to about 175 mg, about 100 mg to about 175 mg, about 125 mg to about 175 mg, about 150 mg to about 175 mg, about 1 mg to about 150 mg, about 2 mg to about 150 mg, about 5 mg to about 150 mg, about 10 mg to about 150 mg, about 25 mg to about 150 mg, about 50 mg to about 150 mg, about 75 mg to about 150 mg, about 100 mg to about 150 mg, about 125 mg to about 150 mg, about 1 mg to about 125 mg, about 2 mg to about 125 mg, about 5 mg to about 125 mg, about 10 mg to about 125 mg, about 25 mg to about 125 mg, about 50 mg to about 125 mg, about 75 mg to about 125 mg, about 100 mg to about 125 mg, about 1 mg to about 100 mg, about 2 mg to about 100 mg, about 5 mg to about 100 mg, about 10 mg to about 100 mg, about 25 mg to about 100 mg, about 50 mg to about 100 mg, or about 75 mg to about 100 mg of a crystalline forms of Compound I or a crystalline forms of a salt or co-crystal of Compound I.

In some embodiments, for oral administration, each dosage unit contains about 1 mg, about 2 mg, about 5 mg, about 10 mg, about 15 mg, about 20 mg, about 25 mg, about 30 mg, about 35 mg, about 40 mg, about 45 mg, about 50 mg, about 75 mg, about 100 mg, about 125 mg, about 150 mg, about 175 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of a crystalline form of Compound I or a crystalline form of a salt or a co-crystal of Compound I.

The dosages for oral administration described above may be administered once daily (QD) or twice daily (BID). In some embodiments, the crystalline form of Compound I or the crystalline form of a salt or a co-crystal of Compound I, or a pharmaceutical composition thereof, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 75 mg QD, about 100 mg QD, about 125 mg QD, about 150 mg QD, about 175 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments, it is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

In some embodiments, for parenteral administration, each dosage unit contains from 0.1 mg to 1 g, 0.1 mg to 700 mg, or 0.1 mg to 100 mg of a crystalline form of Compound I or a crystalline form of a salt or a co-crystal of Compound I.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of the crystalline form of Compound I or the crystalline form of a salt or a co-crystal of Compound I. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions comprising the crystalline forms of Compound I or crystalline forms of salts of Compound I, may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner Dosing Regimen In the methods provided herein, the crystalline form of Compound I or the crystalline forms of a salt or a co-crystal of Compound I, or a pharmaceutical composition thereof, is administered in a therapeutically effective amount to achieve its intended purpose. Determination of a therapeutically effective amount is well within the capability of those skilled in the art, especially in light of the detailed disclosure provided herein. In some embodiments (methods of treating cancer), a therapeutically effective amount of the crystalline form, may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

The therapeutically effective amount may vary depending on the subject, and disease or condition being treated, the weight and age of the subject, the severity of the disease or condition, and the manner of administering, which can readily be determined by one or ordinary skill in the art.

The dosing regimen of the crystalline forms of Compound I or the crystalline forms of a salt or a co-crystal of Compound I, in the methods provided herein may vary depending upon the indication, route of administration, and severity of the condition, for example. Depending on the route of administration, a suitable dose can be calculated according to body weight, body surface area, or organ size. The final dosing regimen is determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the doses appropriate for treatment involving any of the formulations mentioned herein is done routinely by the skilled practitioner without undue experimentation, especially in light of the dosing information and assays disclosed, as well as the pharmacokinetic data observed in human clinical trials. Appropriate doses can be ascertained through use of established assays for determining concentration of the agent in a body fluid or other sample together with dose response data.

The formulation and route of administration chosen may be tailored to the individual subject, the nature of the condition to be treated in the subject, and generally, the judgment of the attending practitioner. For example, the compounds can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992).

The therapeutically effective amount of the crystalline forms of Compound I or the crystalline forms of a salt or a co-crystal of Compound I, may be provided in a single dose or multiple doses to achieve the desired treatment endpoint. As used herein, "dose" refers to the total amount of an active ingredient (e.g., the crystalline forms of Compound I or the crystalline forms of a salt or a co-crystal of Compound I) to be taken each time by a subject (e.g., a human). The dose administered, for example for oral administration described above, may be administered once daily (QD), twice daily (BID), three times daily, four times daily, or more than four times daily. In some embodiments, the dose is administered once daily. In some embodiments, the dose is administered twice daily.

In some embodiments, exemplary doses of the crystalline forms of Compound I or the crystalline forms of a salt or a co-crystal of Compound I, for a human subject may be from about 10 mg to about 1000 mg, about 20 mg to about 1000 mg, about 30 mg to about 1000 mg, about 40 mg to about 1000 mg, about 50 mg to about 1000 mg, about 60 mg to about 1000 mg, about 10 mg to about 750 mg, about 20 mg to about 750 mg, about 30 mg to about 750 mg, about 40 mg to about 750 mg, about 50 mg to about 750 mg, about 60 mg to about 500 mg, about 90 mg to about 500 mg, about 120 mg to about 500 mg, about 10 mg to about 400 mg, about 20 mg to about 400 mg, about 30 mg to about 400 mg, about 40 mg to about 400 mg, about 50 mg to about 400 mg, about 60 mg to about 400 mg, about 90 mg to about 400 mg, about 120 mg to about 400 mg, about 10 mg to about 120 mg, about 20 mg to about 120 mg, about 30 mg to about 120 mg, about 60 mg to about 120 mg or about 90 mg to about 120 mg.

In some embodiments, exemplary doses of the crystalline forms of Compound I or the crystalline forms of a salt or a co-crystal of Compound I, for a human subject may be about 5 mg, about 10 mg, about 15 mg, about 20 mg, about 25 mg, about 30 mg, about 35 mg, about 40 mg, about 45 mg, about 50 mg, about 55 mg, about 60 mg, about 75 mg, about 100 mg, about 120 mg, about 150 mg, about 175 mg, about 200 mg, about 225 mg, about 250 mg or about 300 mg.

In other embodiments, the methods provided comprise continuing to treat the subject (e.g., a human) by administering the doses herein, at which clinical efficacy is achieved or reducing the doses by increments to a level at which efficacy can be maintained. In some embodiments, the methods provided comprise administering to the subject (e.g., a human) an initial daily dose of 100 mg to 1000 mg of the crystalline compound and administering subsequent daily doses of the crystalline forms of Compound I or the crystalline forms of a salt or a co-crystal of Compound I, over at least 6 days, wherein each subsequent daily dose is increased by 50 mg to 400 mg. Thus, it should also be understood that the dose may be increased by increments until clinical efficacy is achieved. Increments of about 25 mg, about 50 mg, about 100 mg, or about 125 mg, or about 150 mg, or about 200 mg, or about 250 mg, or about 300 mg can be used to increase the dose. The dose can be increased daily, every other day, two, three, four, five or six times per week, or once per week.

The frequency of dosing will depend on the pharmacokinetic parameters of the compound administered, the route of administration, and the particular disease treated. The dose and frequency of dosing may also depend on pharmacokinetic and pharmacodynamic, as well as toxicity and therapeutic efficiency data.

The crystalline forms of Compound I or the crystalline forms of a salt or a co-crystal of Compound I, may be administered under fed conditions. The term fed conditions or variations thereof refers to the consumption or uptake of food, in either solid or liquid forms, or calories, in any suitable form, before or at the same time when the compounds or pharmaceutical compositions thereof are administered. For example, the crystalline form may be administered to the subject (e.g., a human) within minutes or hours of consuming calories (e.g., a meal). In some embodiments, it may be administered to the subject (e.g., a human) within 5-10 minutes, about 30 minutes, or about 60 minutes consuming calories.

In some embodiments a crystalline form of Compound I or a crystalline forms of a salt or a co-crystal of Compound I, may be administered as a 30 mg tablet orally once daily.

Articles of Manufacture and Kits

Compositions (including, for example, formulations and unit dosages) comprising the crystalline forms of Compound I or the crystalline forms of a salt or a co-crystal of Compound I, as described herein, can be prepared and placed in an appropriate container, and labeled for treatment of an indicated condition. Accordingly, provided is also an article of manufacture, such as a container comprising a unit dosage form of the crystalline forms of Compound I or the crystalline forms of a salt or a co-crystal of Compound I, and a label containing instructions for use of the compounds. In some embodiments, the article of manufacture is a container comprising a unit dosage form of the crystalline compound. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions. It should be understood that the active ingredient may be packaged in any material capable of improving chemical and physical stability, such as an aluminum foil bag. In some embodiments, diseases or conditions indicated on the label can include, for example, treatment of cancer.

Any pharmaceutical composition provided in the present disclosure may be used in the articles of manufacture, the same as if each and every composition were specifically and individually listed for use in an article of manufacture.

Kits comprising a pharmaceutical composition comprising a crystalline form of Compound I, or a crystalline form of a salt or a co-crystal of Compound I, are also provided. For example, a kit can comprise unit dosage forms of a crystalline form of Compound I or a crystalline form of a salt or a co-crystal of Compound I, as described herein, and a package insert containing instructions for use of the composition in treatment of a medical condition. In some embodiments, the kit comprises a crystalline form of Compound I or a crystalline form of a salt or a co-crystal of Compound I, and at least one pharmaceutically acceptable vehicle. The instructions for use in the kit may be for treating a cancer, including, for example, a hematologic malignancy. In some embodiments, the instructions are directed to use of the pharmaceutical composition for the treatment of cancer, such as leukemia or lymphoma, including relapsed and refractory leukemia or lymphoma. In some embodiments, the instructions for use in the kit may be for treating a hematologic cancer selected from the group consisting of small lymphocytic lymphoma, non-Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/− villous lymphocytes), Nodal marginal zone lymphoma (+/− monocytoid B-cells), extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, mediastinal large B-cell lymphoma, intravascular large B-cell lymphoma, primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldenstrom's macroglobulinemia. In one embodiment, the instructions for use in the kit may be for treating chronic lymphocytic leukemia or non-Hodgkin's lymphoma. In one embodiment, the NHL is diffuse large B-cell lymphoma, mantle cell lymphoma, follicular lymphoma, small lymphocytic lymphoma, lymphoplasmacytic lymphoma, and marginal zone lymphoma. In one embodiment, the hematologic malignancy is indolent non-Hodgkin's lymphoma. In some embodiments, diseases or conditions indicated on the label can include, for example, treatment of cancer.

In some instances, the instructions are directed to use of the pharmaceutical composition for the treatment of a solid tumor, wherein the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, ACTH-producing tumors.

In some instances, the instructions are directed to use of the pharmaceutical composition for the treatment of an allergic disorder and/or an autoimmune and/or inflammatory disease, and/or an acute inflammatory reaction. In some embodiments, the instructions are directed to use of the pharmaceutical composition for the treatment of an autoimmune disease, in some embodiments, the instructions are directed to use of the pharmaceutical composition for the treatment of an autoimmune disease selected from the group consisting of cutaneous lupus erythematosus, myasthenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease. In some embodiments, the autoimmune disease is selected from the group consisting of asthma, rheumatoid arthritis, multiple sclerosis, chronic obstructive pulmonary disease and systemic lupus erythematosus.

Any pharmaceutical composition provided in the present disclosure may be used in the kits, the same as if each and every composition were specifically and individually listed for use a kit.

The methods and crystalline forms described herein will typically be used in therapy for human subjects. However, they may also be used to treat similar or identical indications in other animal subjects. One or more crystalline forms of Compound I and/or one or more crystalline forms of salts or co-crystals of Compound I as described herein can be administered by different routes, including injection (i.e. parenteral, including intravenous, intraperitoneal, subcutaneous, and intramuscular), oral, transdermal, transmucosal, rectal, or inhalant.

Methods

In some embodiments, the disclosure provides a method for treating a disease or condition mediated by a Syk kinase in a subject in need thereof, by administering to the subject a therapeutically effective amount one or more crystalline forms of Compound I and/or one or more crystalline forms of salts or co-crystals of Compound I as described herein.

In some embodiments, the disclosure provides a method for treating a disease or condition selected from the group consisting of an inflammatory disorder, an allergic disorder, an autoimmune disease, and a cancer in a subject in need thereof, comprising administering to the subject a therapeutic effective amount of one or more crystalline forms of Compound I and/or one or more crystalline forms of salts or co-crystals of Compound I as described herein.

In some embodiments, the disease or condition is a cancer selected from the group consisting of a hematologic malignancy and a solid tumor. In some embodiments, the disease or condition is a hematologic malignancy selected from the group consisting of lymphoma, multiple myeloma, or leukemia.

In some embodiments, the disease or condition is selected from the group consisting of small lymphocytic lymphoma, non-Hodgkin's lymphoma, indolent non-Hodgkin's lymphoma, refractory iNHL, mantle cell lymphoma, follicular lymphoma, lymphoplasmacytic lymphoma, marginal zone lymphoma, immunoblastic large cell lymphoma, lymphoblastic lymphoma, Splenic marginal zone B-cell lymphoma (+/− villous lymphocytes), Nodal marginal zone lymphoma (+/− monocytoid B-cells), Extranodal marginal zone B-cell lymphoma of mucosa-associated lymphoid tissue type, cutaneous T-cell lymphoma, extranodal T-cell lymphoma, anaplastic large cell lymphoma, angioimmunoblastic T-cell lymphoma, mycosis fungoides, B-cell lymphoma, diffuse large B-cell lymphoma, Mediastinal large B-cell lymphoma, Intravascular large B-cell lymphoma, Primary effusion lymphoma, small non-cleaved cell lymphoma, Burkitt's lymphoma, multiple myeloma, plasmacytoma, acute lymphocytic leukemia, T-cell acute lymphoblastic leukemia, B-cell acute lymphoblastic leukemia, B-cell prolymphocytic leukemia, acute myeloid leukemia, chronic lymphocytic leukemia, juvenile myelomonocytic leukemia, minimal residual disease, hairy cell leukemia, primary myelofibrosis, secondary myelofibrosis, chronic myeloid leukemia, myelodysplastic syndrome, myeloproliferative disease, and Waldenstrom's macroglobulinemia.

In some embodiments, the disease or condition is a solid tumor, wherein the solid tumor is from a cancer selected from the group consisting of pancreatic cancer, urological cancer, bladder cancer, colorectal cancer, colon cancer, breast cancer, prostate cancer, renal cancer, hepatocellular cancer, thyroid cancer, gall bladder cancer, lung cancer (e.g. non-small cell lung cancer, small-cell lung cancer), ovarian cancer, cervical cancer, gastric cancer, endometrial cancer, esophageal cancer, head and neck cancer, melanoma, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, cancers of the adrenal cortex, and ACTH-producing tumors.

In some embodiments, the disease or condition is selected from the group consisting of lupus, such as systemic lupus erythematosus and cutaneous lupus erythematosus, myasthenia gravis, Goodpasture's syndrome, glomerulonephritis, hemorrhage, pulmonary hemorrhage, atherosclerosis, rheumatoid arthritis, psoriatic arthritis, monoarticular arthritis, osteoarthritis, gouty arthritis, spondylitis, Behçet disease, autoimmune thyroiditis, Reynaud's syndrome, acute disseminated encephalomyelitis, chronic idiopathic thrombocytopenic purpura, multiple sclerosis, Sjögren's syndrome, autoimmune hemolytic anemia, tissue graft rejection, hyperacute rejection of transplanted organs, allograft rejection, graft-versus-host disease, diseases involving leukocyte diapedesis, disease states due to leukocyte dyscrasia and metastasis, granulocyte transfusion-associated syndromes, cytokine-induced toxicity, scleroderma, vasculitis, asthma, psoriasis, chronic inflammatory bowel disease, ulcerative colitis, Crohn's disease, necrotizing enterocolitis, irritable bowel syndrome, dermatomyositis, Addison's disease, Parkinson's disease, Alzheimer's disease, diabetes, type I diabetes mellitus, sepsis, septic shock, endotoxic shock, gram negative sepsis, gram positive sepsis, and toxic shock syndrome, multiple organ injury syndrome secondary to septicemia, trauma, hypovolemic shock, allergic conjunctivitis, vernal conjunctivitis, and thyroid-associated ophthalmopathy, eosinophilic granuloma, eczema, chronic bronchitis, acute respiratory distress syndrome, allergic rhinitis, coryza, hay fever, bronchial asthma, silicosis, pulmonary sarcoidosis, pleurisy, alveolitis, emphysema, pneumonia, bacterial pneumonia, bronchiectasis, and pulmonary oxygen toxicity, reperfusion injury of the myocardium, brain, or extremities, thermal injury, cystic fibrosis, keloid formation or scar tissue formation, fever and myalgias due to infection, and brain or spinal cord injury due to minor trauma, diseases involving leukocyte diapedesis, acute hypersensitivity, delayed hypersensitivity, urticaria, food allergies, skin sunburn, inflammatory pelvic disease, urethritis, uveitis, sinusitis, pneumonitis, encephalitis, meningitis, myocarditis, nephritis, osteomyelitis, myositis, hepatitis, alcoholic hepatitis, gastritis, enteritis, contact dermatitis, atopic dermatitis, gingivitis, appendicitis, pancreatitis, cholecystitis, polycythemia vera, essential thrombocythemia, and polycystic kidney disease.

In some embodiments, the disease or condition is selected from the group consisting of systemic lupus erythematosus, myasthenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease, cutaneous lupus erythematosus, systemic lupus erythematosus, myasthenia gravis, rheumatoid arthritis, acute disseminated encephalomyelitis, idiopathic thrombocytopenic purpura, multiple sclerosis, Sjoegren's syndrome, psoriasis, autoimmune hemolytic anemia, asthma, ulcerative colitis, Crohn's disease, irritable bowel disease, and chronic obstructive pulmonary disease.

In some embodiments, the disease or condition is selected from the group consisting of asthma, rheumatoid arthritis, multiple sclerosis, chronic obstructive pulmonary disease, and systemic lupus erythematosus. In some embodiments, wherein the disease or condition is rheumatoid arthritis. In some embodiments, the subject is human.

In some embodiments, this disclosure provides the methods as described herein, wherein the crystalline form is administered intravenously, intramuscularly, parenterally, nasally or orally. In some embodiments, the crystalline form is administered QD orally. In some embodiments, the crystalline form is administered BID orally.

In some embodiments, this disclosure provides crystalline forms of Compound I or crystalline forms of salts of Compound I, as described herein, for use in therapy. In some embodiments, this disclosure provides a use of a crystalline form of Compound I or a crystalline form of a salt or a co-crystal of Compound I, as described herein, in the manufacture of a medicament for the treatment of a disease or condition selected from the group consisting of an inflammatory disorder, an allergic disorder, an autoimmune disease, and a cancer.

In some embodiments, this disclosure provides a use of a crystalline form of Compound I or a crystalline form of a salt or a co-crystal of Compound I, as described herein, in the manufacture of a medicament for the treatment of rheumatoid arthritis.

In some embodiments, this disclosure provides a use of a crystalline form of Compound I or a crystalline form of a salt or a co-crystal of Compound I, as described herein, in the manufacture of a medicament for the treatment of a hematologic malignancy. In some embodiments, the hematologic malignancy is lymphoma, multiple myeloma or leukemia.

Monotherapy and Combination Therapies

Also provided are methods of treatment in which a crystalline form of Compound I or a crystalline form of a salt or a co-crystal of Compound I is the only active agent given to a subject and also includes methods of treatment in which a crystalline form of Compound I or a crystalline form of a salt or a co-crystal of Compound I, is given to a subject in combination with one or more additional active agents. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof an effective amount of a crystalline form of Compound I or a crystalline form of a salt or a co-crystal of Compound I, wherein the subject is not undergoing therapy for the same disease or condition with another agent or procedure.

In some embodiments where the crystalline form is administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapies (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof; (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of a crystalline form of Compound I or a crystalline form of a salt or a co-crystal of Compound I, as a monotherapy).

It should be understood that when a subject (e.g. a human) is treated with of a crystalline form of Compound I or a crystalline form of a salt or a co-crystal of Compound I, as a monotherapy, the subject may also undergo one or more other therapies that are not anti-cancer therapies.

In some embodiments, a method of treating a comorbidity of a cancer, including but not limited to CLL, in a subject (e.g., a human) who has been diagnosed with cancer, e.g. CLL, wherein the method comprises administering a therapy to treat the comorbidity in combination with a crystalline form of Compound I or a crystalline form of a salt or a co-crystal of Compound I, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, valvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Combination Therapies

In some embodiments, a method of treating cancer, an allergic disorder and/or an autoimmune and/or inflammatory disease, and/or an acute inflammatory reaction comprises administering to a subject in need thereof an effective amount of a crystalline form of Compound I or a crystalline form of a salt or a co-crystal of Compound I, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a crystalline form of Compound I or a crystalline form of a salt or a co-crystal of Compound I. In some embodiments, a crystalline form of Compound I or a crystalline form of a salt or a co-crystal of Compound I, is combined with another active agent in a single dosage form. In one embodiment, the invention provides a product comprising a crystalline form of Compound I or a crystalline form of a salt or a co-crystal of Compound I, and an additional therapeutic agent as a combined preparation for simultaneous, separate or sequential use in therapy, e.g. a method of treating a cancer, an allergic disorder and/or an autoimmune and/or inflammatory disease, and/or an acute inflammatory reaction.

Provided herein are also methods of treatment in which the a crystalline form of Compound I or a crystalline form of a salt or a co-crystal of Compound I, administered to a subject (e.g., a human) who has been diagnosed with or is suspected of having a cancer is given to the subject in combination with one or more additional therapies, including one or more of the anti-cancer therapies described above. Thus, in some embodiments, the method for treating cancer in a subject (e.g., a human) in need thereof, comprises administering to the subject a therapeutically effective amount of a crystalline form of Compound I or a crystalline form of a salt or a co-crystal of Compound I, together with one or more additional therapies, which can be useful for treating the cancer. The one or more additional therapies may involve the administration of one or more therapeutic agents. Suitable anti-cancer therapeutics that may be used in combination with a crystalline form of Compound I or a crystalline form of a salt or a co-crystal of Compound I include, but are not limited to, one or more agents selected from the group consisting of chemotherapeutic agents (e.g. mitomycin C, carboplatin, taxol, cisplatin, paclitaxel, etoposide, doxorubicin), radiotherapeutic antitumor agents, topoisomerase I inhibitors (e.g. camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), PI3K inhibitors (e.g. compounds A, B, and C below), inhibitors of lysyl oxidase-like 2, and biological agents (e.g. antibodies such as anti CD20 antibody, IDEC 8, immunotoxins, and cytokines).

In some embodiments, the method for treating cancer in a subject (e.g., a human) in need thereof, comprises administering to the subject a therapeutically effective amount of a compound of a crystalline form of Compound I or a crystalline form of a salt or a co-crystal of Compound I, or a pharmaceutical composition thereof with one or more additional therapies selected from the group consisting of fludarabine, rituximab, obinutuzumab, alemtuzumab, cyclophosphamide, chlorambucil, doxorubicin, doxorubicin hydrochloride, vincristine, vincristine sulfate, melphalan, busulfan, carmustine, prednisone, prednisolone, dexamethasone, methotrexate, cytarabine, mitoxantrone, mitoxantrone hydrochloride, bortezomib, temsirolimus, carboplatin, etoposide, thalidomide, cisplatin, lumiliximab, anti-TRAIL, bevacizumab, galiximab, epratuzumab, SGN-40, anti-CD74, ofatumumab, ha20, PRO131921, CHIR-12.12, apolizumab, milatuzumab, bevacizumab, yttrium-90-labeled ibritumomab tiuxetan, tositumomab, iodine-131 tositumomab, ifosfamide, GTOP-99 vaccine, oblimersen, flavopiridol, PD0332991, R-roscovitine, styryl sulfones, Obatoclax, TRAIL, Anti-TRAIL DR4 and DR5 antibodies, Everolimus, BMS-345541, Curcumin, Vorinostat, lenalidomide, Geldanamycin, perifosine, sildenafil citrate, CC-5103, simvastatin, enzastaurin, campath-1H, DT PACE, antineoplaston A10, antineoplaston AS2-1, beta alethine, filgrastim, recombinant interferon alfa, dolastatin 10, indium In 111 monoclonal antibody MN-14, anti-thymocyte globulin, cyclosporine, mycophenolate mofetil, therapeutic allogeneic lymphocytes, tacrolimus, thiotepa, paclitaxel, aldesleukin, docetaxel, ifosfamide, mesna, recombinant interleukin-12, recombinant interleukin-11, ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, octreotide acetate, motexafin gadolinium, arsenic trioxide, tipifarnib, autologous human tumor-derived HSPPC-96, veltuzumab, bryostatin 1, PEGylated liposomal hydrochloride, peripheral blood stem cell transplantation, autologous hematopoietic stem cell transplantation, autologous bone marrow transplantation, infusion of stem cells, bone marrow ablation with stem cell support, in vitro-treated peripheral blood stem cell transplantation, umbilical cord blood transplantation, low-LET cobalt-60 gamma ray therapy, bleomycin, conventional surgery, radiation therapy, and nonmyeloablative allogeneic hematopoietic stem cell transplantation.

In some embodiments, the one or more additional therapies involve the use of a phosphatidylinositol 3-kinase (PI3K) inhibitor, including for example, Compounds A, B or C, or a pharmaceutically acceptable salt of such compounds. The structures of Compounds A, B and C are provided below.

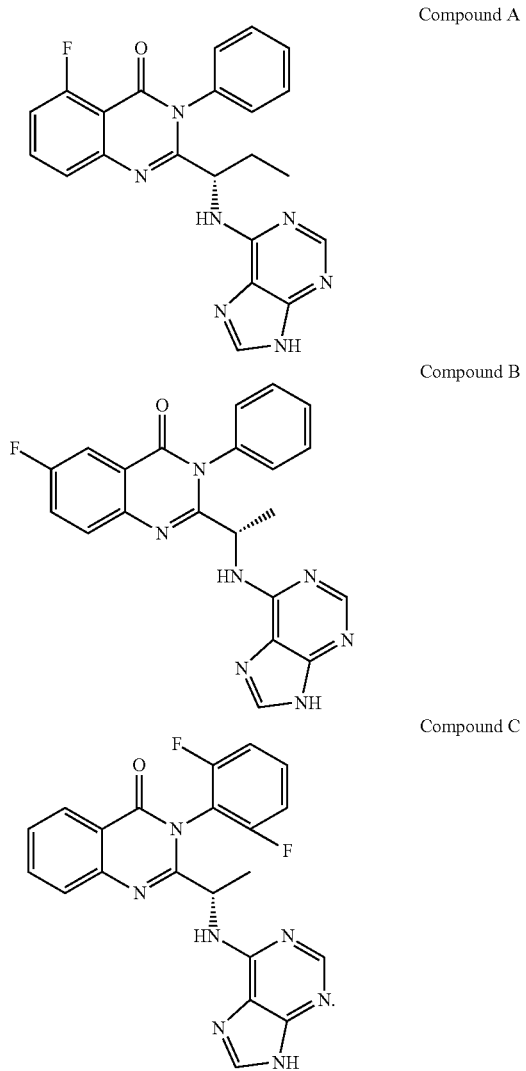

Compound A

Compound B

Compound C

In other embodiments of the methods described above involving the use of a crystalline form of Compound I or a crystalline form of a salt or a co-crystal of Compound I, in combination with one or more additional therapies, the one or more additional therapies is other than a therapy using Compound A, Compound B, or Compound C, or a pharmaceutically acceptable salt or a co-crystal of such compounds. In one embodiment of the methods described above involving the use of a crystalline form of Compound I or a crystalline form of a salt or a co-crystal of Compound I, in combination with one or more additional therapies, the one or more additional therapies is other than a therapy using Compound A, or a pharmaceutically acceptable salt. In another embodiment of the methods described above involving the use of a crystalline form of Compound I or a crystalline form of a salt or a co-crystal of Compound I, in combination with one or more additional therapies, the one or more additional therapies is other than a therapy using Compound B, or a pharmaceutically acceptable salt or co-crystal thereof. In yet another embodiment of the methods described above involving the use of a crystalline form of Compound I or a crystalline form of a salt or a co-crystal of Compound I, in combination with one or more additional therapies, the one or more additional therapies is other than a therapy using Compound C, or a pharmaceutically acceptable salt or co-crystal thereof.

In other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

The crystalline forms of Compound I or the crystalline forms of a salt or a co-crystal of Compound I, as described herein, can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with a crystalline form of Compound I or a crystalline form of a salt or a co-crystal of Compound I, or a pharmaceutical composition thereof, in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines). In one embodiment of the method for increasing sensitivity of cancer cells to chemotherapy, the chemotherapeutic agent is other than Compound A, or a pharmaceutically acceptable salt or co-crystal thereof. In another embodiment of the method for increasing sensitivity of cancer cells to chemotherapy, the chemotherapeutic agent is other than Compound B, or a pharmaceutically acceptable salt or co-crystal thereof. In yet another embodiment of the method for increasing sensitivity of cancer cells to chemotherapy, the chemotherapeutic agent is other than Compound C, or a pharmaceutically acceptable salt or co-crystal thereof.

In some embodiments, a crystalline form of Compound I or a crystalline form of a salt or a co-crystal of Compound I, is used in combination with Rituxan® (Rituximab) or other agents that work by selectively depleting CD20+B-cells.

Included herein are methods of treating cancer, an allergic disorder and/or an autoimmune and/or inflammatory disease, and/or an acute inflammatory reaction comprising administering to a subject in need thereof an effective amount of a crystalline form of Compound I or a crystalline form of a salt or a co-crystal of Compound I, or a pharmaceutical composition thereof, in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

In some embodiments, combinations with filgotinib are used. In some embodiments, combinations with methotrexate are used.

Provided herein are also methods of treatment in which a crystalline form of Compound I or a crystalline form of a salt or a co-crystal of Compound I, administered to a subject (e.g., a human) who has been diagnosed with or is suspected of having an autoimmune disease is given to the subject in combination with one or more anti-inflammatory or immunosuppressant agents selected from the group consisting of ibuprofen, flurbiprofen, naproxen, naproxen sodium, diclofenac, diclofenac sodium, misoprostol, sulindac, oxaprozin, diflunisal, piroxicam, indomethacin, etodolac, fenoprofen calcium, ketoprofen, sodium nabumetone, sulfasalazine, tolmetin sodium, hydroxychloroquine, celecoxib, valdecoxib, lumiracoxib, etoricoxib, rofecoxib, acetylsalicylic acid, sodium salicylate, choline salicylate, magnesium salicylate, cortisone, dexamethasone, methylprednisolone, prednisolone, prednisolone sodium phosphate, prednisone, gold sodium thiomalate, auranofin, methotrexate, dihydroorotate leflunomide, leflunomide, cyclosporine, tacrolimus, azathioprine, mycophenolate mofetil, eculizumab, pexelizumab, entanercept, and infliximab.

Provided herein are methods of treatment in which a crystalline form of Compound I or a crystalline form of a salt or a co-crystal of Compound I, in combination with a vinca-alkaloid, or a pharmaceutically acceptable salt thereof, administered to a subject (e.g., a human) is the only anti-cancer therapy regimen administered to the subject. Provided herein are methods of treatment in which a crystalline form of Compound I or a crystalline form of a salt or a co-crystal of Compound I, in combination with a vinca-alkaloid, or a pharmaceutically acceptable salt thereof, administered to a subject (e.g., a human), wherein the subject is not undergoing any other anti-cancer treatments. In one variation, the subject is not undergoing any other anti-cancer treatments using one or more PI3K inhibitors. Such PI3K inhibitors may include, in certain embodiments, Compounds A, B and C, whose structures are provided below.

Compound A

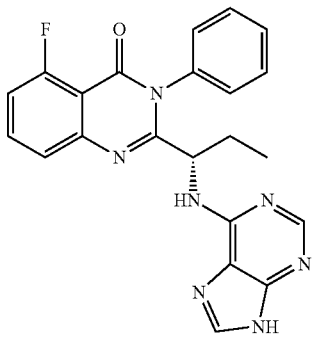

Compound B

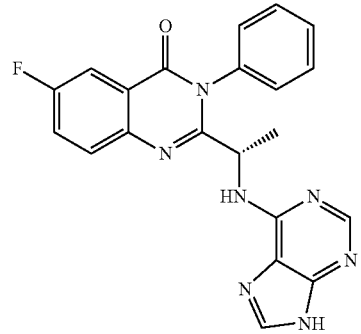

Compound C

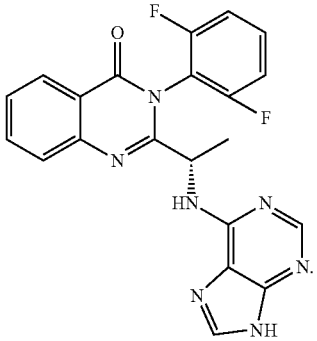

In one variation, the subject is not undergoing any other anti-cancer treatments using Compound A, or a pharmaceutically acceptable salt thereof. In another variation, the subject is not undergoing any other anti-cancer treatments using Compound B, or a pharmaceutically acceptable salt thereof. In yet another variation, the subject is not undergoing any other anti-cancer treatments using Compound C, or a pharmaceutically acceptable salt thereof.

In some embodiments where a crystalline form of Compound I or a crystalline form of a salt or a co-crystal of Compound I, in combination with a vinca-alkaloid, or a pharmaceutically acceptable salt thereof, is administered as a monotherapy treatment regimen to the subject, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

It should be understood that when a subject (e.g. a human) is treated with a crystalline form of Compound I or a crystalline form of a salt or a co-crystal of Compound I, in combination with a *vinca*-alkaloid, or a pharmaceutically acceptable salt thereof, as a monotherapy treatment regimen as described by this disclosure, the subject may also undergo one or more other therapies that are not anti-cancer therapies.

In some embodiments, there is provided a method for treating cancer in a subject in need thereof, comprising administering to the subject a therapeutically effective amount of a crystalline form of Compound I or a crystalline form of a salt or a co-crystal of Compound I, and a therapeutically effective amount of a *vinca*-alkaloid, or a pharmaceutically acceptable salt, wherein: the *vinca*-alkaloid is selected from the group consisting of vincristine, vindesine, vinorelbine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a *vinca*-alkaloid, or a pharmaceutically acceptable salt, wherein the *vinca*-alkaloid is selected from the group consisting of vincristine, vindesine, vinorelbine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In some embodiments, there is provided a method for treating cancer in a subject in need thereof, comprising administering to the subject a therapeutically effective amount of a crystalline form of Compound I or a crystalline form of a salt or a co-crystal of Compound I, and a therapeutically effective amount of a *vinca*-alkaloid, or a pharmaceutically acceptable salt, wherein: the *vinca*-alkaloid is selected from the group consisting of vincristine and vinblastine, and the subject is a human who is (i) refractory to at least one anti-cancer treatment, or (ii) in relapse after treatment with at least one anti-cancer therapy, or a combination thereof. In certain other embodiments, there is provided a method for treating cancer in a subject in need thereof, comprising administering to the subject a therapeutically effective amount of a compound of formula I, or a pharmaceutically acceptable salt, and a therapeutically effective amount of a *vinca*-alkaloid, or a pharmaceutically acceptable salt, wherein the *vinca*-alkaloid is selected from the group consisting of vincristine and vinblastine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a crystalline form of Compound I or a crystalline form of a salt or a co-crystal of Compound I, and a therapeutically effective amount of a *vinca*-alkaloid, or a pharmaceutically acceptable salt, wherein the *vinca*-alkaloid is vincristine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a *vinca*-alkaloid, or a pharmaceutically acceptable salt, wherein the *vinca*-alkaloid is vincristine, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In one embodiment, there is provided a method for treating cancer in a subject in need thereof, comprising administering to the subject a therapeutically effective amount of a crystalline form of Compound I or a crystalline form of a salt or a co-crystal of Compound I, and a therapeutically effective amount of a *vinca*-alkaloid, or a pharmaceutically acceptable salt, wherein: wherein the *vinca*-alkaloid is vinblastine, and the subject is a human who is (i) refractory to at least one anti-cancer treatment, or (ii) in relapse after treatment with at least one anti-cancer therapy, or a combination thereof. In one other embodiment, there is provided a method for treating cancer in a subject in need thereof, comprising administering to the subject a therapeutically effective amount of a compound of formula I, or a pharmaceutically acceptable salt, and a therapeutically effective amount of a *vinca*-alkaloid, or a pharmaceutically acceptable salt, and wherein further the subject is a human who is not undergoing any other anti-cancer treatments; and the subject is (i) refractory to at least one anti-cancer treatment, or (ii) in relapse after treatment with at least one anti-cancer therapy, or a combination thereof.

In yet other embodiments where a crystalline form of Compound I or a crystalline form of a salt or a co-crystal of Compound I, in combination with a *vinca*-alkaloid, or a pharmaceutically acceptable salt thereof, is administered as a monotherapy treatment regimen to the subject, the subject may have a 17p deletion, a TP53 mutation, NOTCH1, a SF3B1 mutation, a 1 lq deletion, or any combination thereof. In some embodiments where a crystalline form of Compound I or a crystalline form of a salt or a co-crystal of Compound I, in combination with a *vinca*-alkaloid, or a pharmaceutically acceptable salt thereof, is administered as a monotherapy treatment regimen to the subject, the subject has a 17p deletion, a TP53 mutation, or a combination thereof. In another embodiments a crystalline form of Compound I or a crystalline form of a salt or a co-crystal of Compound I, in combination with a *vinca*-alkaloid, or a pharmaceutically acceptable salt thereof, is administered as a monotherapy treatment regimen to the subject, the subject has NOTCH1, a SF3B1 mutation, a 11$q$ deletion, or any combination thereof.

Provided herein are also methods of treatment in which a crystalline form of Compound I or a crystalline form of a salt or a co-crystal of Compound I, in combination with a *vinca*-alkaloid, or a pharmaceutically acceptable salt thereof, administered to a subject (e.g., a human) is given to a subject (e.g., a human) in additional combination with one or more additional therapies, including one or more of the anti-cancer therapies described above. Thus, in some embodiments, the method for treating cancer in a subject (e.g., a human) in need thereof, comprises administering to the subject a therapeutically effective amount of a crystalline form of Compound I or a crystalline form of a salt or a co-crystal of Compound I, or a pharmaceutical composition thereof, in combination with a *vinca*-alkaloid, or a pharmaceutically acceptable salt thereof, together with one or more additional therapies, which can be useful for treating the cancer. The one or more additional therapies may involve the administration of one or more therapeutic agents as described herein.

For example, in other embodiments, the one or more additional therapeutic agent may be an inhibitors of lysyl oxidase-like 2 (LOXL2) and a substance that bind to LOXL2, including for example, a humanized monoclonal antibody (mAb) with an immunoglobulin IgG4 isotype directed against human LOXL2.

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein, is combined with another therapeutic agent in a single dosage form, which is then administered prior to, concomitant with or subsequent to administration with a *vinca*-alkaloid, or a pharmaceutically acceptable salt thereof, of this disclosure. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

It should be understood that any combinations of the additional therapeutic agents described above may be used, as if each and every combination was individually listed. For example, in some embodiments, the additional therapeutic agents include a PI3K inhibitor and a LOXL2 inhibitor.

It should be understood that any combinations of the additional therapeutic agents described above may be used, as if each and every combination was individually listed. For example, in some embodiments, the additional therapeutic agents include a PI3K inhibitor and a LOXL2 inhibitor.

EXAMPLES

Instrumental Techniques
X-Ray Powder Diffraction (XRPD)
X-ray powder diffraction (XRPD) analysis was conducted on a diffractometer (PANalytical XPERT-PRO, PANalytical B. V., Almelo, Netherlands) using copper radiation (Cu Kα, λ=1.541874 Å). Samples were spread evenly on a zero background sample plate. The generator was operated at a voltage of 45 kV and amperage of 40 mA. Slits were Soller 0.02 rad, antiscatter 1.0°, and divergence. Scans were performed from 2 to 40° 2θ with a 0.0167 step size. Data analysis was performed using X'Pert Data Viewer V1.2d (PANalytical B.V., Almelo, Netherlands). X-ray powder diffraction analysis was also conducted on a diffractometer (Rigaku MiniFlex, Rigaku Corporation, Beijing, China) using copper radiation (Cu Kα, λ=1.541874 Å). Samples were spread evenly on a zero background sample plate. The generator was operated at a voltage of 40 kV and amperage of 15 mA. Scans were performed from 2 to 40° 2θ with a 0.050 degree step size and a speed of 2 degrees/minute. Data analysis was also performed using X'Pert Data Viewer V1.2d (PANalytical B.V., Almelo, Netherlands). The XRPD peaks are in the range of ±0.2° 2θ.

Differential Scanning Calorimetry (DSC)

Differential Scanning calorimetry (DSC) was run by loading 1-5 mg of material into a crimped Tzero standard aluminum pan and heating the sample at 10° C./min from 20 to 300° C. or above. The sample and reference pans were under a 50 mL/min nitrogen purge. Data analysis was completed using Universal Analysis 2000 Version 4.7A (TA Instruments, New Castle, Del.). The DSC endotherm peaks and onset temperatures are in the range of ±3° C.

Thermogravimetric Analysis (TGA)

Thermogravimetric analysis (TGA) was used to evaluate sample weight loss as a function of temperature by loading 1-10 mg of material onto a an aluminum weigh pan (TA Instruments, New Castle, Del.) and heated the sample to 350° C. or above at a rate of 10° C./min. The sample and reference pans were under a 60 mL/min and 40 mL/min nitrogen purge, respectively. Data analysis was completed using Universal Analysis 2000 Version 4.7A (TA Instruments, New Castle, Del.).

Thermogravimetric analysis with Mass Spectrometry (TA Discovery Series TGA and MS) was used to determine what was associated with the sample weight loss as a function of temperature (TA Instruments, New Castle). A sample (~2-5 mg) was placed in a platinum pan and heated up to 300° C. or above at a heating rate of 10-20° C./min. The sample and reference pans were under a 25 mL/min and 10 mL/min nitrogen purge, respectively. Data analysis was completed using TA Instruments Trios Software v. 4.0 (TA Instruments, New Castle, Del.).

Dynamic Vapor Sorption/Desorption (DVS)

Hygroscopicity was studied using dynamic vapor sorption (DVS, TA Q5000 SA, TA Instruments, New Castle, Del. or DVS, DVS Intrinsic, Surface Measurement Systems, London, UK). A sample (2-20 mg) was placed in an aluminum DVS pan and loaded on the sample side of the twin pan balance. The water sorption and desorption were studied as a function of relative humidity (RH) at 25° C. In 10% RH increments, the relative humidity was increased from 5% RH to 95% RH and then decreased back to 5%. Each relative humidity increment had an equilibration time of 180 minutes, unless weight change % was less than 0.002% in 30 minutes. Data analysis was performed using Universal Analysis 2000 Version 4.7A (TA Instruments, New Castle, Del.) for TA DVS runs and Microsoft Excel for SMS DVS runs.

Example 1: Preparation of Compound I
Compound I was synthesized as shown in Scheme I below:
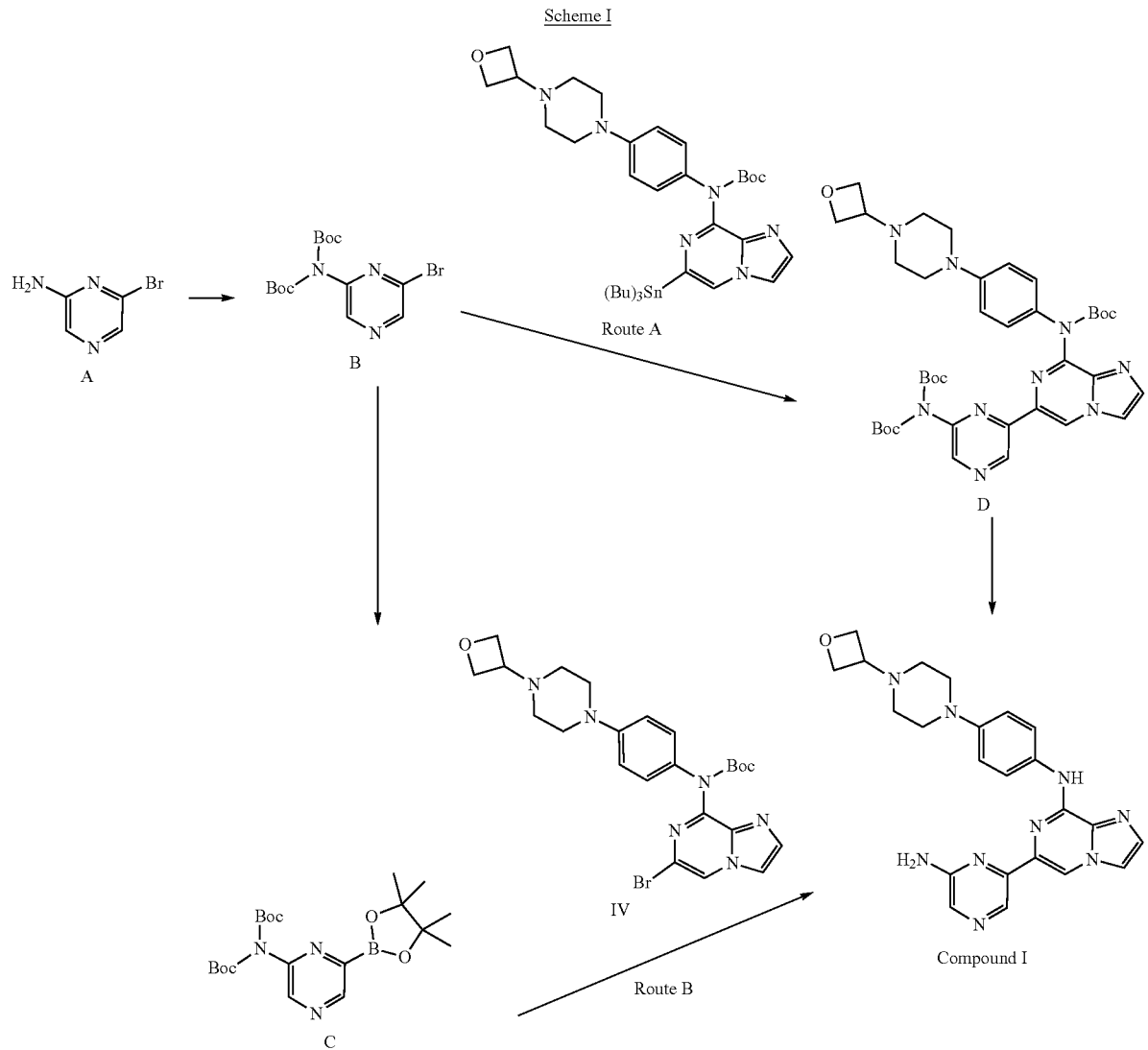
The compounds IV and V in Scheme I were prepared as shown in scheme II below.
Preparation of tert-Butyl (6-bromoimidazo[1,2-a]pyrazin-8-yl)(4-(4-(oxetan-3-yl)piperazin-1-yl)phenyl)carbamate IV and tert-butyl 4-(4-(oxetan-3-yl)piperazin-1-yl)phenyl(6-(tributylstannyl)imidazo[1,2-a]pyrazin-8-yl)carbamate V

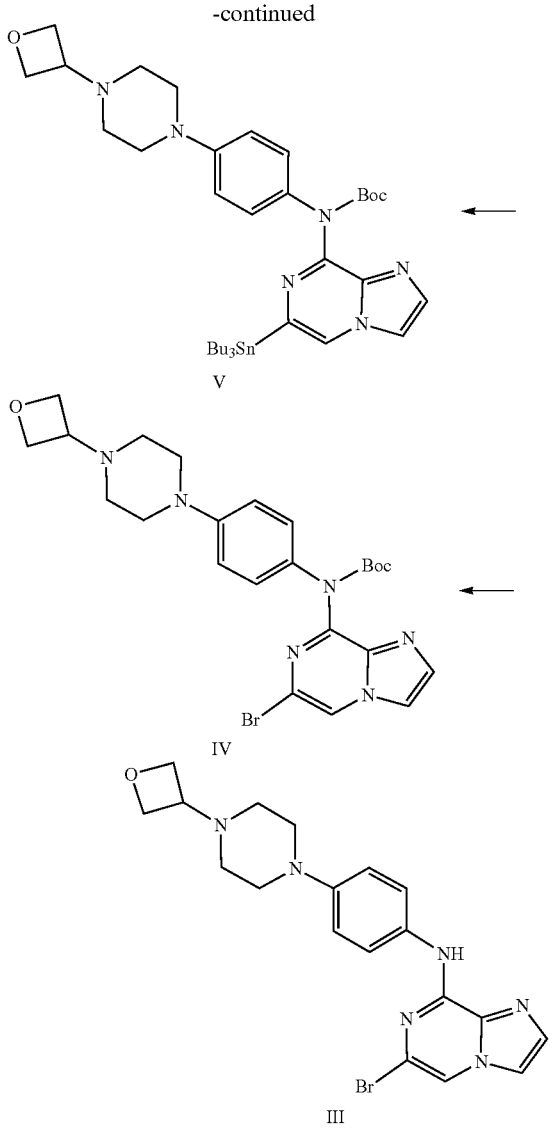

1-(4-Nitrophenyl)-4-(oxetan-3-yl)piperazine I: In a 500 mL round bottom flask, 1-(oxetan-3-yl)piperazine (3.02 g, 21.26 mmoles), potassium carbonate (5.87 g, 42.52 mmoles), 1-fluoro-4-nitrobenzene (3.00 g, 21.26 mmoles) was combined in acetonitrile (33 mL) and stirred under nitrogen overnight at 100° C. The mixture was diluted with water (100 mL) and extracted with DCM (100 mL×3), dried over anhydrous sodium carbonate, filtered and the filtrate was concentrated. The residue was dissolved in minimal DCM using a sonicator and crashed out with hexane. The precipitate was filtered, washed with hexane and dried to provide the title Compound I.

4-(4-(Oxetan-3-yl)piperazin-1-yl)aniline II: In a hydrogenation vessel, 1-(4-nitrophenyl)-4-(oxetan-3-yl)piperazine I (4.70 g, 17.85 mmoles) was dissolved as much as possible in MeOH (26 mL) and DCM (5 mL). Pd/C (10%) (2.85 g, 2.68 mmoles) was added and the reaction was stored under nitrogen. The reaction was shaken on the Parr hydrogenator at 45 PSI. After 15 minutes, the reaction was fully recharged to 45 PSI and shaken for an additional hour. The material was filtered over celite, washed with 25% MeOH/DCM and concentrated to provide the title Compound II.

6-Bromo-N-(4-(4-(oxetan-3-yl)piperazin-1-yl)phenyl) imidazo[1,2-a]pyrazin-8-amine III: To 4-(4-(oxetan-3-yl) piperazin-1-yl)aniline II (2.00 g, 8.57 mmoles), Hunig's base (3.29 mL) and 6,8-dibromoimidazo[1,2-a]pyrazine (2.37 g, 8.57 mmoles) was added in DMF (43 mL). The reaction was stirred at 85° C. in a pressure tube for overnight. The material was quenched with saturated sodium bicarbonate, extracted with DCM (120 mL×3) and the organic layers were combined and washed with water (120 mL×3), dried over anhydrous sodium carbonate and concentrated. The crude material was purified using a 120 g Isco column and eluted off using a stepwise gradient of 0-60% (10% MeOH/DCM). The desired fractions were combined and concentrated to provide the title Compound III.

tert-Butyl (6-bromoimidazo[1,2-a]pyrazin-8-yl)(4-(4-(oxetan-3-yl)piperazin-1-yl)phenyl)carbamate IV: 6-bromo-N-(4-(4-(oxetan-3-yl)piperazin-1-yl)phenyl)imidazo[1,2-a] pyrazin-8-amine III (1000 mg, 2.33 mmol), di-tert-butyl dicarbonate (1016.72 mg, 4.66 mmol) and N,N-dimethylpyridin-4-amine (21.34 mg, 0.17 mmol) were stirred in DCM (1.01 mL) and refluxed at 65° C. for 3 h. The reaction was diluted with 100 mL of DCM, washed with H2O (×3), dried, filtered and concentrated. The crude material was dissolved in minimal DCM, loaded onto a preloaded silica loader and eluted off a 40 g column using 0-30% MeOH/DCM over 20 column volumes. The desired fractions were combined and concentrated to provide the title compound. This compound is used in Example 2.

tert-Butyl 4-(4-(oxetan-3-yl)piperazin-1-yl)phenyl(6-(tributylstannyl)imidazo[1,2-a]pyrazin-8-yl)carbamate V: In a 350 mL p-tube, tert-butyl 6-bromoimidazo[1,2-a]pyrazin-8-yl(4-(4-(oxetan-3-yl)piperazin-1-yl)phenyl)carbamate IV (8150 mg, 15.39 mmol), 1,1,1,2,2,2-hexabutyldistannane (11.67 mL, 23.09 mmol), tetrakis(triphenylphosphine)palladium (889.43 mg, 0.77 mmol), and tetrabutylammonium iodide (5686.03 mg, 15.39 mmol) were combined in dioxane (62 mL) and heated to 110° C. overnight. According to LCMS, no starting material remained. The reaction was absorbed onto celite and eluted off a 160 g alumina column using a 0-10-20-30-100% (50% EtOAc/Hex-Hex) gradient holding at 50% for 10-15 column volumes over 50-60 column volumes to provide the title compound V.

2-Bis(tert-butoxycarbonyl)amino-6-bromopyrazine B: To a mixture of 6-bromopyrazin-2-amine (5 g, 28.7 mmol) and di-tert-butyl dicarbonate (25.09 g, 114.94 mmol) was added DCM (10 mL) followed by DMAP (0.351 g, 29 mmol). The reaction was heated to 55° C. for 1 h, cooled to RT, the reaction was partitioned between water and DCM, purified on silica gel and concentrated to provide of 2-bis(tert-butoxycarbonyl)amino-6-bromopyrazine B. LCMS-ESI+ (m/z): [M+H]+: 374.14. 1H NMR (DMSO) δ: 8.84 (d, 2H), 1.39 (s, 18H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate D—route A: tert-Butyl 4-(4-(oxetan-3-yl)piperazin-1-yl)phenyl(6-(tributylstannyl) imidazo[1,2-a]pyrazin-8-yl)carbamate V (215 mg, 0.291 mmol), was combined with 2-bis(tert-butoxycarbonyl) amino-6-bromopyrazine XIV (217.58 mg, 0.581 mmol), bis(triphenylphosphine)palladium(II) dichloride (30.61 mg, 0.044 mmol) and 1,4-dioxane (5 ml). The reaction mixture was stirred in a microwave reactor at 120° C. for 30 min. The reaction mixture was quenched with saturated KF, extracted with EtOAc, purified on silica gel, eluted with EtOAc. The desired fractions were combined and concentrated to provide 100 mg (46% yield) of tert-butyl (6-(6-(bis(tert-butoxycarbonyl)amino)pyrazin-2-yl)imidazo[1,2-a]pyrazin-8-yl)

(4-(4-(oxetan-3-yl)piperazin-1-yl)phenyl)carbamate D. LCMS-ESI+ (m/z): [M+H]+: 744.4. $^1$H NMR (300 MHz d$_6$-DMSO) δ: 9.37 (s, 1H), 9.18 (s, 1H), 8.77 (s, 1H), 8.33 (d, 1H), 7.87 (d, 1H), 7.28-7.25 (d, 2H), 6.92-6.89 (d, 2H), 4.55-4.41 (m, 4H), 3.4 (m, 1H), 3.14-3.11 (m, 4H), 2.37-2.34 (m, 4H), 1.37 (s, 18H), 1.3 (s, 9H).

tert-Butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate D—route B: Step 1: To a dry 250 mL round-bottomed flask was added 2-bis(tert-butoxycarbonyl)amino-6-bromopyrazine B (1.0 g, 1.0 equiv, 2.67 mmol), KOAc (790 mg, 8.02 mmol, 3.0 equiv), 4,4,4',4',5,5,5',5'-octamethyl-2,2'-bi(1,3,2-dioxaborolane) (750 mg, 2.94 mmol, 1.1 equiv), Pd$_2$(dba)$_3$ (171 mg, 0.187 mmol, 0.07 equiv) and X-phos (128 mg, 0.267 mmol, 0.1 equiv) followed by 1,4-dioxane (25 mL) and the solution was sonicated for 5 min and then purged with N$_2$ gas for 5 min. The flask with contents was then placed under N$_2$ atmosphere and heated at 110° C. for 90 min. Once full conversion to the pinacolboronate was achieved by LCMS, the reaction was removed from heat and allowed to cool to RT. Once cool, the reaction contents were filtered through Celite and the filter cake was washed 3×20 mL EtOAc. The resultant solution was then concentrated down to a deep red-orange syrup providing N, N-BisBoc 6-(4,4,5,5-tetramethyl-1,3,2-dioxaborolan-2-yl)pyrazin-2-amine C, which was used directly in the next step.

Step 2: The freshly formed N, N-Bis-Boc-6-(4,4,5,5-tetramethyl-1,3,2-dioxaborolan-2-yl)pyrazin-2-amine C (2.67 mmol based on 100% conversion, 2.0 equiv based on bromide) was dissolved in 20 mL of 1,2-dimethoxyethane and to that solution was added tert-butyl (6-bromoimidazo[1,2-a]pyrazin-8-yl)(4-(4-(oxetan-3-yl)piperazin-1-yl)phenyl)carbamate IV (707 mg, 1.34 mmol, 1.0 equiv), Na$_2$CO$_3$ (283 mg, 2.67 mmol, 2.0 equiv), Pd(PPh$_3$)$_4$ (155 mg, 0.134 mmol, 0.1 equiv) and water (10 mL) and the solution was degassed for 5 min using N$_2$ gas. The reaction was then placed under N$_2$ atmosphere and heated at 110° C. for 90 min LCMS showed complete consumption of the bromide starting material and the reaction was removed from heat and allowed to cool to RT. The reaction was diluted with 100 mL water and 100 mL 20% MeOH/DCM and the organic layer was recovered, extracted 1× sat. NaHCO$_3$, 1× sat brine and then dried over Na$_2$SO$_4$. The solution was then filtered and concentrated down to an orange-red solid. The sample was then slurried in warm MeOH, sonicated then filtered, washing 2×20 mL with cold MeOH and then the cream-colored solid was dried on hi-vacuum overnight to yield 905 mg of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate D.

6-(6-Aminopyrazin-2-yl)-N-(4-(4-(oxetan-3-yl)piperazin-1-yl)phenyl)imidazo[1,2-a]pyrazin-8-amine (Compound I): To a solution of tert-butyl (6-(6-(bis(tert-butoxycarbonyl)amino)pyrazin-2-yl)imidazo[1,2-a]pyrazin-8-yl)(4-(4-(oxetan-3-yl)piperazin-1-yl)phenyl)carbamate D (200 mg, 0.269 mmol) in DCM (2 mL) was added TFA (0.5 mL, 6.578 mmol). The reaction was stirred at rt for 16 h, saturated sodium bicarbonate was added, extracted with EtOAC and purified on silica gel, eluted with 5% MeOH/EtOAc, 20% MeOH/EtOAc. The desired fractions were combined and concentrated to provide Compound I. LCMS-ESI+ (m/k): [M+H]+: 444.2. $^1$H NMR (300 MHz d$_6$-DMSO) δ: 9.5 (s, 1H), 8.588 (s, 1H), 8.47 (s, 1H), 8.12 (d, 1H), 7.95-7.92 (d, 2H), 7.88 (s, 1H), 7.62 (s, 1H), 6.99-6.96 (d, 2H), 6.46 (s, 2H), 4.57-4.53 (m, 2H), 4.48-4.44 (m, 2H), 3.43 (m, 1H), 3.15-3.12 (m, 4H), 2.41-2.38 (m, 4H).

Example 2: Preparation of Compound I Form I

Compound I Form I was prepared by slurrying about 50 mg of Compound I Form IV in EtOAc, IPAc, MEK, or 2-MeTHF at room temperature. It can also be formed by desolvating Compound I Form V and VIII at elevated temperatures. Alternatively, it can be formed by slurrying amorphous Compound I in THF, followed by filtration and drying under vacuum at 50° C.

An X-ray powder diffractogram for Compound I Form I was obtained as described above and is shown in FIG. 1. A DSC analysis was performed as described above and the DSC curve is shown in FIG. 2. A TGA curve was obtained as described above and is shown in FIG. 3. A DVS curve was obtained as described above and is shown in FIG. 4. A single crystal structure was obtained for Compound I Form I indicating that it is a monoclinic crystalline form having unit cell parameters: a equal to 8.62 Å, b equal to 19.71 Å, c equal to 13.46 Å, α equal to 90°, β equal to 108.34° and γ equal to 90°.

Example 3: Preparation of Compound I Form II

Compound I Form II was prepared as an unsolvated form by slurrying about 50 mg of Compound I in acetonitrile at room temperature. It can also be prepared by desolvating Compound I Form IV, VI, VII, and XII at elevated temperatures.

An X-ray powder diffractogram for Compound I Form II was obtained as described above and is shown in FIG. 5. A DSC analysis was performed as described above and the DSC curve is shown in FIG. 6. A TGA curve was obtained as described above and is shown in FIG. 7. A DVS curve was obtained as described above and is shown in FIG. 8.

Example 4: Preparation of Compound I Form III

Compound I Form III was prepared by slurrying a mixture of Compound I Form II and Compound I Form IV in water at room temperature.

An X-ray powder diffractogram for Compound I Form III was obtained as described above and is shown in FIG. 9. A DSC analysis was performed as described above and the DSC curve is shown in FIG. 10. A TGA curve was obtained as described above and is shown in FIG. 11.

Example 5: Preparation of Compound I Form IV

Figure 73:
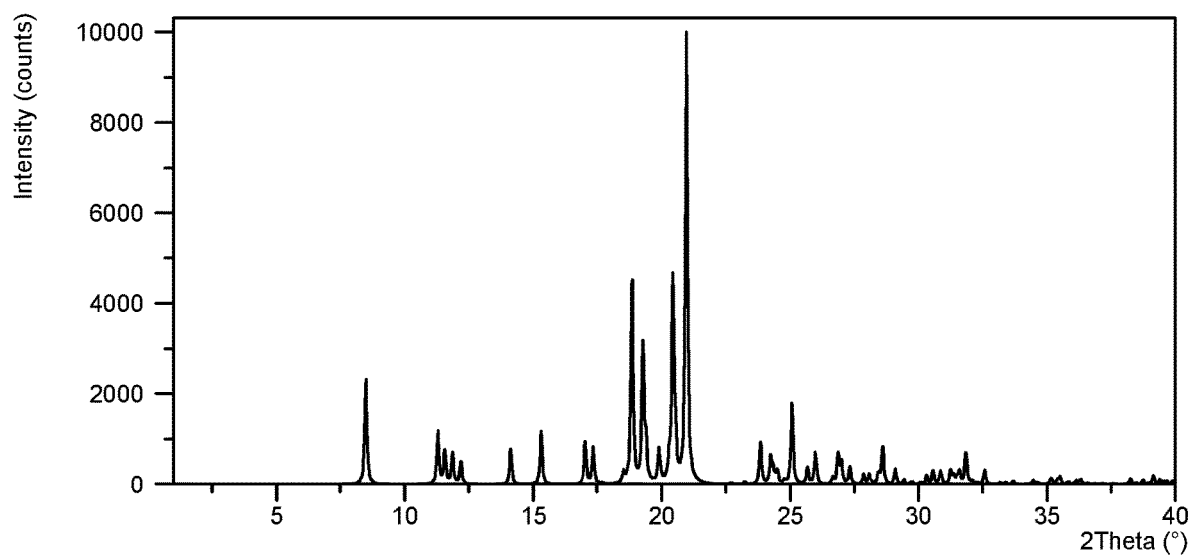
FIG. 73 is a calculated X-ray powder diffractogram of Compound I Form IV.

Compound I Form IV was prepared by heating 5 mg of Compound I Succinate Form I in 1 mL of MeOH with a heat gun until the solids dissolve completely, then letting the sample cool to room temperature over a couple of days. A single crystal structure was obtained for Compound I Form IV indicating that it is a monoclinic crystalline form having unit cell parameters: a equal to 14.29 Å, b equal to 14.57 Å, c equal to 11.57 Å, α equal to 90°, β equal to 92.41° and γ equal to 90°. A calculated X-ray powder diffractogram for Compound I Form IV was obtained and is shown in FIG. 73.

Example 6: Preparation of Compound I Form V

Compound I Form V was prepared by slurrying Compound I Form XIV in a mixture of isopropanol and water (9:1 vol.) at room temperature.

An X-ray powder diffractogram for Compound I Form V was obtained as described above and is shown in FIG. 12. A DSC analysis was performed as described above and the DSC curve is shown in FIG. 13. A TGA curve was obtained as described above and is shown in FIG. 14. A DVS curve was obtained as described above and is shown in FIG. 15.

Example 7: Preparation of Compound I Form VI

Figure 74:
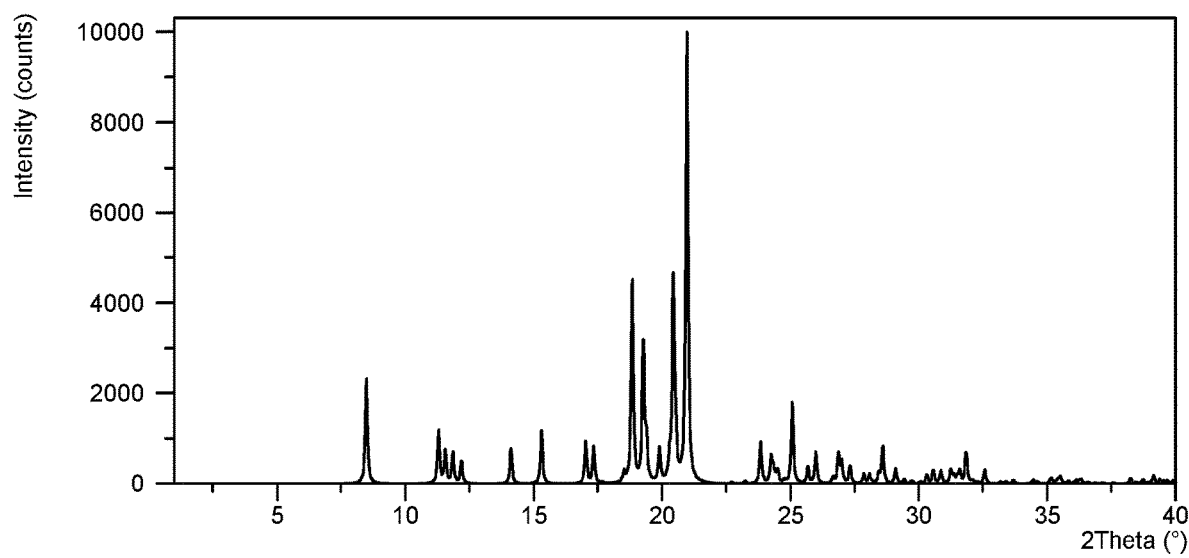
FIG. 74 is a calculated X-ray powder diffractogram of Compound I Form VI.

Compound I Form VI was prepared by heating 7 mg of amorphous Compound I in 1 mL of EtOH with a heat gun until the solids dissolve completely, then letting the sample cool to room temperature. A single crystal structure was obtained for Compound I Form VI indicating that it is a monoclinic crystalline form having unit cell parameters: a equal to 14.52 Å, b equal to 14.91 Å, c equal to 11.58 Å, α equal to 90°, β equal to 91.82° and γ equal to 90°. A calculated X-ray powder diffractogram for Compound I Form VI was obtained and is shown in FIG. 74.

Example 8: Preparation of Compound I Form VII

Compound I Form VII was prepared by slurrying Compound I Form III in isopropanol at room temperature.

An X-ray powder diffractogram for Compound I Form VII was obtained as described above and is shown in FIG. 16. A DSC analysis was performed as described above and the DSC curve is shown in FIG. 17. A TGA curve was obtained as described above and is shown in FIG. 18.

Example 9: Preparation of Compound I Form VIII

Compound I Form VIII was prepared by distilling off DMF from a solution of Compound I in DMF and charging heptane.

An X-ray powder diffractogram for Compound I Form VIII was obtained as described above and is shown in FIG. 19. A DSC analysis was performed as described above and the DSC curve is shown in FIG. 20. A TGA curve was obtained as described above and is shown in FIG. 21.

Example 10: Preparation of Compound I Form IX

Compound I Form IX was prepared by slurrying Compound I Form VIII in MeOH/water (1:1 vol.) at room temperature.

An X-ray powder diffractogram for Compound I Form IX was obtained as described above and is shown in FIG. 22. A DSC analysis was performed as described above and the DSC curve is shown in FIG. 23. A TGA curve was obtained as described above and is shown in FIG. 24. A single crystal structure was obtained for Compound I Form VI indicating that it is a monoclinic crystalline form having unit cell parameters: a equal to 6.92 Å, b equal to 28.97 Å, c equal to 12.73 Å, α equal to 90°, β equal to 92.53° and γ equal to 90°.

Example 11: Preparation of Compound I Form X

Compound I Form X was prepared by slurrying Compound I in dichloromethane at room temperature.

An X-ray powder diffractogram for Compound I Form X was obtained as described above and is shown in FIG. 75.

Example 12: Preparation of Compound I Form XI

Compound I Form XI was prepared by slurrying Compound I in THF at room temperature.

An X-ray powder diffractogram for Compound I Form XI was obtained as described above and is shown in FIG. 76.

Example 13: Preparation of Compound I Form XII

Compound I Form XII was prepared by heating 5 mg of amorphous Compound I in 1 mL of acetonitrile with a heat gun until the solids dissolve completely, then letting the sample cool to room temperature.

An X-ray powder diffractogram for Compound I Form XII was obtained as described above and is shown in FIG. 77. A single crystal structure was obtained for Compound I Form XII indicating that it is a monoclinic crystalline form having unit cell parameters: a equal to 14.55 Å, b equal to 14.53 Å, c equal to 11.77 Å, α equal to 90°, β equal to 90.46° and γ equal to 90°.

Example 14: Preparation of Compound I Form XIII

Compound I Form XIII was prepared by slurrying Compound I Form XIV in propylene glycol at room temperature.

An X-ray powder diffractogram for Compound I Form XIII was obtained as described above and is shown in FIG. 25. A single crystal structure was obtained for Compound I Form XII indicating that it is a monoclinic crystalline form having unit cell parameters: a equal to 14.55 Å, b equal to 14.53 Å, c equal to 11.77 Å, α equal to 90°, β equal to 90.46° and γ equal to 90°.

Example 15: Preparation of Compound I Form XIV

Compound I Form XIV was prepared by drying Compound I Form V in a vacuum oven at about 50° C. with a nitrogen purge overnight.

An X-ray powder diffractogram for Compound I Form XIV was obtained as described above and is shown in FIG. 26. A DSC analysis was performed as described above and the DSC curve is shown in FIG. 27. A TGA curve was obtained as described above and is shown in FIG. 28. A DVS curve was obtained as described above and is shown in FIG. 29.

Example 16: Preparation of Compound I Succinate Form I

Compound I Succinate Form I was prepared by slurrying Compound I with 1.5 mol. eq. of succinic acid in THF at room temperature. Compound I Succinate Form I is disclosed in the U.S. Pat. No. 9,290,505.

Example 17: Preparation of Compound I Sesqui-Succinate Form III

Compound I Sesqui-Succinate Form III was prepared by cooling 100 mL of EtOAc to 10° C. and then charging 5 g Compound I Form VIII and 1.6 mol. eq. succinic acid.

An X-ray powder diffractogram for Compound I Sesqui-Succinate Form III was obtained as described above and is shown in FIG. 30. A DSC analysis was performed as described above and the DSC curve is shown in FIG. 31. A TGA curve was obtained as described above and is shown in FIG. 32.

Example 18: Preparation of Compound I Sesqui-Succinate Form IV

Compound I Sesqui-Succinate Form IV was prepared by charging 50 mg Compound I Form IV and 1.6 mol. eq. succinic acid into 1 mL of MEK at room temperature.

An X-ray powder diffractogram for Compound I Sesqui-Succinate Form IV was obtained as described above and is shown in FIG. 33. A DSC analysis was performed as described above and the DSC curve is shown in FIG. 34. A TGA curve was obtained as described above and is shown in FIG. 35.

Example 19: Preparation of Compound I Sesqui-Succinate Form V

Compound I Sesqui-Succinate Form V was prepared by dissolving Compound I Succinate Form I in 16 volumes of THF/Water (19:1 vol.) at 55° C., then cooling to 30° C. to vacuum distill off water. More THF was charged into the reactor and distilled further until the KF is about 2%. The reactor contents were then cooled to about 22° C. and Compound I Sesqui-Succinate Form V was isolated.

An X-ray powder diffractogram for Compound I Sesqui-Succinate Form V was obtained as described above and is shown in FIG. 36. A DSC analysis was performed as described above and the DSC curve is shown in FIG. 37. A TGA curve was obtained as described above and is shown in FIG. 38.

Example 20: Preparation of Compound I Hemi-Succinate Form I

Compound I Hemi-Succinate Form I was prepared by charging 16 g of amorphous Compound I and 1.5 mol. eq. succinic acid in 7 volumes of THF/water (2:1 vol.) at 60° C., then cooling to room temperature.

An X-ray powder diffractogram for Compound I Hemi-Succinate Form I was obtained as described above and is shown in FIG. 39. A DSC analysis was performed as described above and the DSC curve is shown in FIG. 40. A TGA curve was obtained as described above and is shown in FIG. 41. A DVS curve was obtained as described above and is shown in FIG. 42. A single crystal structure was obtained for Compound I Hemi-Succinate Form I indicating that it is a monoclinic crystalline form having unit cell parameters: a equal to 15.68 Å, b equal to 9.63 Å, c equal to 17.66 Å, α equal to 90°, β equal to 108.12° and γ equal to 90°.

Example 21: Preparation of Compound I Mono-HCl Salt Form I

Compound I Mono-HCl salt Form I was prepared by slurrying Compound I Form IV with 10 vol. of MeOH and 1 mol. eq. of conc. HCl (aq.) at room temperature. The solids were filtered off and placed in a vacuum oven at about 25° C.

An X-ray powder diffractogram for Compound I Mono-HCl salt Form I was obtained as described above and is shown in FIG. 43. A TGA curve was obtained as described above and is shown in FIG. 44.

Example 22: Preparation of Compound I Mono-HCl Salt Form II

Compound I Mono-HCl salt Form II was prepared by slurrying Compound I Mono-HCl Salt Form I in water at room temperature.

An X-ray powder diffractogram for Compound I Mono-HCl salt Form II was obtained as described above and is shown in FIG. 45. A TGA curve was obtained as described above and is shown in FIG. 46. A DVS curve was obtained as described above and is shown in FIG. 47.

Example 23: Preparation of Compound I Mono-HCl Salt Form III

Compound I Mono-HCl salt Form III was prepared by charging 1 mol. eq. of conc. HCl to 10 mL of water containing 1 g of Compound I to make a solution at room temperature, then removing the water and slurrying the remaining solids in propylene glycol. The solids were initially amorphous but crystallized after about 2 years in storage at room temperature.

An X-ray powder diffractogram for Compound I Mono-HCl salt Form III was obtained as described above and is shown in FIG. 48. A DSC curve was obtained as described above and is shown in FIG. 49. A TGA curve was obtained as described above and is shown in FIG. 50. A DVS curve was obtained as described above and is shown in FIG. 51. A single crystal structure was obtained for Compound I Mono-HCl salt Form III indicating that it is a triclinic crystalline form having unit cell parameters: a equal to 11.03 Å, b equal to 12.13 Å, c equal to 12.89 Å, α equal to 66.9°, β equal to 79.52° and γ equal to 83.88°.

Example 24: Preparation of Compound I Sesqui-Adipate Form I

Compound I Sesqui-Adipate Form I was prepared by slurrying Compound I with about 2.1 mol. eq. of 0.1 N adipic acid in THF at room temperature.

An X-ray powder diffractogram for Compound I Sesqui-Adipate Form I was obtained as described above and is shown in FIG. 51. A DSC curve was obtained as described above and is shown in FIG. 52. A TGA curve was obtained as described above and is shown in FIG. 53. A DVS curve was obtained as described above and is shown in FIG. 54. A single crystal structure was obtained for Compound I Sesqui-Adipate Form I indicating that it is a triclinic crystalline form having unit cell parameters: a equal to 8.10 Å, b equal to 13.38 Å, c equal to 16.46 Å, α equal to 71.91°, β equal to 79.15° and γ equal to 76.92°.

Example 25: Preparation of Compound I Mono-Adipate Form I

Compound I Mono-Adipate Form I was prepared by slurrying Compound I with about 2.1 mol. eq. of 0.1 N adipic acid in THF at room temperature.

An X-ray powder diffractogram for Compound I Mono-Adipate Form I was obtained as described above and is shown in FIG. 55. A DSC curve was obtained as described above and is shown in FIG. 56. A TGA curve was obtained as described above and is shown in FIG. 57. A single crystal structure was obtained for Compound I Mono-Adipate Form I indicating that it is a monoclinic crystalline form having unit cell parameters: a equal to 11.04 Å, b equal to 31.08 Å, c equal to 22.23 Å, α equal to 90.00°, β equal to 100.23° and γ equal to 90.00°.

Example 26: Preparation of Compound I Bis-Citrate Form I

Compound I Bis-Citrate Form I was prepared by slurrying Compound I with about 2.1 mol. eq. of 0.1 N citric acid in THF at room temperature.

An X-ray powder diffractogram for Compound I Bis-Citrate Form I was obtained as described above and is shown

Example 27: Preparation of Compound I Sesqui-Fumarate Form I

Compound I Sesqui-Fumarate Form I was prepared by slurrying Compound I with about 2.1 mol. eq. of fumaric acid in THF at room temperature.

An X-ray powder diffractogram for Compound I Sesqui-Fumarate Form I was obtained as described above and is shown in FIG. 61. A TGA curve was obtained as described above and is shown in FIG. 62.

Example 28: Preparation of Compound I Bis-Gentisate Form I

Compound I Bis-gentisate Form I was prepared by slurrying Compound I with about 2.1 mol. eq. of gentisic acid in THF at room temperature.

An X-ray powder diffractogram for Compound I Bis-gentisate Form I was obtained as described above and is shown in FIG. 63. A DSC curve was obtained as described above and is shown in FIG. 64. A TGA curve was obtained as described above and is shown in FIG. 65. A single crystal structure was obtained for Compound I Bis-gentisate Form I indicating that it is a triclinic crystalline form having unit cell parameters: a equal to 12.06 Å, b equal to 13.73 Å, c equal to 14.88 Å, α equal to 64.57°, β equal to 73.71° and γ equal to 77.01°.

Example 29: Preparation of Compound I Mono-BSA Form I

Compound I Mono-BSA salt Form I was prepared by charging 1 mol. eq. of BSA to 10 mL of water containing 1 g of Compound I to make a solution at room temperature, then removing the water and slurrying the remaining solids in MeOH.

An X-ray powder diffractogram for Compound I HCl Material A was obtained as described above and is shown in FIG. 66. A DSC curve was obtained as described above and is shown in FIG. 67. A TGA curve was obtained as described above and is shown in FIG. 68. A DVS curve was obtained as described above and is shown in FIG. 69.

Example 30: Preparation of Compound I Sesqui-Oxalate Form I

Compound I Sesqui-Oxalate Form I was prepared by charging Compound I to 1.8 eq. of oxalic acid in 16 vol. of THF at 40° C.

An X-ray powder diffractogram for Compound I HCl Material B was obtained as described above and is shown in FIG. 70. A DSC curve was obtained as described above and is shown in FIG. 71. A TGA curve was obtained as described above and is shown in FIG. 72.

Example 31: Preparation of Compound I HCl Material A

Compound I HCl Material A was prepared by slurrying Compound I Mono-HCl Salt Form I in isopropanol at room temperature.

An X-ray powder diffractogram for Compound I Sesqui-Oxalate Form I was obtained as described above and is shown in FIG. 78.

Example 32: Preparation of Compound I HCl Material B

Compound I HCl Material B was prepared by slurrying Compound I Mono-HCl Salt Form I in toluene at room temperature.

Figure 79:
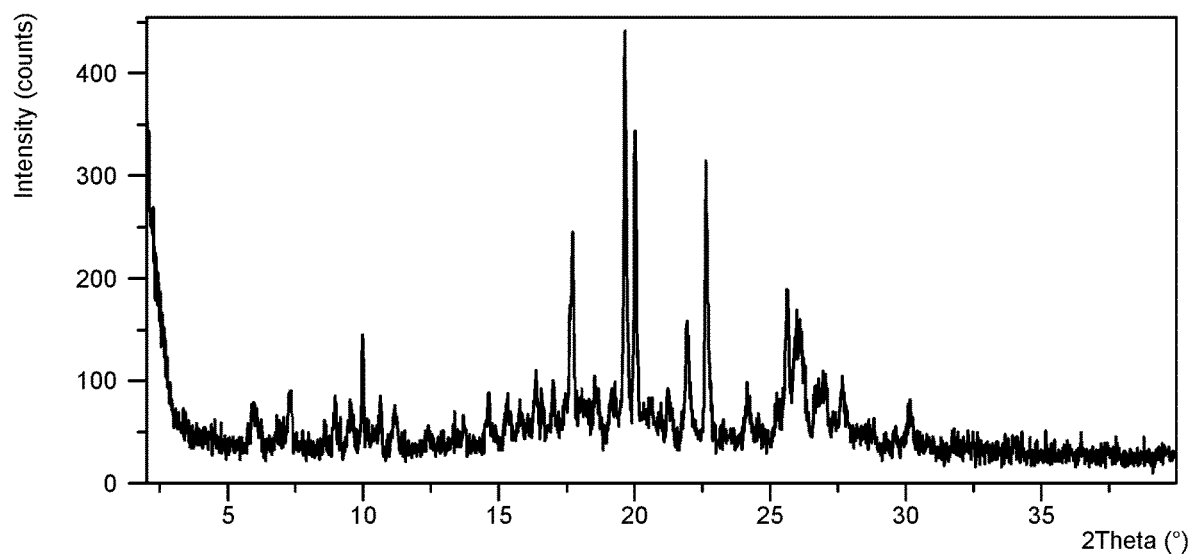
FIG. 79 is an X-ray powder diffractogram of Compound I HCl Material B.

An X-ray powder diffractogram for Compound I Sesqui-Oxalate Form I was obtained as described above and is shown in FIG. 79.

What is claimed is:

1. A crystalline form of Compound I:

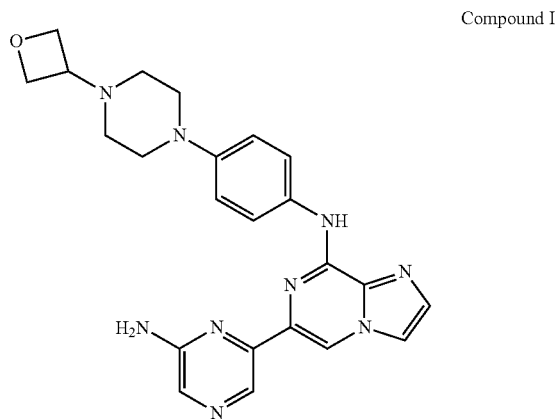 [SMILES: Nc1cncc(-c2cn3ccnc3c(Nc3ccc(N4CCN(C5COC5)CC4)cc3)n2)n1]

Compound I wherein the crystalline form is sesqui-succinate Form III; and
wherein crystalline sesqui-succinate Form III is characterized by an X-ray powder diffractogram comprising characteristic peaks (±0.2° 2θ) at 7.8°±0.2° 2θ, 16.5°±0.2° 2θ, and 21.4°±0.2° 2θ.

2. The crystalline form according to claim 1, wherein the crystalline form is further characterized by an X-ray powder diffractogram comprising additional characteristic peaks (±0.2° 2θ) at 12.2°±0.2° 2θ, 16.0°±0.2° 2θ, and 24.5°±0.2° 2θ.

3. The crystalline form according to claim 1, wherein the crystalline form is further characterized by a differential scanning calorimetry thermogram comprising endothermic peaks having onset temperatures of 118° C., 136° C., and 186° C.

4. A pharmaceutical composition comprising the crystalline form according to claim 1 and a pharmaceutically acceptable excipient.

* * * * *